(12) United States Patent
Harding et al.

(10) Patent No.: US 12,740,734 B2
(45) Date of Patent: Sep. 22, 2026

(54) BLOOD DRAW DEVICE

(71) Applicant: Becton, Dickinson and Company, Franklin Lakes, NJ (US)

(72) Inventors: Weston F. Harding, Lehi, UT (US); Curtis H. Blanchard, Herriman, UT (US); Lucas Farrar, Northborough, MA (US); Justin G. Hortin, Farmington, UT (US); Ken L. Cluff, Lehi, UT (US); Yiping Ma, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 726 days.

(21) Appl. No.: 18/108,231

(22) Filed: Feb. 10, 2023

(65) Prior Publication Data

US 2023/0293069 A1 Sep. 21, 2023

Related U.S. Application Data

(60) Provisional application No. 63/309,336, filed on Feb. 11, 2022.

(51) Int. Cl.
*A61B 5/15* (2006.01)
*A61M 25/06* (2006.01)

(52) U.S. Cl.
CPC ... *A61B 5/150992* (2013.01); *A61M 25/0606* (2013.01)

(58) Field of Classification Search
CPC .......... A61B 5/150992; A61B 5/15003; A61B 5/150206; A61B 5/153
See application file for complete search history.

(56) References Cited

U.S. PATENT DOCUMENTS

| | | | |
|---|---|---|---|
| 3,757,771 | A | 9/1973 | Ruegg et al. |
| 8,366,685 | B2 | 2/2013 | Devgon |
| 2014/0046214 | A1 | 2/2014 | Devgon |
| 2019/0275302 | A1 | 9/2019 | Devgon et al. |

*Primary Examiner* — May A Abouelela
*Assistant Examiner* — Yasmeen S Warsi
(74) *Attorney, Agent, or Firm* — The Webb Law Firm

(57) ABSTRACT

A blood draw device includes a catheter, an introducer having a proximal end portion and a distal end portion, an actuator movably coupled to the introducer, the actuator configured to move relative to the introducer to move the catheter between a first position, in which the catheter is disposed within the introducer, and a second position, in which the distal end portion of the catheter is disposed beyond the distal end portion of the introducer such that at least a first portion of the catheter is disposed within the peripheral intravenous line when the introducer is coupled to the peripheral intravenous line, and a catheter support movably coupled to the introducer. The catheter support including a bracket portion and a hub portion including the passageway and extending from the bracket portion. The bracket portion of the catheter support is biased against a portion of the introducer.

12 Claims, 40 Drawing Sheets

269
270
265
211
271
237
210
230
236
238
212
200
216
240
242

268
A3
277
275
261
214
282
281
280
260
215
262
241
255
A2

334
280

270
X
F
Y

270
X
F
Y
X
F
Y 210
270

210
270
342

344
346
220
345

BLOOD DRAW DEVICE

CROSS-REFERENCE TO RELATED APPLICATION

The present application claims priority to U.S. Provisional Application Ser. No. 63/309,336, entitled "Blood Draw Device", filed Feb. 11, 2022, the entire disclosure of which is hereby incorporated by reference in its entirety.

BACKGROUND OF THE INVENTION

Field of the Invention

The present invention is directed to a blood draw device.

Background of the Invention

The typical hospitalized patient encounters a needle every time a doctor orders a lab test. The standard procedure for blood extraction involves using a metal needle ("butterfly needle") to "stick" patients' veins in their arms or hands. Blood drawing is a manual, labor-intensive process, with the average patient requiring hours of direct skilled labor during a typical hospital stay. This needle stick is not only painful and a major source of patient dissatisfaction, but the nurses or specialized blood drawing personnel (phlebotomists) often have difficulty finding the vein in approximately 10-15% of patients, resulting in multiple, painful "stick" attempts. This results in significantly higher material and labor costs (needles and tubing must be disposed of after every attempt) and increased patient pain and bruising.

The current process for drawing blood is inefficient, taking on average 7-10 minutes, and more than 21 minutes for 10% of patients. These 10% of patients are referred to as Difficult Intra-Venous Access or more commonly as "tough stick" patients. If superficial veins are not readily apparent, blood can be forced into the vein by massaging the beam from wrist to elbow, tapping the site with the index and middle finger, applying a warm, damp washcloth to the site for 5 minutes, or by lowering the extremity over the bedside to allow the veins to fill. Each of these methods is time consuming and therefore costly.

Peripheral intravenous catheters (PIVs) are inserted into most patients while they are hospitalized and used for infusing fluids and medications. However, they are not designed for blood extractions. The failure rates for aspiration reach 20-50% when PIVs have been left inserted for more than a day. Blood extracted from PIVs is often hemolyzed, defined as the rupture of red blood cells and the release of their contents into surrounding fluid, resulting in a discarded sample and need to repeat the blood collection.

Several barriers can contribute to the shortcomings of extracting blood through a PIV. First, most catheters are formed from a soft bio-reactive polymer, which can lead to a potential narrowing or collapse of the catheter as the negative pressure is applied for aspiration. Another barrier is that longer indwelling times can increase debris (e.g., fibrin/platelet clots) that builds up on the tip of the catheter and within the lumen of the catheter and/or PIV. Similarly, such debris can at least partially occlude the lumen of the vein in which the PIV is placed. In some instances, this debris (e.g., fibrin/platelet clots) around the PIV can lead to reduced blood flow within portions of the vein surrounding the inserted PIV (e.g., both upstream and downstream), which in turn, results in improper and/or inefficient aspiration. Another barrier is attributed to a "suction cup" effect, wherein the negative pressure created by aspiration through the catheter and the possible curved path of a vein results in the tip of the catheter adhering to the wall of the vein. As the negative pressure increases the vein can rupture resulting in "blowing the vein," which is a concern for phlebotomists during aspiration through a PIV.

By using a fluid transfer device that inserts a catheter into and/or through the PIV, several of these shortcomings can be overcome. However, during deployment the catheter of the fluid transfer device, especially when the proximal end portion of the catheter reaches the S-curve region of the PIV near where the PVI enters the skin, curves within the PIV in an upward direction, and curves again to pass along the vein, the catheter of the fluid transfer device is subject to a column load which can cause bending, kinking, and or deformation of the catheter of the fluid collection. As the catheter bends, it can move in random directions creating a sinusoidal wave, which then flattens against the sidewall of the housing of the fluid transfer device as the force increases. Additional force can then cause the catheter to double back on itself and collapse. Thus, a need exists for a fluid transfer device that at least solves this problem.

DESCRIPTION OF THE INVENTION

Figure 1:
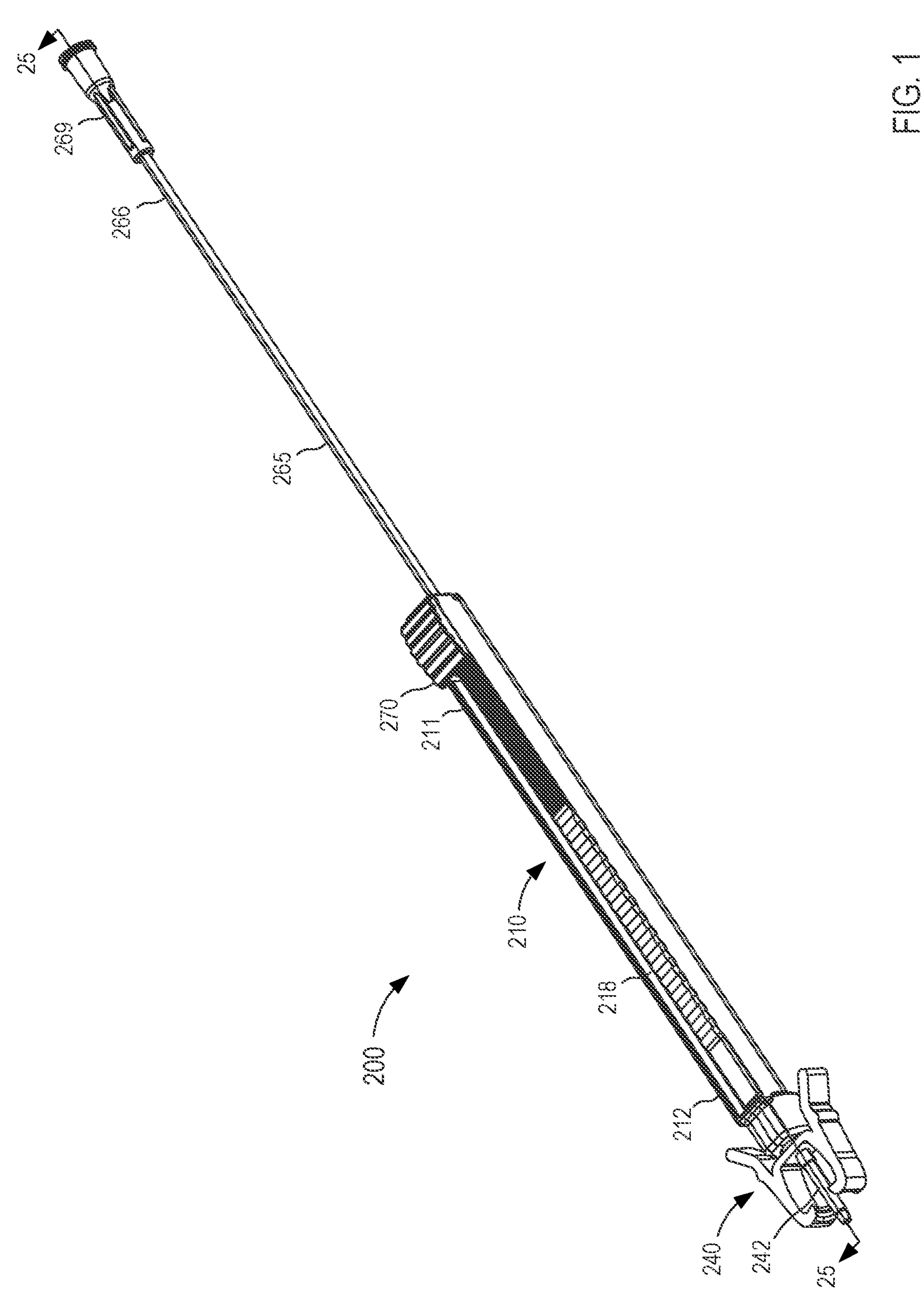
FIG. 1 is a perspective view of the inventive fluid transfer device in a first configuration.

As used herein, unless otherwise expressly specified, all numbers such as those expressing values, ranges, amounts or percentages may be read as if prefaced by the word "about", even if the term does not expressly appear. Any numerical range recited herein is intended to include all sub-ranges subsumed therein. For example, a range of "1 to 10" is intended to include any and all sub-ranges between and including the recited minimum value of 1 and the recited maximum value of 10, that is, all subranges beginning with a minimum value equal to or greater than 1 and ending with a maximum value equal to or less than 10, and all subranges in between, e.g., 1 to 6.3, or 5.5 to 10, or 2.7 to 6.1. Plural encompasses singular and vice versa. When ranges are given, any endpoints of those ranges and/or numbers within those ranges can be combined with the scope of the present invention. "Including", "such as", "for example" and like terms means "including/such as/for example but not limited to".

For purposes of the description hereinafter, spatial orientation terms, as used, shall relate to the referenced embodiment as it is oriented in the accompanying drawings, figures, or otherwise described in the following detailed description. However, it is to be understood that the embodiments described hereinafter may assume many alternative variations and configurations. It is also to be understood that the specific components, devices, features, and operational sequences illustrated in the accompanying drawings, figures, or otherwise described herein are simply exemplary and should not be considered as limiting.

As used herein, the term "catheter" are used interchangeably to describe an element configured to define a passageway for moving a bodily fluid from a first location to a second location, for example, a fluid passageway to move a bodily fluid out of the body. While catheters can be configured to receive a trocar, a guide wire, or an introducer to deliver the catheter to a volume inside the body of a patient, the catheters referred to herein need not include or receive a trocar, guide wire, or introducer.

As used in this specification, the terms "Y-adapter" and "T-adapter" are used to refer to a dual port IV extension set. In this manner, the terms "Y-adapter" and "T-adapter" generally describe an overall shape of the dual port IV extension set. For example, as used herein, a Y-adapter is substantially "Y" shaped including a single port at a first end and two ports angularly disposed at a second end. Furthermore, the terms "Y-adapter" and "T-adapter" are included by way of example only and not limitation. For example, in some embodiments, an apparatus can include a single port IV extension set (e.g., a single port adapter) or a multi-port IV extension set (e.g., an adapter with more than two ports).

As used in this specification, the words "proximal" and "distal" refer to the direction closer to and away from, respectively, a user who would place the device into contact with a patient. Thus, for example, the end of a device first touching the body of the patient would be the distal end, while the opposite end of the device being manipulated by the user would be the proximal end of the device.

The present invention is directed to a fluid transfer device for phlebotomy through a peripheral intravenous line or catheter and a method of using the fluid transfer device to draw blood or administer a drug to a patient.

FIGS. 1-32 illustrate a fluid transfer device 200 according to the invention. The fluid transfer device 200 can be any suitable shape, size, or configuration and can be coupled to a peripheral intravenous catheter (PIV) (not shown in FIGS. 1-32), for example, via a lock and/or adapter. As described in further detail herein, a user can transition the fluid transfer device 200 from a first configuration to a second configuration to advance a catheter 260 through an existing, placed, and/or indwelling PIV when the fluid transfer device 200 is coupled thereto, such that at least an end portion of the catheter 260 is disposed in a distal position relative to the PIV. Moreover, with peripheral intravenous lines having a shape, size, and/or configuration that can vary based on, for example, a manufacturer of the PIV and/or its intended usage, the fluid transfer device 200 can be arranged to allow the fluid transfer device 200 to be coupled to a PIV having any suitable configuration and subsequently, to advance at least a portion of a catheter 260 through the PIV substantially without kinking, snagging, breaking, and/or otherwise reconfiguring the catheter 260 in an undesirable manner. In addition, the fluid transfer device 200 can be manipulated by a user to place a distal surface of the catheter 260 a predetermined and/or desired distance beyond a distal surface of the PIV to be disposed within a portion of a vein that receives a substantially unobstructed flow of blood.

Figure 2:
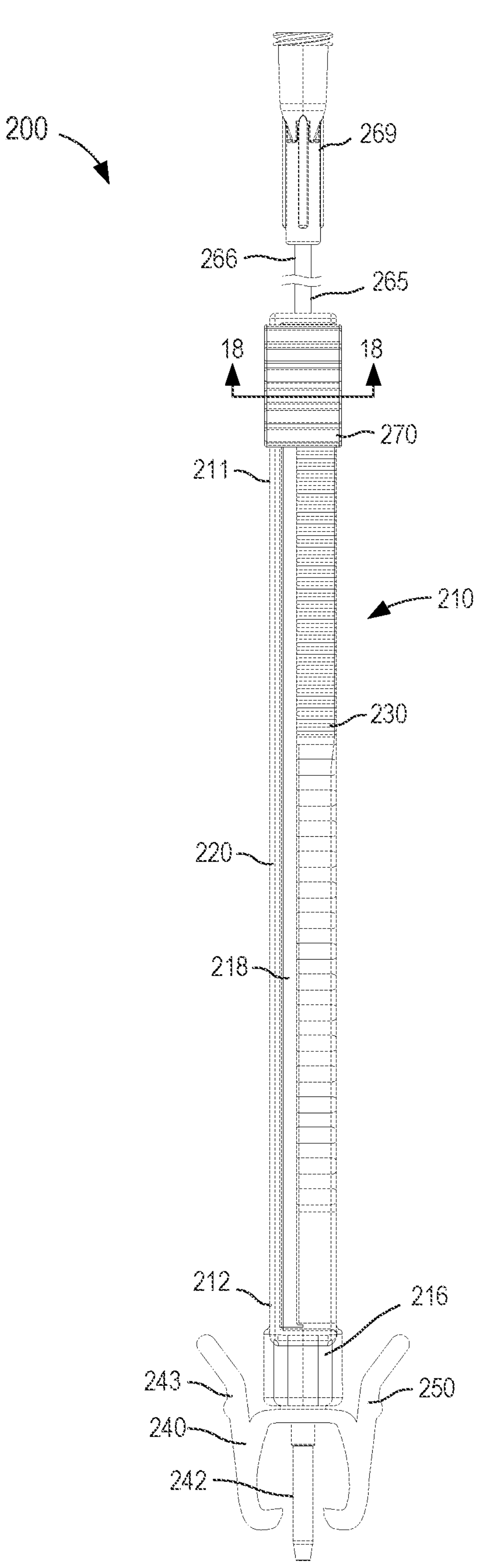
FIG. 2 is a top view of the inventive fluid transfer device shown in FIG. 1.
Figure 3:
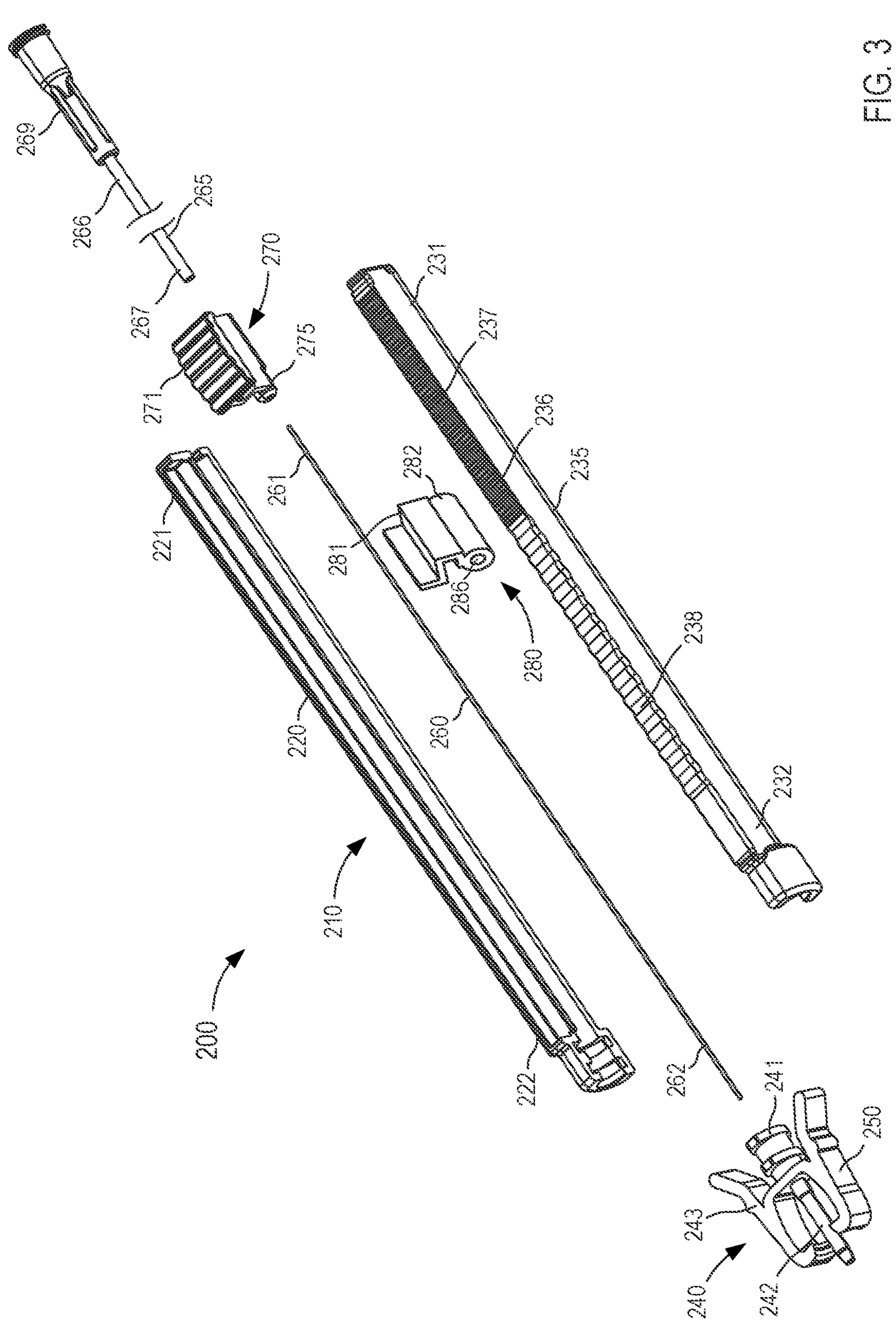
FIG. 3 is an exploded view of the inventive fluid transfer device shown in FIG. 1.

As shown in FIGS. 1-3, the fluid transfer device 200 comprises an introducer 210, a lock 240, a catheter 260, a secondary catheter 265, an actuator 270, and a catheter support 280. The introducer 210 can be any suitable shape, size, or configuration. For example, the introducer 210 can be an elongate member having a substantially circular cross-sectional shape, or the shape of the introducer 210 and/or one or more features or surface finishes of at least a portion of an outer surface of the introducer 210 can be arranged to increase the ergonomic of the fluid transfer device 200, which in some instances, can allow a user to manipulate the fluid transfer device 200 with one hand (i.e., single-handed use).

Figure 4:
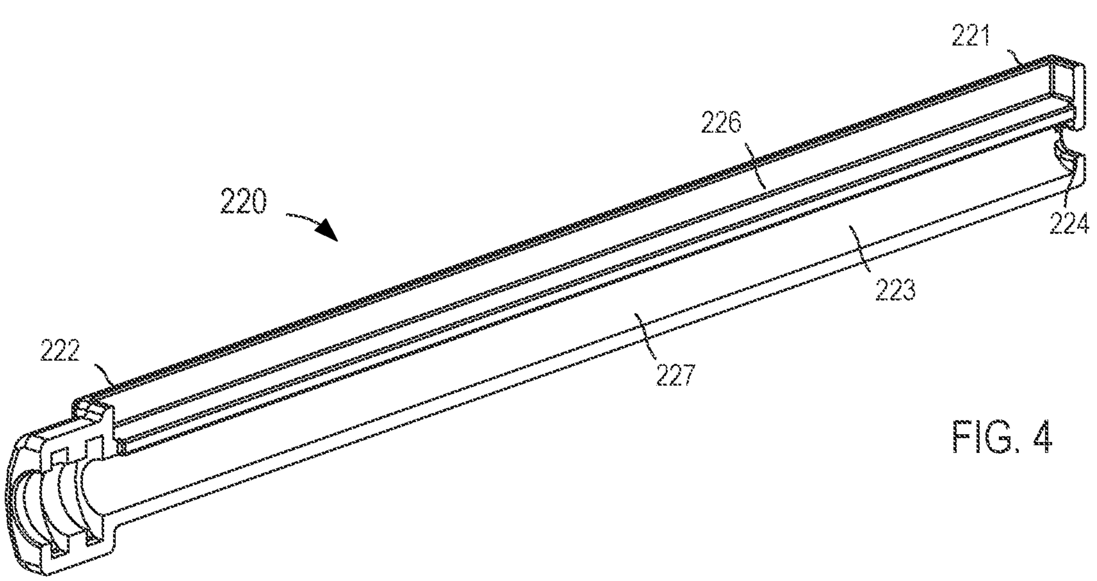
FIG. 4 is a perspective view of a first member of the introducer included in the inventive fluid transfer device of FIG. 1.

As shown in FIGS. 3-10, the introducer 210 of the fluid transfer device 200 includes a first member 220 and a second member 230 that are coupled to collectively form the introducer 210. As shown in FIG. 4, the first member 220 includes a proximal end portion 221, a distal end portion 222, and an inner surface 223. The inner surface 223 has a first portion 226 and a second portion 227. The proximal end portion 221 of the first member 220, and more specifically, a proximal wall of the first member 220 defines a notch 224 configured to selectively receive a portion of the secondary catheter 265, as described in further detail herein.

Figure 5:
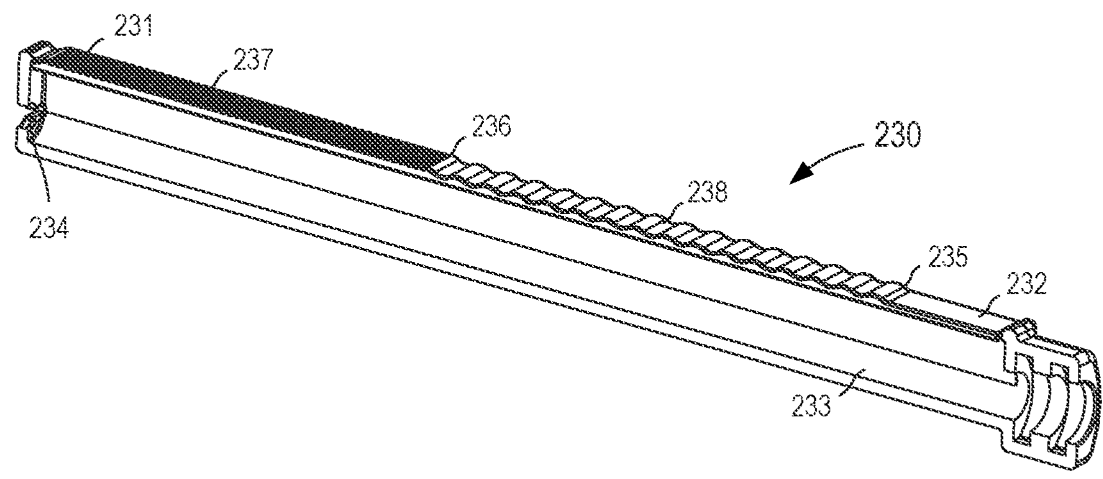
FIG. 5 is a perspective view of a second member of the introducer included in the inventive fluid transfer device of FIG. 1.
Figures 6, 7:
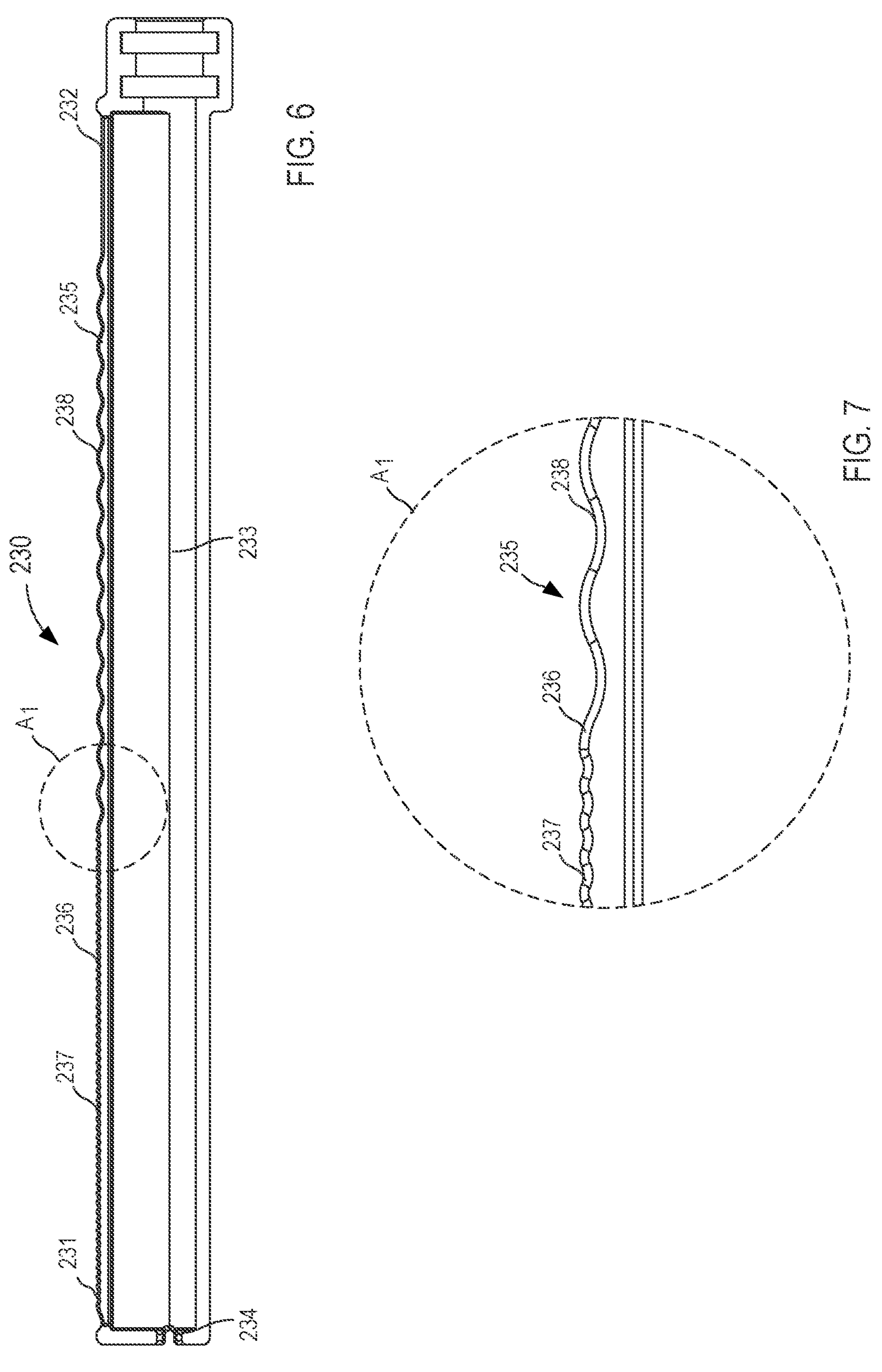
FIG. 6 is a side view of the second member shown in FIG. 5.
FIG. 7 is an enlarged view of the region of the second member identified as $A_1$ in FIG. 6.

As shown in FIGS. 5-7, the second member 230 has a proximal end portion 231, a distal end portion 232, an inner surface 233, and an outer surface 235. As described above with reference to the first member 220, the proximal end portion 231 of the second member 230, and more specifically, a proximal wall of the second member 230 defines a notch 234 configured to selectively receive a portion of the secondary catheter 265. The outer surface 235 of the second member 230 may optionally include a set of ribs 236 distributed along a length of the second member 230. More particularly, each rib 236 extends along a width of the second member 230 and is successively distributed along the length of the second member 230. In this manner, the outer surface 235 defines alternating local minima and local maxima arranged along the length of the second member 230. As described in further detail herein, a portion of the actuator 270 is configured to be advanced along the outer surface 235 forming the set of ribs 236 as a user moves the actuator 270 relative to the introducer 210, which in turn, vibrates the actuator 270 and the catheter 260 coupled thereto. In some instances, this vibration can, for example, facilitate the advancing of the catheter 260 through a portion or the fluid transfer device 200, a portion of the PIV, and/or a portion of the vasculature. Moreover, in some instances, the vibration can provide a user with a haptic and/or audible indicator associated with a position of the catheter 260 relative to the introducer 210 and/or PIV, as described in further detail herein.

The ribs 236 formed by the outer surface 235 of the second member 230 can be any suitable shape, size, and/or configuration. For example, as shown in FIGS. 6 and 7, the set of ribs 236 includes a first portion 237 having a first size and shape, and a second portion 238 having a second size and shape, different from the first size and shape. The first portion 237 of ribs 236 can have any suitable configuration and/or arrangement. For example, each rib in the first portion 237 may be substantially uniform having substantially the same size and shape. Alternatively, each rib included in the first portion 237 can have a size and shape that is different from the remaining ribs of the first portion 237. For example, the size and shape of each rib in the first portion 237 can increase from a proximal most rib having the smallest size and shape to a distal most rib having the largest size and shape. Moreover, while the ribs of the first portion 237 are shown as being substantially symmetrical, each rib of the first portion 237 can be asymmetrical. For example, a proximal surface of each rib can have a first pitch (angle) and a distal surface of each rib can have a second pitch that is greater than the first pitch. Such an asymmetric arrangement can be such that the portion of the actuator 270 moves along the outer surface 235 with a first set of characteristics when moved in a distal direction and moves along the outer surface 235 with a second set of characteristics, different from the first set of characteristics, when moved in a proximal direction. For example, the portion of the actuator 270 can move along the outer surface 235 in the distal direction more freely than in the proximal direction.

Figure 9:
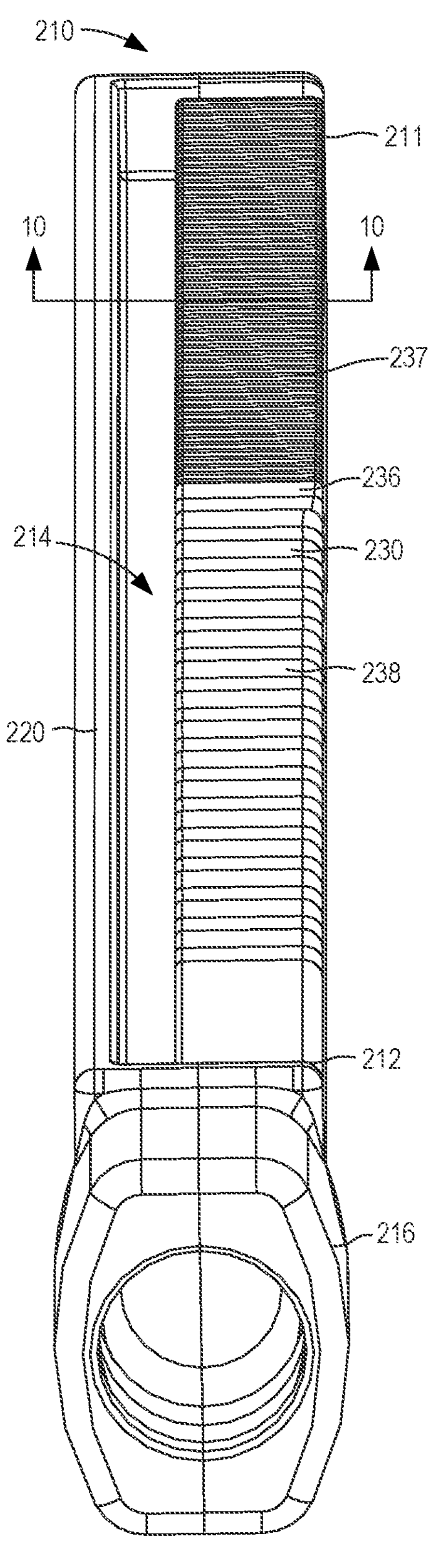
FIG. 9 is a front perspective view of the introducer illustrated in FIG. 8.

Similarly, the second portion 238 of the ribs 236 can have any suitable configuration and/or arrangement. For example, each rib 236 in the second portion 238 may be substantially uniform having substantially the same size and shape as the remaining ribs 236 in the second portion 238. As shown in FIG. 9, each rib in the second portion 238 may have a size and shape that is greater than the size and shape of each rib of the first portion 237. Increasing the size of the ribs 236 of the second portion 238 may provide a larger amount of vibration as the actuator 270 is moved along the outer surface 235 (as described above) or may result in an increase in the force otherwise sufficient to move the portion of the actuator 270 along the outer surface 235. While the ribs 236 of the second portion 238 are shown and described as being substantially uniform and having a larger size than the ribs 236 of the first portion 237, the ribs of the second portion 238 may have any of the arrangements and/or configurations described above with reference to the ribs of the first portion 237.

While the set of ribs 236 transitions from the first portion 237 to the second portion 238 at a given point along the length of the second member 230 (see e.g., FIG. 7), the size and shape of each rib 236 in the set of ribs 236 may increase from a proximal most rib of the first portion 237 having the smallest size and shape to a distal most rib of the second portion 238 having the largest size and shape, such that the size and shape of each of rib in the set of ribs 236 increases with each successive rib, for example, in the distal direction.

The set of ribs 236 may further include more than the first portion 237 and the second portion 238. For example, the second member can include a set of ribs having a first portion and a second portion having a size, shape, and configuration similar to the first portion 237 of the second member 230, and a third portion, disposed between the first portion and the second portion, having a size, shape, and configuration similar to the second portion 238 of the second member 230. In this configuration, the second member 230 includes a proximal portion of ribs and a distal end portion of ribs that are smaller than a medial portion of ribs disposed therebetween.

The arrangement of the set of ribs 236 of the second member 230 may be such that a proximal most rib and a distal most rib are larger and/or otherwise have a shape that is operable to at least temporarily maintain the portion of the actuator 270 in a proximal position relative to the proximal most rib and a distal position relative to the distal most rib, respectively.

While the set of ribs 236 are shown as being formed only on the outer surface 235 of the second member 230, the first member 220 can include an outer surface that forms a set of ribs as an alternative to the set of ribs 236 on the second member 230 or in addition to the set of ribs 236 on the second member 230. In such embodiments, the set of ribs of the first member 220 can be and/or can have any of the configurations and/or arrangements described above with reference to the set of ribs 236 of the second member 230. When ribs are provided on the first member 220 in addition to the ribs 236 provided on the second member 230, the ribs of the first member 220 can be offset from the ribs 236 of the second member 230. For example, the ribs of the first member 220 can have alternating local minima and local maxima, as described above with reference to the ribs 236 that are distributed along a length of the second member 230, such that the local minima and local maxima of the ribs of the first member 220 are aligned with the local maxima and local minima, respectively, of the ribs 236 of the second member 230, or are offset from the local maxima and local minima, respectively, of the ribs 236 of the second member 230. Alternatively, the ribs of the first member 220 can be in varying positions relative to the ribs 236 of the second member 230. In this manner, the introducer 210 can provide a variable arrangement of ribs that can provide, for example, haptic feedback as the actuator 270 is moved relative to the introducer 210.

Figure 8:
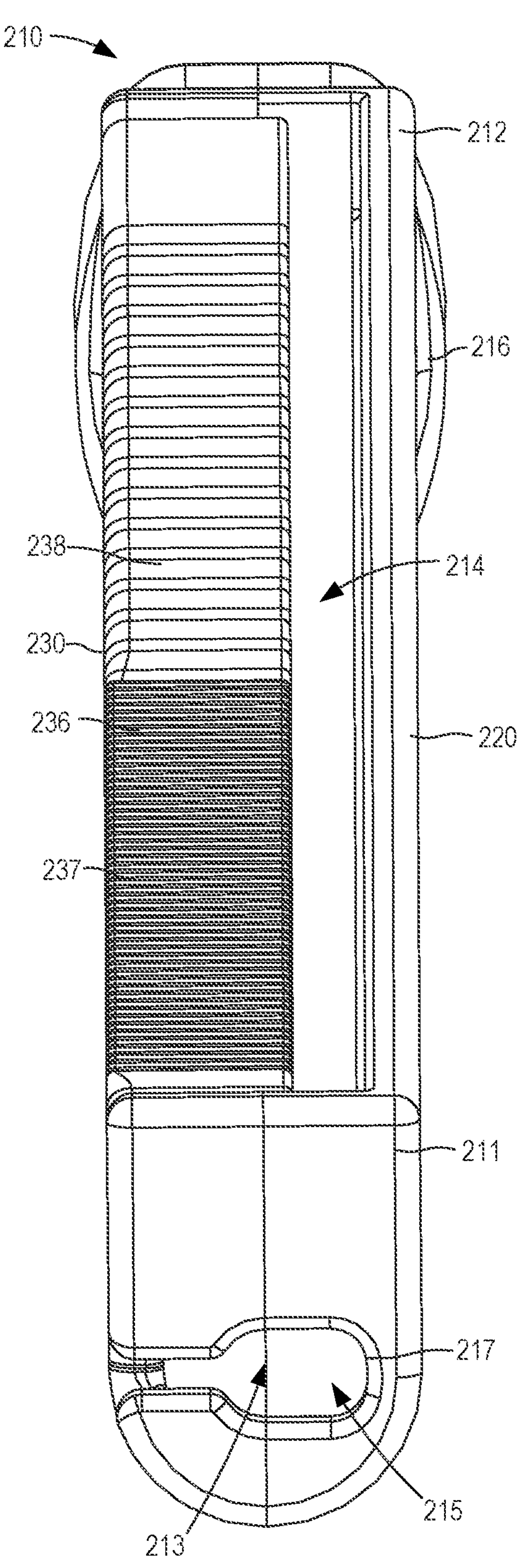
FIG. 8 is a rear perspective view of the introducer formed by coupling the first member illustrated in FIG. 4 to the second member illustrated in FIG. 5.
Figure 10:
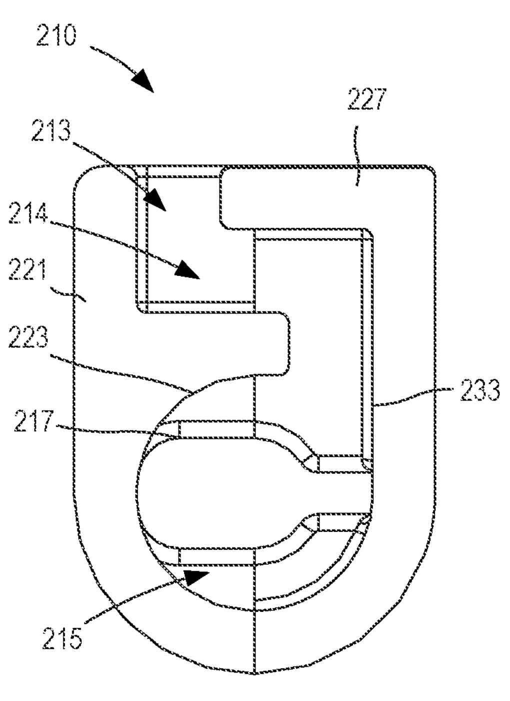
FIG. 10 is a cross-sectional view of the introducer taken along the line 10-10 in FIG. 9.

As shown in FIGS. 8-10, the first member 220 is configured to be coupled to the second member 230 to collectively form the introducer 210. For example, the first member 220 and the second member 230 can be coupled via ultrasonic welding, an adhesive, a mechanical fastener, one or more tabs, snaps, pins, and/or the like to form the introducer 210. Coupling the first member 220 to the second member 230, for example, during a manufacturing process, to form the introducer 210 can facilitate and/or simplify one or more manufacturing processes. For example, forming the introducer 210 from the first member 220 and the second member 230 can reduce undesirable variations in the shape and/or size of the inner surfaces 227, 233, for example, due to draft angles and/or manufacturing tolerances, during manufacturing, which in some instances, can reduce a likelihood of kinks, bends, and/or deformations of the catheter 260 during use of the fluid transfer device 200. Forming the introducer 210 from the first member 220 and the second member 230 can also allow at least the inner surface 227 of the first member 220 to form a tortuous shape that would otherwise present challenges when manufacturing the introducer 210 from a single work piece.

Alternatively, the introducer 210 can be monolithically formed, for example, via injection molding and/or any other suitable manufacturing process, such that the introducer 210 is formed from a single work piece rather than two work pieces, namely, the first member 220 and the second member 230. Thus, when referring to features of the introducer 210, such features can be formed and/or defined by the first member 220, formed and/or defined by the second member

230, collectively formed and/or defined by the first member 220 and the second member 230, or, when the introducer 210 is formed from a single work piece, formed and/or defined by a corresponding portion of the introducer 210.

The first member 220 and the second member 230 collectively form a proximal end portion 211 and a distal end portion 212 of the introducer 210 and collectively define an inner volume 213 of the introducer 210. As shown in FIG. 10, the proximal end portion 211 of the introducer 210 defines an opening 217. Specifically, the opening 217 is collectively formed and/or defined by the notch 224 of the first member 220 and the notch 234 of the second member 230. The arrangement of the proximal end portion 211 may be such that a portion of the opening 217 defined by the notch 224 of the first member 220 has a first size and/or shape and a portion of the opening 217 defined by the notch 234 of the second member 230 has a second size and/or shape that is less than the first size and/or shape, such that a portion of the opening 217 is constricted, pinched, obstructed, and/or otherwise reduced. As described in further detail herein, the opening 217 is configured to receive a portion of the secondary catheter 265, which can be moved within the opening 217 from the larger portion of the opening 217 to the reduced portion of the opening 217, for example, the portion formed by the notch 234 of the second member 230, to obstruct, pinch, and/or clamp the secondary catheter 265.

As shown in FIG. 9, the distal end portion 212 of the introducer 210 includes and/or otherwise forms a coupler 216, and the distal end portion 222 of the first member 220 and the distal end portion 232 of the second member 230 may collectively form the coupler 216 at the distal end portion 212 of the introducer 210. The coupler 216 can be any suitable shape, size, and/or configuration. For example, the coupler 216 may form a set of threads, which can form a threaded coupling with an associated threaded portion of the lock 240, as described in further detail herein. Although not shown in FIG. 9, the distal end portion 212 of the introducer 210 can include and/or can be configured to receive a seal that can selectively seal and/or fluidically isolate the inner volume 213 of the introducer 210 at least from an open portion of the coupler 216. In use, the seal can be transitioned from a sealed or closed configuration to an open configuration to allow, for example, a portion of the catheter 260 to pass therethrough. The seal may contact an outer surface of the catheter 260 or the secondary catheter to define a seal therebetween that is operable to limit and/or substantially prevent a back flow of fluid between the outer surface of the catheter and the seal.

The seal can be any suitable type of seal. For example, the seal can be an O-ring, a one-way valve, a diaphragm, a self-healing diaphragm, a check valve, a single crack valve, and/or any other suitable seal or valve member. The seal may be configured to define and/or otherwise have a predetermined "cracking" pressure, such that the seal transitions from a closed and/or sealed configuration to a substantially open configuration in response to an increase in pressure, for example, within the introducer 210. For example, the seal can be a positive pressure seal or the like. Alternatively, the seal can be a fluid seal such as a saline lock or the like. Although not shown in FIGS. 3-10, the introducer 210 may include a device, mechanism, assembly, and/or the like, which can be manipulated to increase the pressure, for example, via air or other suitable fluid or liquid, within the introducer 210 to transition the seal from the closed configuration to the open configuration. For example, the introducer 210 can include and/or can be coupled to a bulb, pump, a syringe, a fluid source, a mechanical actuator, an electric actuator, and/or the like.

Figure 12:
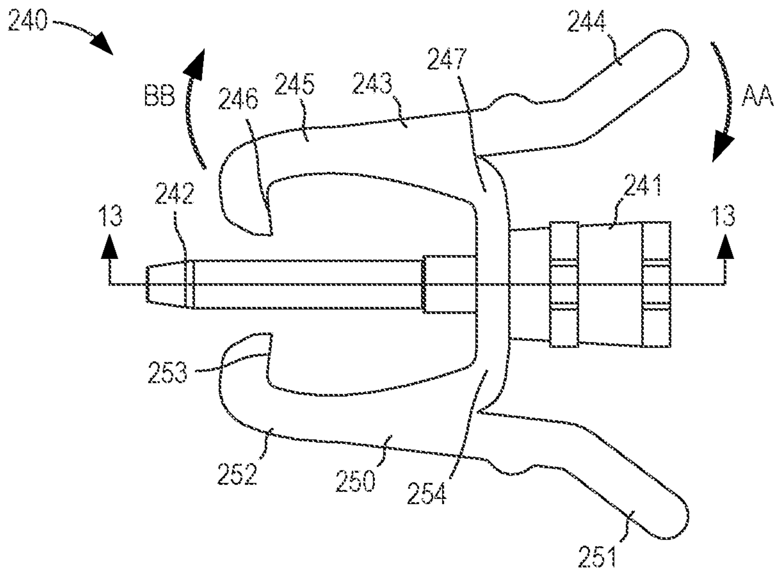
FIG. 12 is a top view of the lock included in the inventive fluid transfer device of FIG. 1.

The inner surface 223 of the first member 220 and the inner surface 233 of the second member 230 collectively define the inner volume 213 of the introducer 210. As shown in FIG. 12, the arrangement of the inner surfaces 223, 233 is such that the inner volume 213 has and/or defines a tortuous cross-sectional shape. For example, the inner volume 213 can have a substantially S-shaped or an at least partially S-shaped cross-sectional shape. More specifically, the inner surface 223 of the first member 220 includes and/or forms a flange 225 configured to separate the first portion 226 of the inner surface 223 from the second portion 227 of the inner surface 223. Thus, the tortuous cross-sectional shape of the inner volume 213 forms and/or defines a first portion 214 of the inner volume 213 and a second portion 215 of the inner volume 213. In this manner, the first portion 214 of the inner volume 213 is spaced apart from the second portion 215 of the inner volume 213 without being fluidically isolated therefrom. In other words, the first portion 214 of the inner volume 213 defines an axis that is parallel to and offset from an axis defined by the second portion 215 of the inner volume 213.

As shown in FIG. 10, the first portion 214 of the inner volume 213 extends through a wall of the introducer 210 such that a slot 218, channel, track, opening, and/or the like that is in fluid communication with the first portion 214 of the inner volume 213 extends through the wall of the introducer 210. Conversely, the second portion 215 of the inner volume 213 is entirely defined and/or enclosed, at least in the circumferential direction, by the introducer 210. The tortuous cross-sectional shape of the inner volume 213 is such that the second portion 215 cannot be viewed via the slot 218 and is out of the line of sight of the slot 218 in fluid communication with the first portion 214 of the inner volume 213, which in turn, limits and/or substantially prevents contamination of the catheter 260 disposed therein.

The second portion 215 of the inner volume 213 is substantially aligned with at least a portion of the opening 217 defined in the proximal end portion 211 of the introducer 210 and at least a portion of an opening defined by the coupler 216. Moreover, the second portion 215 of the inner volume 213 is configured to be substantially aligned with the lock 240 when the lock is coupled to the coupler 216 of the introducer 210, such that an axis defined by the second portion 215 of the inner volume 213 is substantially co-axial with an axis defined by a portion of the lock 240, as described in further detail herein. In this manner, the second portion 215 of the inner volume 213 can receive a portion of the actuator 270 and a portion of the catheter 260. Thus, the actuator 270 can be moved relative to the introducer 210 to move the catheter 260 between a first position, in which the catheter 260 is entirely disposed within the second portion 215 of the inner volume 213, the coupling 216 and/or the lock 240, and a second position, in which at least a portion of the catheter 260 extends outside of the second portion 215 of the inner volume 213 and distal to the introducer 210, as described in further detail herein.

The lock 240 of the fluid transfer device 200 can be any suitable shape, size, and/or configuration. As described above, the lock 240 is configured to be physically and fluidically coupled to the introducer 210 and configured to couple the introducer 210 to the PIV and/or any suitable intermediate device or adapter coupled to the PIV. The lock 240 has a coupler 241, a proboscis 242, a first arm 243, and a second arm 250, as shown in FIGS. 11-14. In addition, the lock 240 defines a lumen 255 extending through the coupler 241 and the proboscis 242. The coupler 241 is configured to couple the lock 240 to the coupler 216 of the introducer 210. Specifically, the coupler 241 includes and/or forms one or more protrusions configured to selectively engage threads defined and/or formed by the coupler 216 of the introducer 210, thereby forming a threaded coupling.

The proboscis 242 extends from the coupler 241 and is disposed between the first arm 243 and the second arm 250. The proboscis 242 can be any suitable shape, size, and/or configuration. In some embodiments, the configuration of the proboscis 242 can be associated with or at least partially based on a size and/or shape of the PIV, a size and/or shape of an adapter, for example, an extension set, a Y-adapter, a T-adapter, or the like, or a collective size and/or shape of the PIV and the adapter. For example, the proboscis 242 can have a length that is sufficient to extend through at least a portion of the PIV or adapter. When an adapter is coupled to the PIV, the proboscis 242 may have sufficient length to extend through the adapter and at least partially into or through the PIV and may have sufficient length for at least a portion of the proboscis 242 to be distal to the PIV. Moreover, the proboscis 242 may have an outer diameter that is similar to or slightly smaller than an inner diameter of a portion of the PIV and/or adapter coupled thereto. For example, an outer surface of the proboscis 242 can be in contact with an inner surface of the PIV when the proboscis 242 is disposed therein. In this manner, the proboscis 242 can provide structural support to at least a portion of the PIV within which the proboscis 242 is disposed. Similarly, the proboscis 242 can have an inner diameter at least partially defining the lumen 255 that is similar to or slightly larger than an outer diameter of a portion of the catheter 260, as described in further detail herein.

Figure 11:
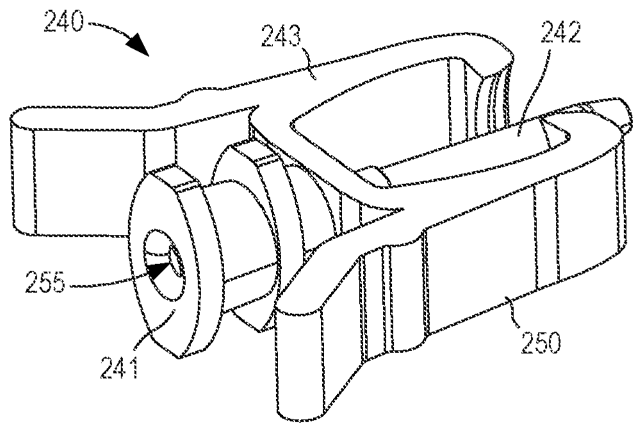
FIG. 11 is a rear perspective view of the lock included in the inventive fluid transfer device of FIG. 1.

The first arm 243 and the second arm 250 of the lock 240 can be any suitable shape, size, and/or configuration. As shown in FIGS. 11 and 12, the first arm 243 has a first end portion 244, a second end portion 245 including a tab 246, and a pivot portion 247 disposed between the first end portion 244 and the second end portion 245. The tab 246 disposed at and/or formed by the second end portion 245 extends from the second end portion 245 toward the proboscis 242. In this manner, the tab 246 can selectively engage a portion of the PIV and/or a portion of an adapter coupled to the PIV to couple the lock 240 thereto, as described in further detail herein.

The pivot portion 247 of the first arm 243 extends from the coupler 241, proboscis 242, and/or second arm 250 in a lateral direction. The first end portion 244 of the first arm 243 is proximal to the pivot portion 247, and the second end portion 245 of the first arm 243 is distal to the pivot portion 247. As such, the first arm 243 can act as a lever configured to pivot about an axis defined by the pivot portion 247 in response to an applied force. For example, a user can exert a force on the first end portion 244 toward the coupler 241 that is sufficient to pivot the first end portion 244 of the first arm 243 toward the coupler 241 as indicated by the arrow AA in FIG. 12 and the second end portion 245 of the first arm 243 away from the proboscis 242 as indicated by the arrow BB in FIG. 12.

As described above with reference to the first arm 243, the second arm 250 of the lock 240 has a first end portion 251, a second end portion 252 including a tab 253, and a pivot portion 254 disposed between the first end portion 251 and the second end portion 252. The first arm 243 and the second arm 250 may be substantially similar in form and function and are arranged in opposite positions and orientations relative to the coupler 241 and proboscis 242, such that the lock 240 is substantially symmetrical about its longitudinal axis. As such, the discussion of the first arm 243 similarly applies to the second arm 250 and thus, the second arm 250 is not described in further detail herein.

As described above, the lock 240 is configured to be coupled to the PIV and/or an adapter coupled to the PIV. For example, a user can exert a lateral force on the first end portion 244 of the first arm 243 and the first end portion 251 of the second arm 250 to pivot the first arm 243 and the second arm 250, respectively, from a first position toward a second position. The pivoting of the first arm 243, therefore, increases the space defined between the proboscis 242 and the second end portion 245 and the tab 246 of the first arm 243. Similarly, the pivoting of the second arm 250 increases the space defined between the proboscis 242 and the second end portion 252 and the tab 253 of the second arm 250. In this manner, the increased space between the proboscis 242 and the arms 243, 250 is sufficient to allow a portion of the PIV and/or an adapter coupled to the PIV to be inserted within the space. Once the portion of the PIV and/or the adapter is in a desired position relative to the lock 240, the user can remove the force and in turn, the arms 243, 250 pivot toward their respective first positions. As a result, the second end portions 245, 252 are moved toward the proboscis 242 until the tabs 246, 253 are placed in contact with a portion of the PIV and/or the adapter. The tabs 246, 253 are configured to engage the portion of the PIV and/or adapter to temporarily couple the lock 240 to the PIV and/or adapter. The lock 240 may be configured to establish three points of contact with the PIV and/or the adapter, namely, the tabs 246, 253, and an outer surface of the proboscis 242 as described above. The tabs 246 and 253 may be configured to produce an audible output such as a click, a vibratory output such as a haptic bump, and/or the like when placed in contact with the portion of the PIV and/or adapter, which can indicate to a user that the lock 240 is properly coupled to the PIV and/or adapter.

The arms 243, 250 of the lock 240 may be positioned to extend horizontally with respect to the introducer 210, i.e., the arms 243, 250 extend outwardly from the sides of the fluid transfer device 200 as shown in the FIG. 1 or may be positioned to extend vertically with respect to the introducer 210, i.e., the arms 243, 250 extend outwardly from the top and bottom of the fluid transfer device 20. Providing the arms 243, 250 in the vertical position reduces the space needed for storing the fluid transfer device 200.

Figure 13:
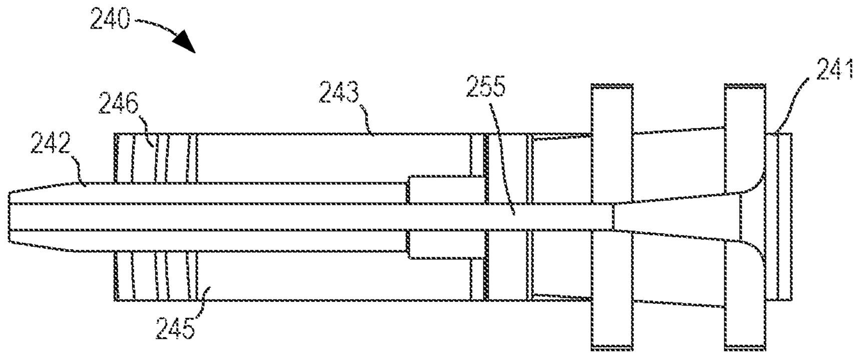
FIG. 13 is a cross-sectional view of the lock taken along the line 13-13 in FIG. 12.

As shown in FIG. 13, the proboscis 242 and the coupler 241 may collectively define the lumen 255. The lumen 255 of the lock 240 defines an axis (not shown) that is aligned with and/or substantially co-axial with the axis defined by the second portion 215 of the inner volume 213. Thus, the lumen 255 of the lock 240 receives a portion of the catheter 260 when the fluid transfer device 200 is transitioned between the first configuration and the second configuration. The lumen 255 may have a size and/or shape that is based at least in part on a size and/or shape of the catheter 260. For example, the lumen 255 may have an inner diameter that is slightly larger than an outer diameter of at least a portion of the catheter 260. The lock 240 acts as an external guide that supports and/or guides the catheter 260 as the catheter 260 is moved within the lumen 255, which in turn, can reduce and/or substantially prevent undesirable bending, kinking, flexing, and/or deforming of the catheter 260.

Although the lock 240 is shown and described above as including the proboscis 242, the lock need not form a proboscis. For example, the lock may include a relatively short hub or the like configured to engage a portion of the PIV and/or an adapter coupled to the PIV. Alternatively, the fluid transfer device can include and/or can be used with a proboscis or guide member not formed with or by the lock configured to be disposed, for example, between a PIV and an adapter such as an IV extension set. For example, such a proboscis or guide member may have an inner surface that is funnel-shaped and/or is shaped similar to the inner surface of the proboscis 242. In this manner, the inner surface of such a proboscis and/or guide member can guide a portion of the catheter 260 as the catheter 260 is moved between the first position and the second position. In some embodiments, the lock 240 including the proboscis 242 can be used in conjunction with such an external or separate proboscis and/or guide member by inserting a portion of the proboscis 242 of the lock 240 into the proboscis and/or guide member when the lock 240 is coupled to an adapter, for example, an IV extension set.

The actuator 270 of the fluid transfer device 200 is coupled to the catheter 260 and can be moved along a length of the introducer 210 to transition the fluid transfer device 200 between its first configuration, in which the catheter 260 is in the first position, and its second configuration, in which the catheter 260 is in the second position. The actuator 270 can be any suitable shape, size, and/or configuration. For example, the actuator 270 can have a size and shape that is associated with and/or based at least in part on a size and/or shape of the introducer 210.

As shown in FIGS. 13-17, the actuator 270 includes a first portion 271, the second portion 275, and a wall 277 extending therebetween. The first portion 271 of the actuator 270 is at least partially disposed within the first portion 214 of the inner volume 213 defined by the introducer 210 and the second portion 275 of the actuator 270 is disposed within the second portion 215 of the inner volume 213.

The first portion 271 of the actuator 270 includes an engagement member 272. The arrangement of the actuator 270 is such that the engagement member 272 is disposed outside of the introducer 210 while the rest of the first portion 271 is within the first portion 214 of the inner volume 213 defined by the introducer 210. As such, the engagement member 272 can be engaged and/or manipulated by a user, for example, by a finger or thumb of the user, to move the actuator 270 relative to the introducer 210. The engagement member 272 may include a set of ridges and/or any suitable surface finish that can, for example, increase the ergonomic of the actuator 270 and/or fluid transfer device 200.

The engagement member 272 includes a tab 273 disposed at or near a proximal end portion of the engagement member 272. The tab 273 can be any suitable tab, rail, ridge, bump, protrusion, knob, roller, slider, etc. that extends from a surface of the engagement member 272. The tab 273 is configured to selectively engage the outer surface 235 of the second member 230 of the introducer 210. More specifically, the tab 273 is in contact with the ribs 236 formed by the second member 230 and moves along each successive rib as the actuator 270 is moved along a length of the introducer 210.

Figure 16:
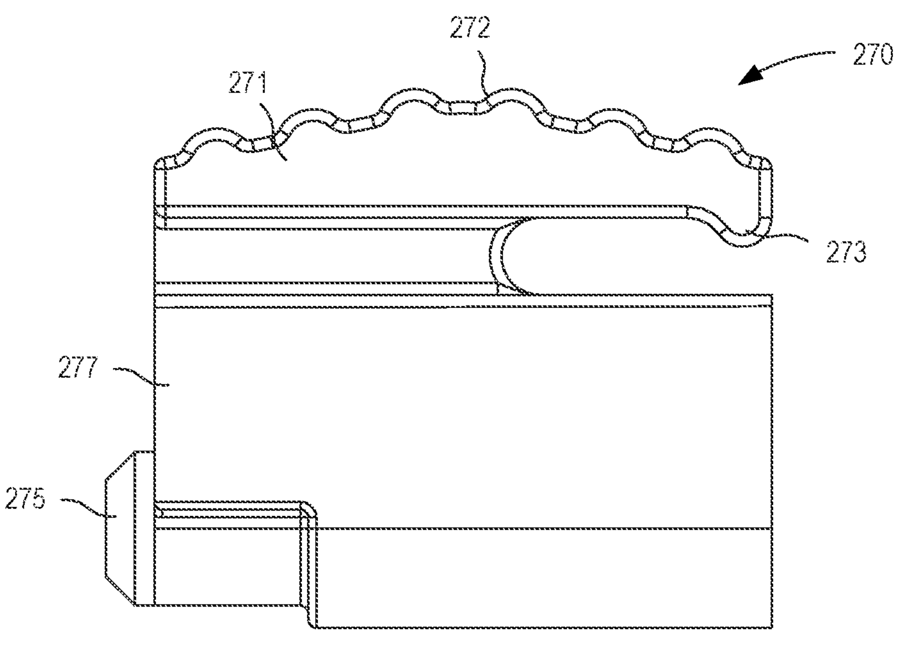
FIG. 16 is a side view of the actuator shown in FIG. 14.

As described above with reference to the set of ribs 236 of the second member 230, the tab 273 can have any suitable shape, size, and/or configuration. For example, as shown in FIG. 16, the tab 273 can include a substantially rounded surface that can be moved along the set of ribs 236. The size and/or shape of the tab 273 may be based at least in part on the size and/or shape of the ribs 236 such that a desired surface area of the tab 273 is in contact with the ribs 236 as the actuator 270 is moved relative to the introducer 210. Further, the amount of friction defined between the set of ribs 236 and the tab 273 can be based at least in part on the surface area of the tab 273 that is in contact with the set of ribs 236. Moreover, the amount of friction defined between the set of ribs 236 and the tab 273 can be based at least in part on a position of the tab 273 relative to each rib. For example, the amount of friction defined between the tab 273 and a rib can increase as the tab 273 moves closer to, for example, a local maxima and can decrease as the tab 273 moves away from the local maxima. The tab 273 may have a size and/or shape that allows the tab 273 to move with substantially less friction between each adjacent rib, for example, between adjacent local maximums, such that the arrangement of the tab 273 and the set of ribs 236 can allow for a desired amount of "play" between adjacent ribs 236.

With the first portion 237 of the set of ribs 236 having a smaller size than the second portion 238 of the set of ribs 236, a first portion or first surface area of the tab 273 can be in contact with the first portion 237 of the set of ribs 236 and a second portion or second surface area of the tab 273 can be in contact with the second portion 238 of the set of ribs 236. In this manner, the tab 273 can move along the first portion 237 with a first set of characteristics and can move along the second portion 238 with a second set of characteristics different from the first set of characteristics. For example, a force sufficient to move the tab 273 along the second portion 238 of the set of ribs 236 can be greater than a force otherwise sufficient to move the tab 273 along the first portion 237 of the set of ribs 236. Alternatively or in addition, the movement of the tab 273 along the second portion 238 of the set of ribs 236 may result in, for example, a larger amount of vibration of the actuator 270 than an amount of vibration otherwise resulting from the movement of the tab 273 along the first portion 237 of the set of ribs 236. Similarly, the shape of the tab 273 can be such that the tab 273 moves along the set of ribs 236 in the distal direction in response to an applied force that is insufficient to move the tab 273 along the set of ribs 236 in the proximal direction. For example, as shown in FIG. 16, the tab 273 may have an asymmetric shape, wherein a proximal surface of the tab 273 has a greater pitch than a pitch of the distal surface.

While the engagement member 272 and tab 273 are particularly shown and described above, in other embodiments, the actuator can include an engagement member and/or tab having any suitable configuration. For example, while the tab 273 is shown as being disposed at or near a proximal end portion of the engagement member 272, in other embodiments, the engagement member may include a first tab disposed at or near a proximal end portion and a second tab disposed at or near a distal end portion, each of which can be selectively in contact with a set of ribs disposed on an outer surface of an introducer 210. In some embodiments, a space defined between a surface of the wall 277 and a surface of the engagement member 272 can be increased or decreased, which can result in an increase or decrease in an amount of travel of the actuator 270 relative to the introducer 210 in a direction other than an axial direction, such that the increase or decrease in space between the surface of the wall 277 and the surface of the engagement member 272 results in, for example, an increase or decrease of the amount the actuator 270 can "tilt" relative to the introducer 210. In other embodiments, the arrangement of the engagement member 272, the tab 273, and/or the set of ribs 236 of the introducer 210 can be modified, altered, tuned, adjusted, and/or otherwise changed such that the actuator 270 moves relative to the introducer 210 with a desired set of characteristics. For example, the arrangement of the actuator 270 and/or introducer 210 can increase or decrease an amount the actuator 270 vibrates as it is moved relative to the introducer 210, increase or decrease the amount of force sufficient to move the actuator 270 relative to the introducer 210, increase or decrease the amount of movement of the actuator 270 relative to the introducer 210 in any suitable direction other than the axial direction (i.e., the proximal direction and distal direction), and/or the like.

Figure 17:
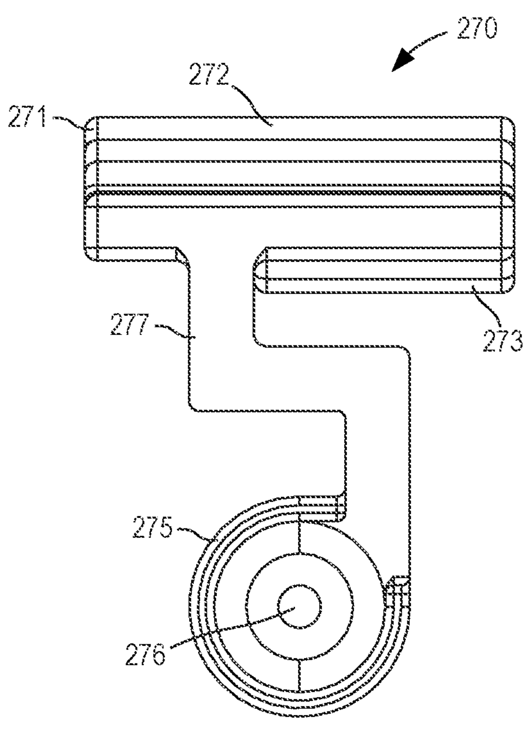
FIG. 17 is a front view of the actuator shown in FIG. 14.
Figure 18:
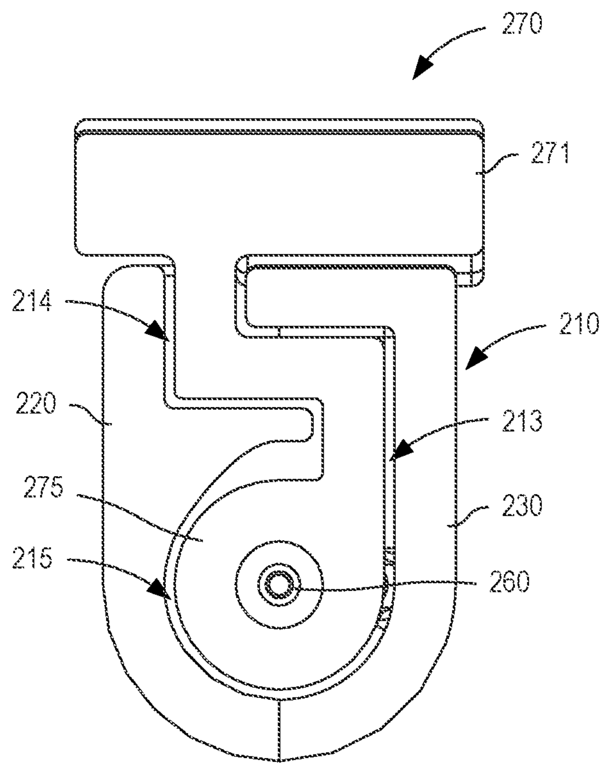
FIG. 18 is a cross-sectional view of the inventive fluid transfer device taken along the line 18-18 in FIG. 4.

As shown, in FIGS. 17 and 18, the second portion 275 has a cross-sectional shape that is based at least in part on a cross-sectional shape of the second portion 215 of the inner volume 213 defined by the introducer 210, for example, at least a partially circular cross-sectional shape. In this manner, the inner surface 223 of the first member 220 and the inner surface 233 of the second member 230 can support and/or guide the second portion 275 of the actuator 270 as the actuator 270 moves relative to the introducer 210. As shown, the second portion 275 defines an opening 276 configured to receive a proximal end portion 261 of the catheter 260 and a distal end portion 267 of the secondary catheter 265. In some embodiments, the proximal end portion 261 of the catheter 260 can form a friction fit with an inner surface of the second portion 275 of the actuator 270 when the proximal end portion 261 is disposed in the opening 276. Similarly, the distal end portion 267 of the secondary catheter 265 can form a friction fit with an inner surface of the second portion 275 of the actuator 270 when the distal end portion 267 is disposed in the opening 276. As such, the catheter 260 and the secondary catheter 265 can be maintained in a fixed position relative to the actuator 270 and thus, move concurrently with the actuator 270 as the actuator 270 is moved relative to the introducer 210.

The wall 277 of the actuator 270 couples the first portion 271 of the actuator 270 to the second portion 275 of the actuator 270. As shown in FIGS. 17 and 18, the wall 277 has a tortuous cross-sectional shape that is based at least in part on the tortuous cross-sectional shape of the inner volume 213 defined by the introducer 210. In this manner, the first portion 271 of the actuator 270 can define an axis that is parallel to but offset from an axis defined by the second portion 275 of the actuator 270. For example, the wall 277 can have a substantially S-shaped or an at least partially S-shaped cross-sectional shape, or the wall 277 can form dogleg shape or the like. The tortuous cross-sectional shape of the wall 277 and thus, the actuator 270 is such that the second portion 275 of the actuator 270 cannot be viewed via the first portion 214 of the inner volume 213 and is out of the line of sight of the first portion 214 of the inner volume 213 defined by the introducer 210. Similarly, the catheter 260 cannot be viewed via the first portion 214 of the inner volume 213 defined by the introducer 210 when the catheter 260 is in the first position. That is to say, the geometry of the actuator 270 and/or the introducer 210, for example, the tortuous cross-sectional shape of the inner volume 213, the height and/or width of the introducer 210, etc. is configured such that the catheter 260 is at least partially isolated within the second portion 215 of the inner volume 213 when the catheter 260 is in the first position. In this manner, the structure of the introducer 210 and/or the actuator 270 can protect and/or isolate the catheter 260 from a volume outside of the introducer 210, which in turn, can limit and/or substantially prevent contamination of the catheter 260. For example, in some embodiments, the introducer 210 and/or the actuator 270 can act as a "sneeze guard" or the like configured to at least partially isolate the catheter 260 at least when the catheter 260 is in the first position.

Figure 14:
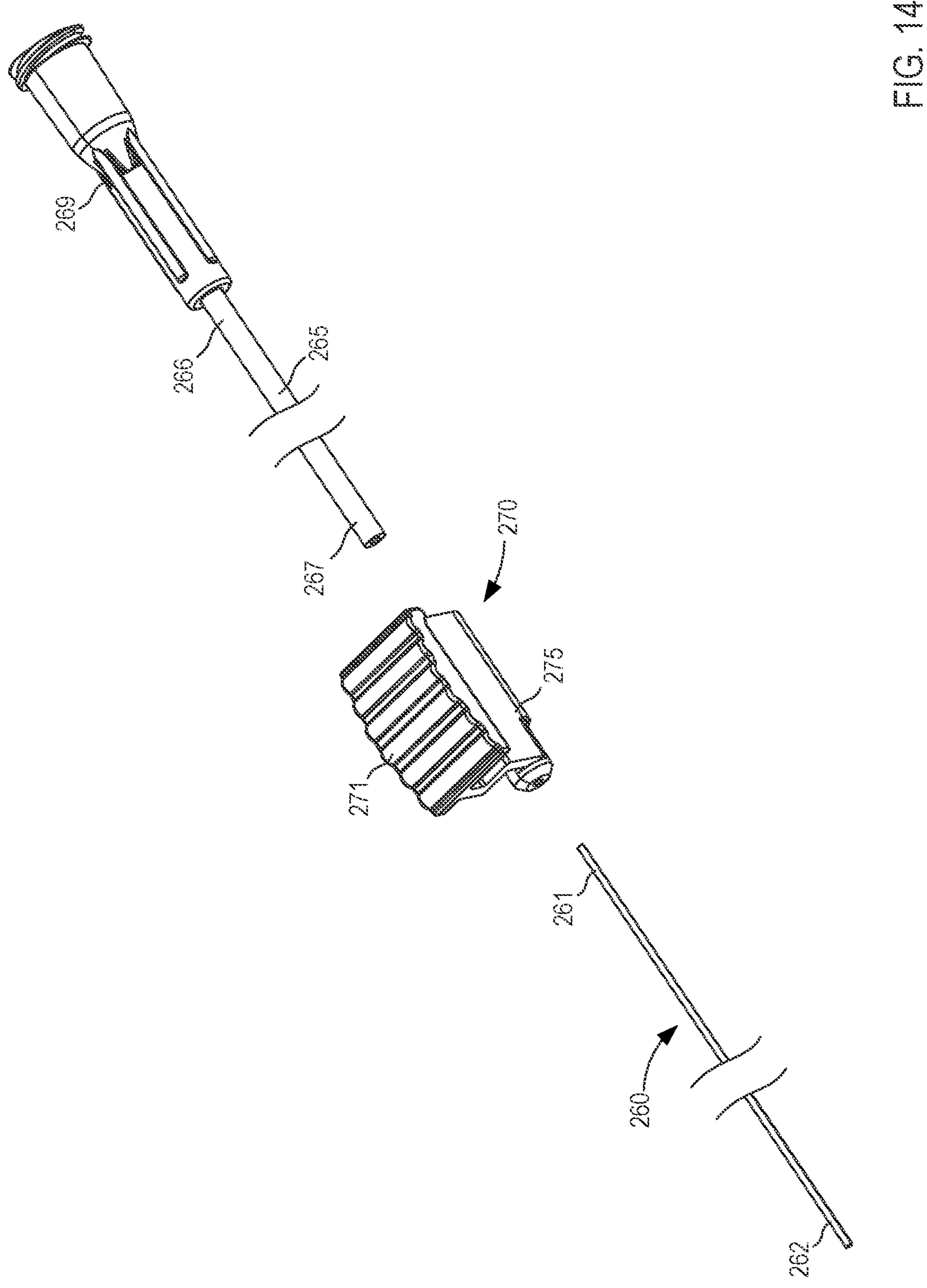
FIG. 14 is an exploded perspective view of the catheter, the secondary catheter, and the actuator included in the inventive fluid transfer device of FIG. 1.
Figure 15:
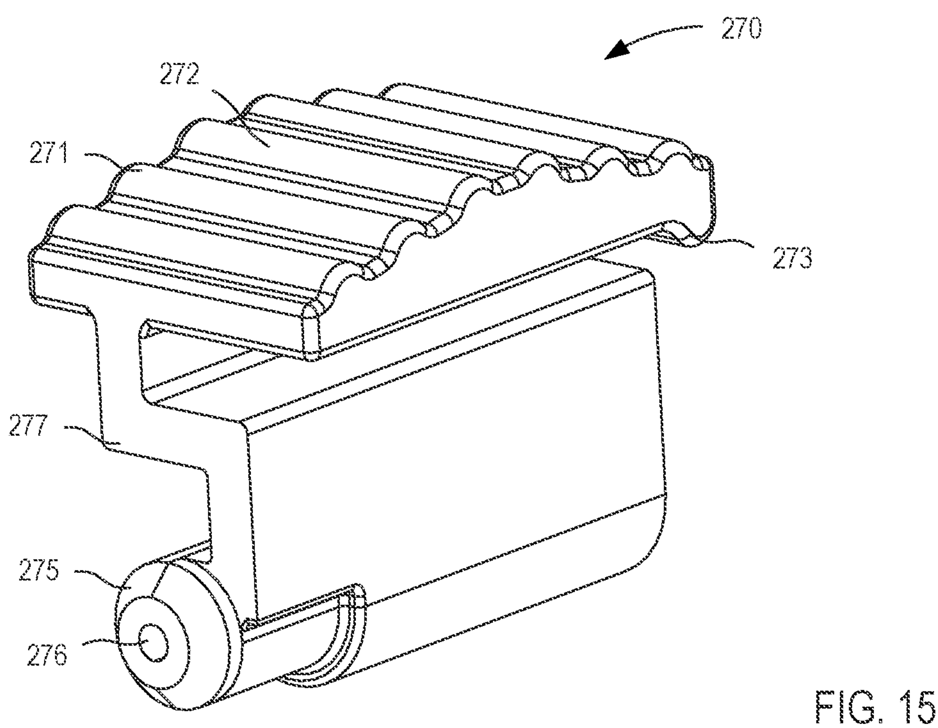
FIG. 15 is a perspective view of the actuator shown in FIG. 14.

As described above, at least a portion of the catheter 260 and at least a portion of the secondary catheter 265 are movably disposed within the second portion 215 of the inner volume 213 defined by the introducer 210. As shown in FIG. 14, the catheter 260 has a proximal end portion 261 and a distal end portion 262 and defines a lumen 263 (see e.g., FIG. 28). The proximal end portion 261 of the catheter 260 is coupled to the second portion 275 of the actuator 270. In this manner, the actuator 270 can be moved relative to the introducer 210 to move the catheter 260 between a first position, in which the catheter 260 is disposed within the introducer 210, for example, with the entire catheter 260 disposed within the introducer 210 or within the introducer 210 and the lock 240, and a second position, in which the distal end portion of the catheter 260 is at least partially disposed in a position distal to the lock 240 and/or the PIV (not shown) when the lock 240 is coupled to the PIV, as described in further detail herein. The distal end portion 262 can be any suitable shape, size, and/or configuration and can define at least one opening in fluid communication with the lumen 263. For example, the distal end portion 262 of the catheter can be substantially similar to any of those described in U.S. Pat. No. 8,366,685 (referred to herein as the "'685 Patent") entitled, "Systems and Methods for Phlebotomy Through a Peripheral IV Catheter," filed on Apr. 26, 2012, the disclosure of which is incorporated herein by reference in its entirety.

While the invention is described herein as including a catheter and a secondary catheter, the catheter and a secondary catheter may be replace by a probe or a guidewire that is inserted into or through the PIV in the same manner as the catheter, or a probe or guidewires may be inserted through the catheter of the fluid transfer device and into or through the PIV.

The catheter 260 can be any suitable shape, size, and/or configuration. For example, at least a portion of the catheter 260 can have an outer diameter that is substantially similar to or slightly smaller than an inner diameter defined by the lumen 255 of the lock 240, as described above, or an outer surface of the catheter 260 can be configured to contact an inner surface of the lock 240 that defines at least a portion of the lumen 255. In this manner, an inner surface of the portion of the lock 240 defining the lumen 255 can guide the catheter 260 as the catheter 260 is moved between the first position and the second position. Such an arrangement can limit and/or can substantially prevent bending, deforming, flexing, and/or kinking of the catheter 260 as the catheter 260 is moved between the first position and the second position. Moreover, the length of the catheter 260 can be sufficient to define a predetermined and/or desired distance between the distal surface of the catheter 260 and the distal surface of the PIV when the catheter 260 is in the second position, as described in further detail herein.

The catheter 260 may be formed from any suitable material or combination of materials, which in turn, can result in the catheter 260 having any suitable stiffness or durometer. For example, the catheter 260 can be formed of a relatively flexible biocompatible material with a Shore durometer of approximately 20 Shore A to 50 Shore D, approximately 20 Shore A to 95 Shore D, approximately 70 Shore D to 85 Shore D, and/or any other suitable range of Shore durometer. At least a portion of the catheter 260 may be formed of a braided material or the like, which can modify, change, and/or alter a flexibility of the catheter 260 in response to a bending force. By forming at least a portion of the catheter 260 from the braided material, the amount of deformation of the catheter 260 in response to a bending force prior to buckling, kinking, and/or otherwise obstructing the lumen 263 of the catheter 260 can be increased. Similarly, forming at least a portion of the catheter 260 of a braided material can result in compression and/or deformation in response to a compression force exerted in a direction of a longitudinal centerline defined by the catheter 260 (e.g., an axial force or the like). In this manner, the catheter 260 can absorb a portion of the force associated with, for example, impacting an obstruction or the like. In some instances, such an arrangement can reduce buckling and/or kinking of the catheter 260 as well as reduce and/or substantially prevent damage to vascular structures that may otherwise result from an impact of the catheter 260. Moreover, forming at least a portion of the catheter 260 from the braided material can increase the amount of vibration transmitted through the catheter 260 in response to the portion of the actuator 270 advancing along the set of ribs 236 of the introducer 210 as described above. While the catheter 260 is described above as including at least a portion formed of a braided material, at least a portion of the catheter 260 can be formed of and/or can include a support wire, a stent, a fenestrated catheter, and/or the like such as those described in the '685 Patent incorporated by reference above.

Figures 24, 25:
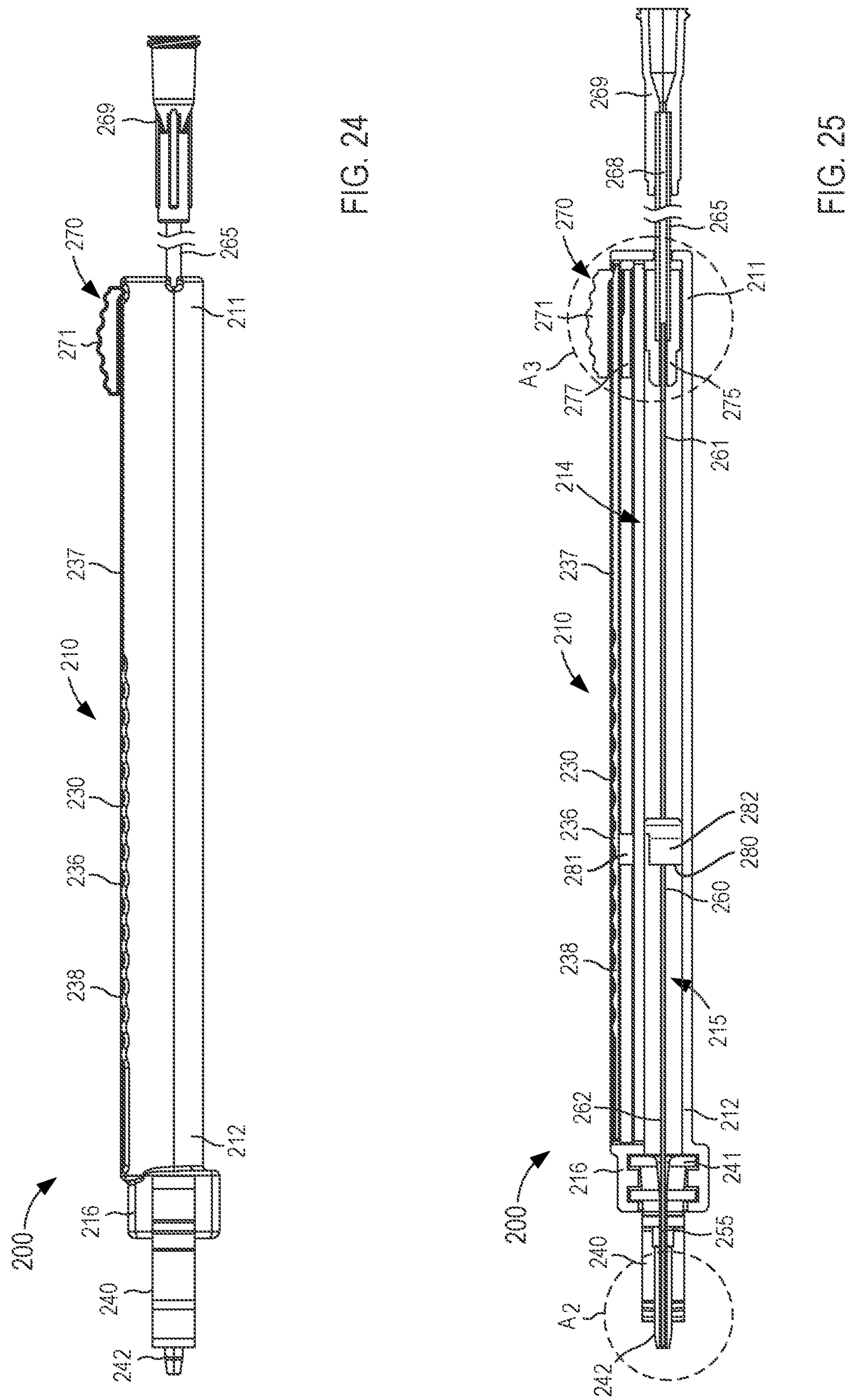
FIG. 24 is a side view of the inventive fluid transfer device of FIG. 1 in the first configuration.
FIG. 25 is a cross-sectional view of the inventive fluid transfer device in the first configuration taken along the line 25-25 in FIG. 1.

The secondary catheter 265 has a proximal end portion 266 and a distal end portion 267 and defines a lumen 268 (see e.g., FIG. 25). A portion of the secondary catheter 265 is disposed within and extends through the opening 217 of the introducer 210, which can be collectively defined by the notches 224, 234 of the first member 220 and second member 230, respectively. As such, the proximal end portion 266 is at least partially disposed outside of the introducer 210 and the distal end portion 267 is at least partially disposed within the second portion 215 of the inner volume 213 defined by the introducer 210. As described above, the secondary catheter 265 can be moved within the opening 217 between a first position and a second position to selectively clamp, pinch, kink, bend, and/or otherwise deform a portion of the secondary catheter 265, which in turn, obstructs, pinches, kinks, closes, seals, etc. the lumen 268 of the secondary catheter 265. For example, the first position can be associated and/or aligned with a first portion of the opening 217 having a larger perimeter and/or diameter than a perimeter and/or diameter of a second portion of the opening 217 associated and/or aligned with the second position. Thus, a user can manipulate the secondary catheter 265 to occlude the lumen 268 of the secondary catheter 265, thereby limiting, restricting, and/or substantially preventing a flow of a fluid therethrough.

As shown in FIG. 14, the proximal end portion 266 of the secondary catheter 265 is coupled to and/or otherwise includes a coupler 269. The coupler 269 is configured to physically and fluidically couple the secondary catheter 265 to any suitable device such as, for example, a fluid reservoir, fluid source, syringe, evacuated container holder (e.g., having a sheathed needle or configured to be coupled to a sheathed needle), pump, and/or the like. The distal end portion 267 of the secondary catheter 265 is at least partially disposed within the second portion 215 of the inner volume 213 defined by the introducer 210 and is coupled to the second portion 275 of the actuator 270. In some embodiments, the secondary catheter 265 can have a larger diameter than the catheter 260 such that the proximal end portion 261 of the catheter 260 is at least partially disposed within the lumen 268 defined by the secondary catheter 265 when the catheter 260 and the secondary catheter 265 are coupled to the second portion 275 of the actuator 270. Such an arrangement can, for example, reduce and/or substantially prevent leaks associated with fluid flowing between the catheter 260 and the secondary catheter 265. Such an arrangement can also limit, reduce, and/or substantially prevent hemolysis of a volume of blood as the volume of blood flows through the catheter 260 and the secondary catheter 265. In this manner, when the coupler 269 is coupled to a fluid reservoir, fluid source, syringe, evacuated container, pump, etc., the secondary catheter 265 establishes fluid communication between the reservoir, source, pump, etc. and the catheter 260.

As shown in FIGS. 3, 19-24, 25, 31, and 32, the catheter support 280 includes a bracket portion 281 and a hub portion 282. The bracket portion 281 of the catheter support 280 is at least partially disposed within the first portion 214 of the inner volume 213 defined by the introducer 210 and the hub portion 282 of the catheter support 280 is disposed within the second portion 215 of the inner volume 213.

The bracket portion 281 of the catheter support 280 may optionally include an engagement member 284. The arrangement of the catheter support 280 is such that the engagement member 284 is disposed outside of the introducer 210 while the rest of the bracket portion 281 is within the first portion 214 of the inner volume 213 of the introducer 210. As such, the engagement member 284 can be engaged and/or manipulated by a user, for example, by a finger or thumb of the user, to move the catheter support 280 relative to the introducer 210. The engagement member 284 may include a set of ridges and/or any suitable surface finish that can, for example, increase the ergonomic catheter support of the catheter support 280 and/or fluid transfer device 200.

The engagement member 284 may optionally have any of the features described above with respect to the engagement member 272 of the actuator 270 including, but not limited to, a tab that interacts with the set of ribs 236 on the outer surface of the second member 230 of the introducer 210.

The hub portion 282 has a cross-sectional shape that is based at least in part on a cross-sectional shape of the second portion 215 of the inner volume 213 defined by the introducer 210, for example, at least a partially circular cross-sectional shape. In this manner, the inner surface 223 of the first member 220 and the inner surface 233 of the second member 230 can support and/or guide the hub portion 282 of the catheter support 280 as the catheter support 280 is moved relative to the introducer 210.

The hub portion 282 defines a passageway 285 having a proximal opening 287 on the proximal end of the hub portion 282 and a distal opening 288 on the distal end of the hub portion 282. The passageway 285 is sized and shaped to allow the catheter 260 to freely pass through the passageway 285 while being contained to prevent excessive movement of the catheter 286 within the second portion 215 of the inner volume 213 of the introducer 210. The passageway 285 may be substantially cylindrical having a circular cross section.

The passageway 285 may comprise two portions with a proximal portion 289 adjacent to and in fluid communication with the proximal opening 287 and a distal portion 290 adjacent to and in fluid communication with the distal opening 288. The proximal portion 289 of the passageway 285 may be sized and shaped to receive at least a portion of the second portion 275 of the actuator 270. For example, the proximal opening 287 may be larger than the distal opening 288. The distal portion 290 of the passageway 285 may be substantially cylindrical having a circular cross-section with a diameter equal to a diameter of the distal opening 288. The proximal portion 289 may be substantially cone-shaped or funnel-shaped such that the proximal end of the proximal portion 289 of the passageway 285 has a diameter equal to a diameter of the proximal opening 287 and the diameter of the proximal portion 289 of the passageway 285 decreases until the distal end of the proximal portion 289 of the passageway 285 that is in fluid communication with the distal portion 290 of the passageway 285 has a diameter equal to the diameter of the distal portion 290 of the passageway 285.

Figure 21:
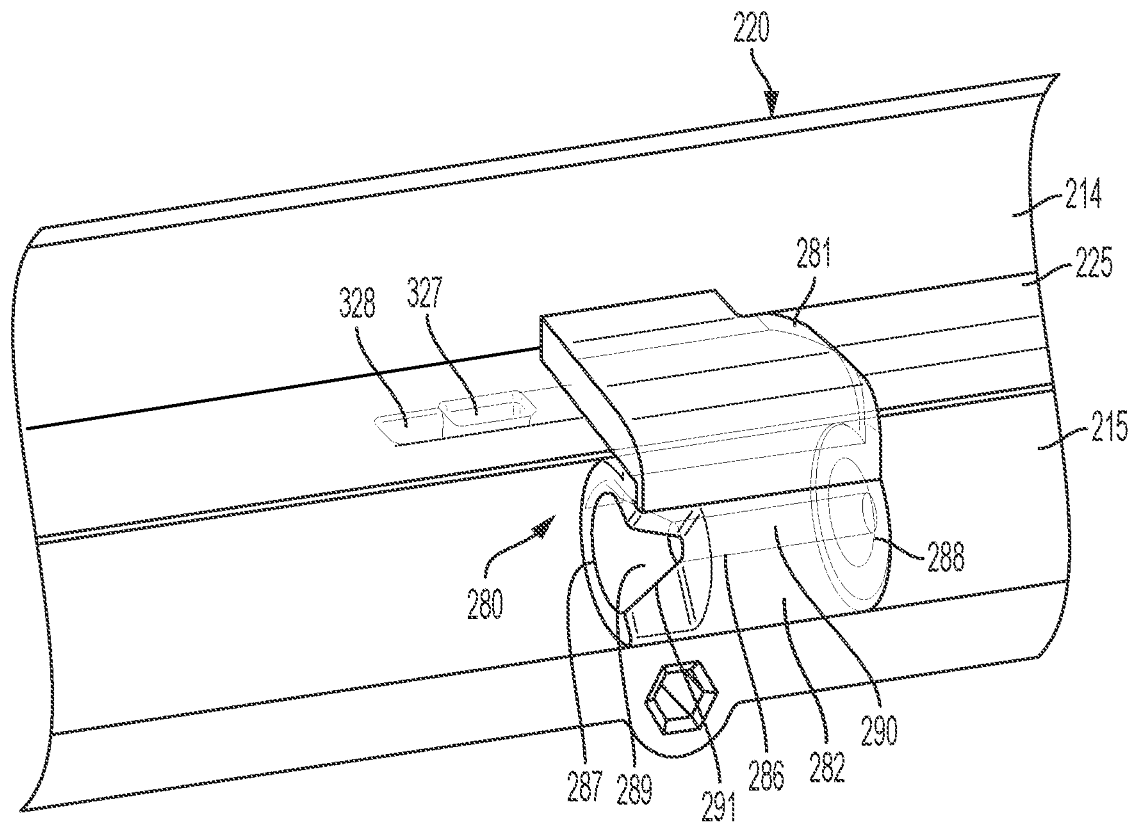
FIG. 21 is a perspective view of the catheter support inside the introducer of the inventive fluid transfer device of FIG. 1.
Figures 22A, 22B:
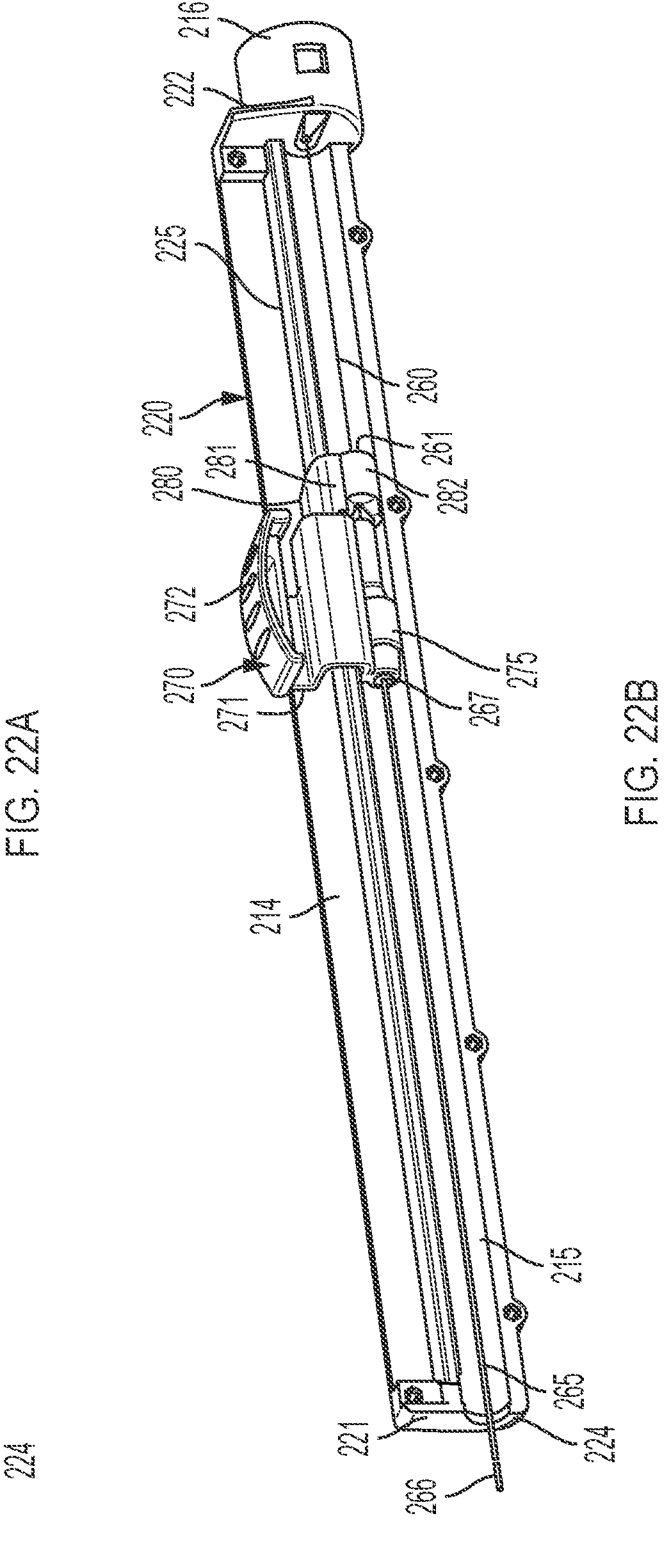
FIG. 22A is a side perspective view of the introducer of the inventive fluid transfer device of FIG. 1 in the first configuration with the second member of the introducer removed.
FIG. 22B is a side perspective view of the introducer of the inventive fluid transfer device of FIG. 1 as the inventive fluid transfer device is being transitioned from the first configuration to a second configuration with the second member of the introducer removed.
Figures 22C, 23:
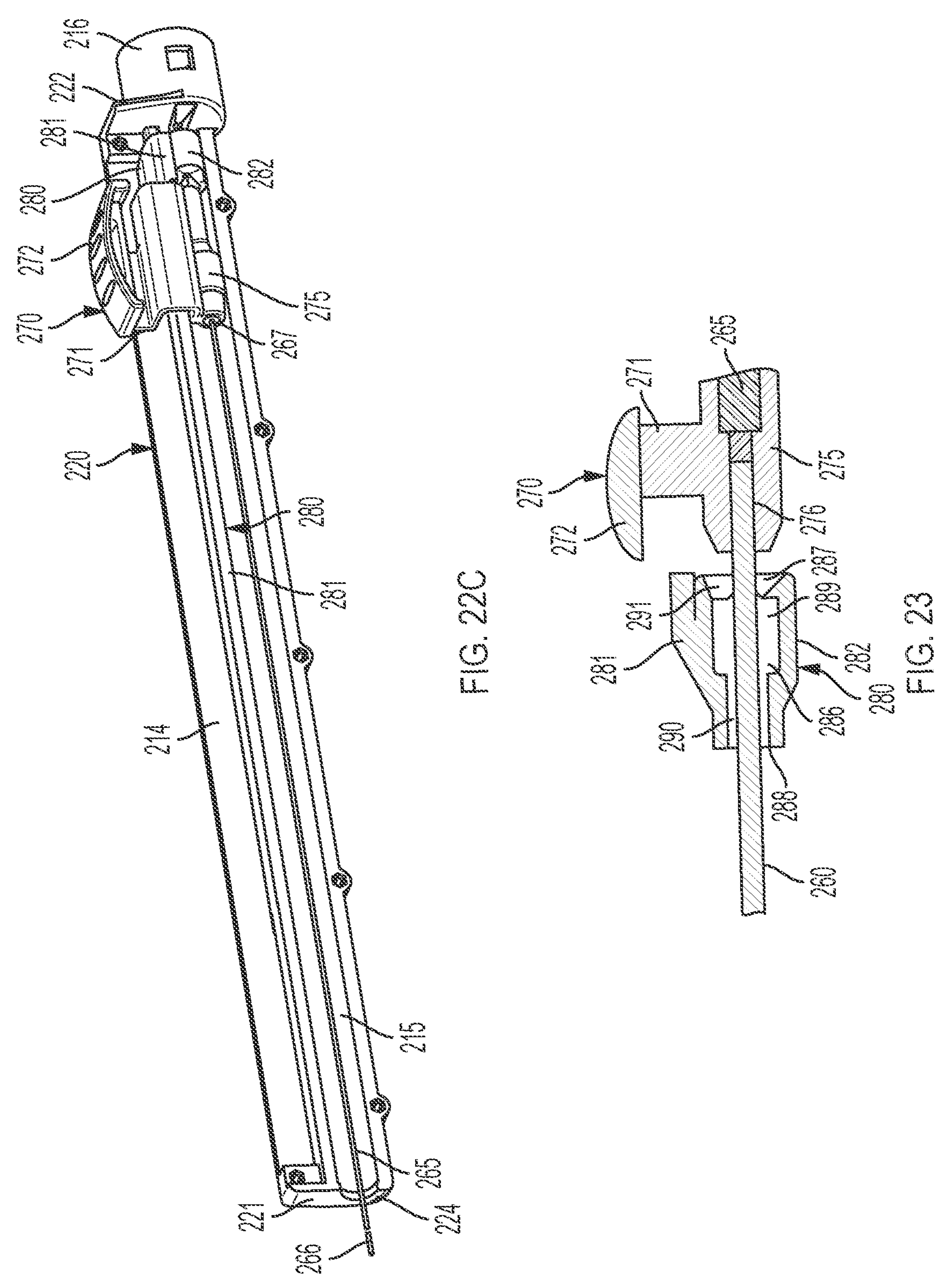
FIG. 22C is a side perspective view of the introducer of the inventive fluid transfer device of FIG. 1 in the second configuration with the second member of the introducer removed.
FIG. 23 is a side cross-sectional view of the actuator and the catheter support of the inventive fluid transfer device just prior to nesting of a portion of the actuator in a portion of the passageway of the catheter support.

As shown in FIG. 21, a notch 291 may be provided in the cone-shaped or funnel-shaped proximal portion 289 of the passageway 285.

Figure 19A:
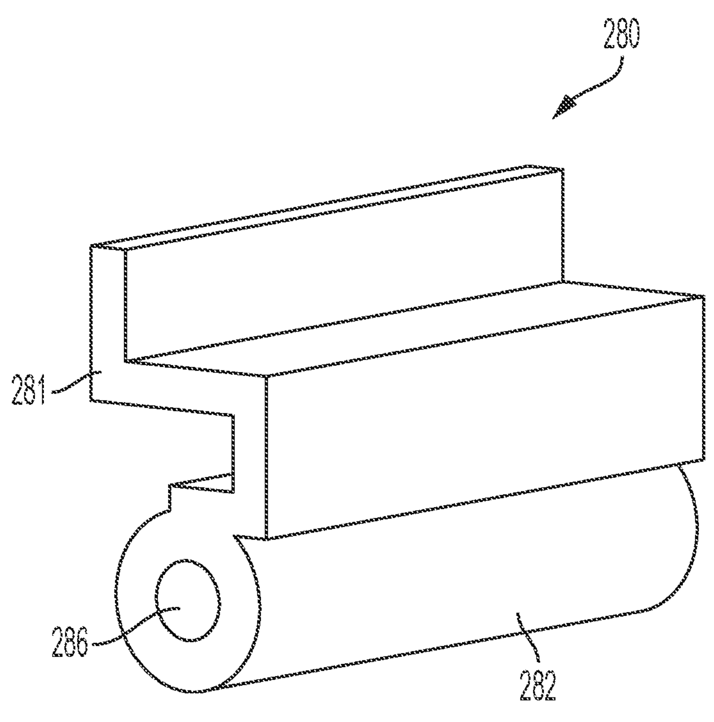
FIG. 19A is a perspective view of the catheter support shown in FIG. 5.
Figure 19B:
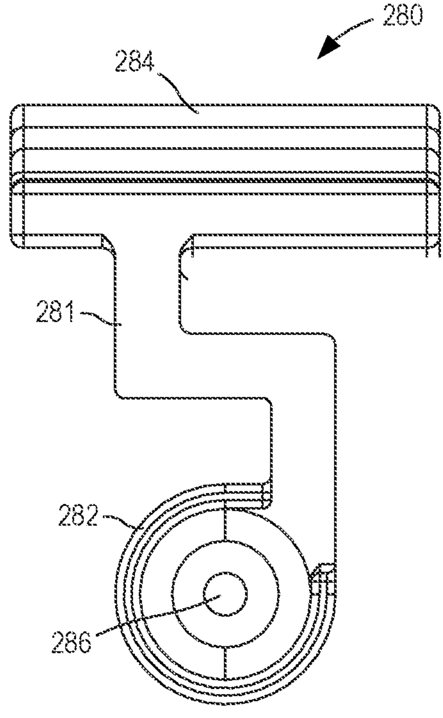
FIG. 19B is a front view of the catheter support shown in FIG. 5 with an optional engagement member.
Figure 20:
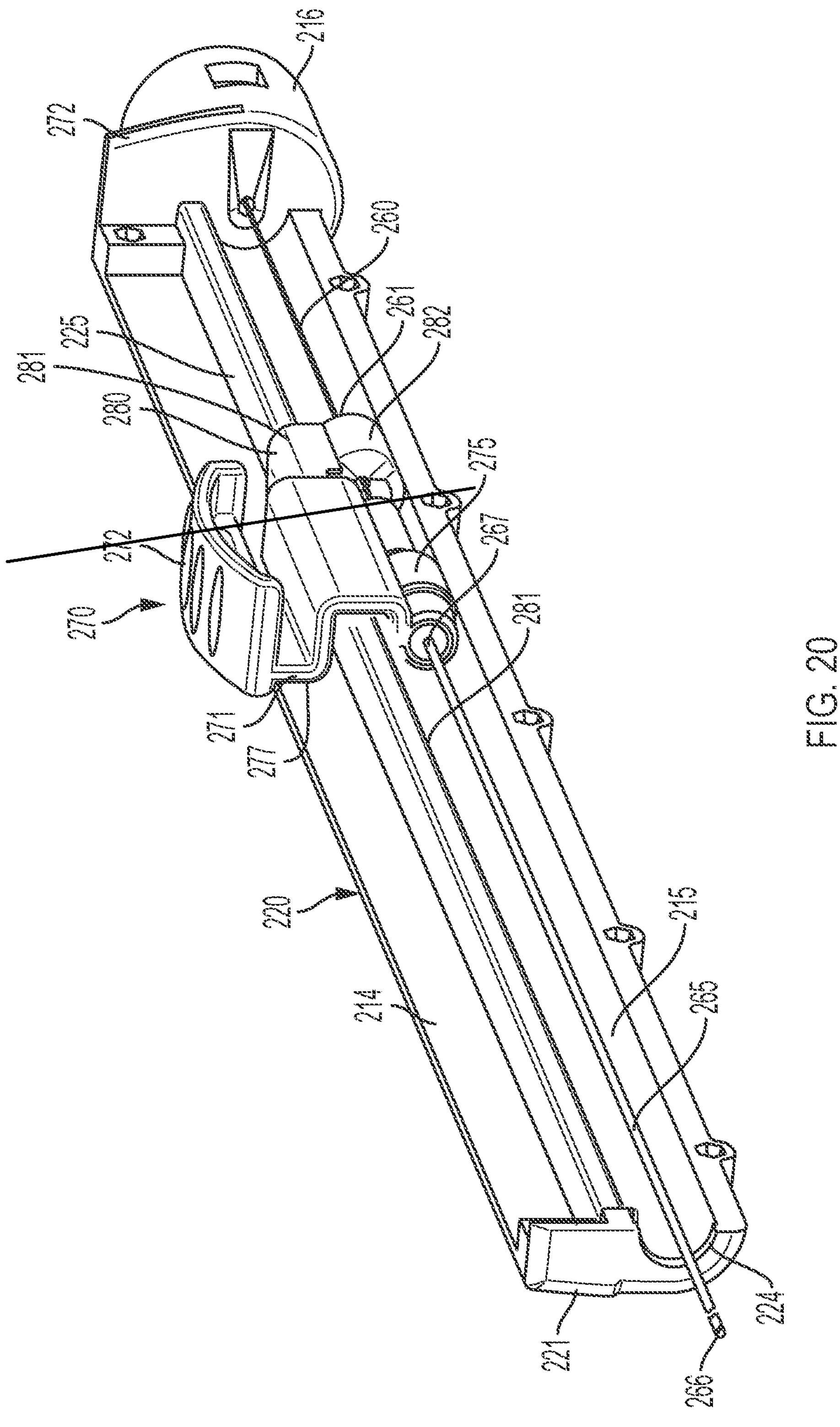
FIG. 20 is a side perspective view of the introducer of the inventive fluid transfer device of FIG. 1 with the second member of the introducer removed.

As shown in FIGS. 19A and 19B, the bracket portion 281 may have a tortuous cross-sectional shape that is based at least in part on the tortuous cross-sectional shape of the inner volume 213 of the introducer 210. In this manner, the bracket portion 281 of the catheter support 280 can define an axis that is parallel to but offset from an axis defined by the hub portion 282 of the catheter support 280. For example, the bracket portion 281 can have a substantially S-shaped or an at least partially S-shaped cross-sectional shape, or the bracket portion 281 can form dogleg shape or the like. The tortuous cross-sectional shape of the bracket portion 281 and thus, the catheter support 280, may be such that the hub portion 275 of the catheter support 280 cannot be viewed via the first portion 214 of the inner volume 213 and is out of the line of sight of the first portion 214 of the inner volume 213 defined by the introducer 210. The catheter support 280 may have an overall outer shape that is substantially the same as the actuator.

At least a portion of the bracket portion 281 of the catheter support 280 has a profile corresponding to an outer surface of the flange 225 provided on the inner surface of the introducer 210, such that the bracket portion 281 fits over and at least partially covers the flange 225 and is movable with respect to the introducer 210 in a direction from the proximal end portion 211 of the introducer 210 to the distal end portion 212 of the introducer 210 and vice versa along the flange 225. When the catheter support 280 is moved with respect to the introducer 210, the bracket portion 281 moves within the first portion 214 of the inner volume 213, and the hub portion 282 moves within the second portion 215 of the inner volume 213.

The opening 276 of the actuator 270 and the passageway 285 of the catheter support 280 may be coaxial.

The catheter 260 is coupled with the second portion 275 of the actuator 270 and extends to the distal end portion 212 of the introducer 210. Without the catheter support 280, the length of the catheter 260 extending this distance would be unsupported. The force at which a catheter 260 buckles is inversely proportional to the effective length squared. Thus, as the effective length of the catheter 260 increases, the buckling force decreases making the catheter less resistant to buckling. This catheter support 280 supports the catheter 260, thereby shortening the effective length of the catheter 280, increasing the force required to buckle the catheter 260, and decreasing the tendency of the catheter 260 to buckle.

The hub portion 282 of the catheter support 280 is positioned between the actuator 270 and the distal end portion 212 of the introducer 210 and the catheter 260 passes through the passageway 285 of the hub of the hub portion 282 such that the hub portion 282 divides the unsupported length of the catheter 260 into two smaller portions that are more resistant to bending, kinking, flexing, and/or deformation.

Figure 26:
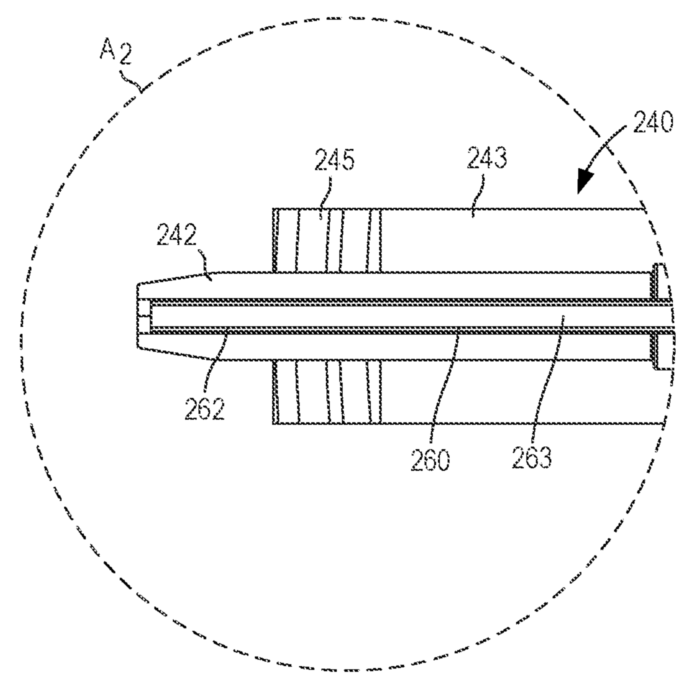
FIG. 26 is an enlarged cross-sectional view of a portion of the inventive fluid transfer device identified by the region A2 in FIG. 25.
Figure 27:
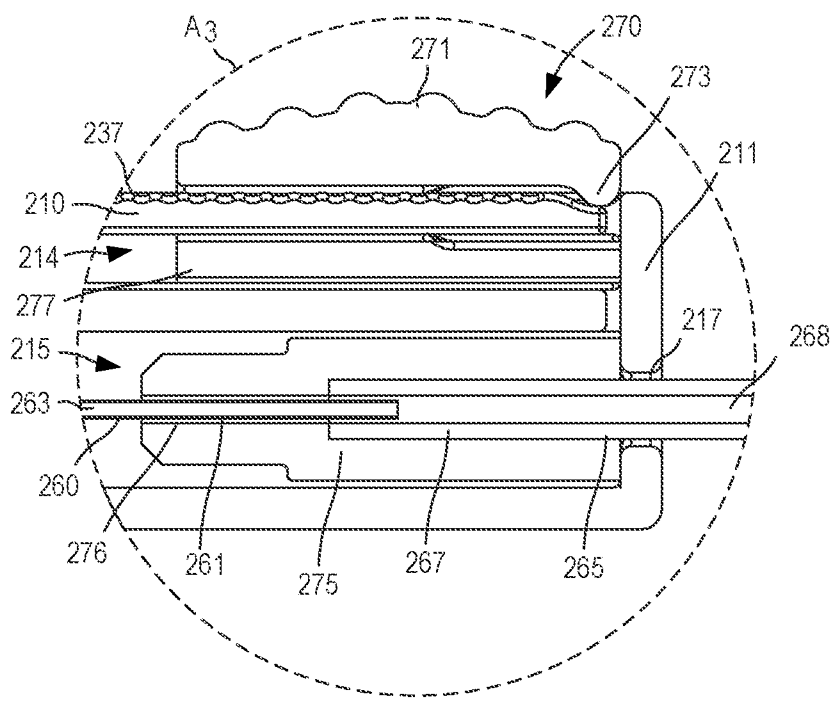
FIG. 27 is an enlarged cross-sectional view of a portion of the inventive fluid transfer device identified by the region A3 in FIG. 25.
Figures 28, 29:
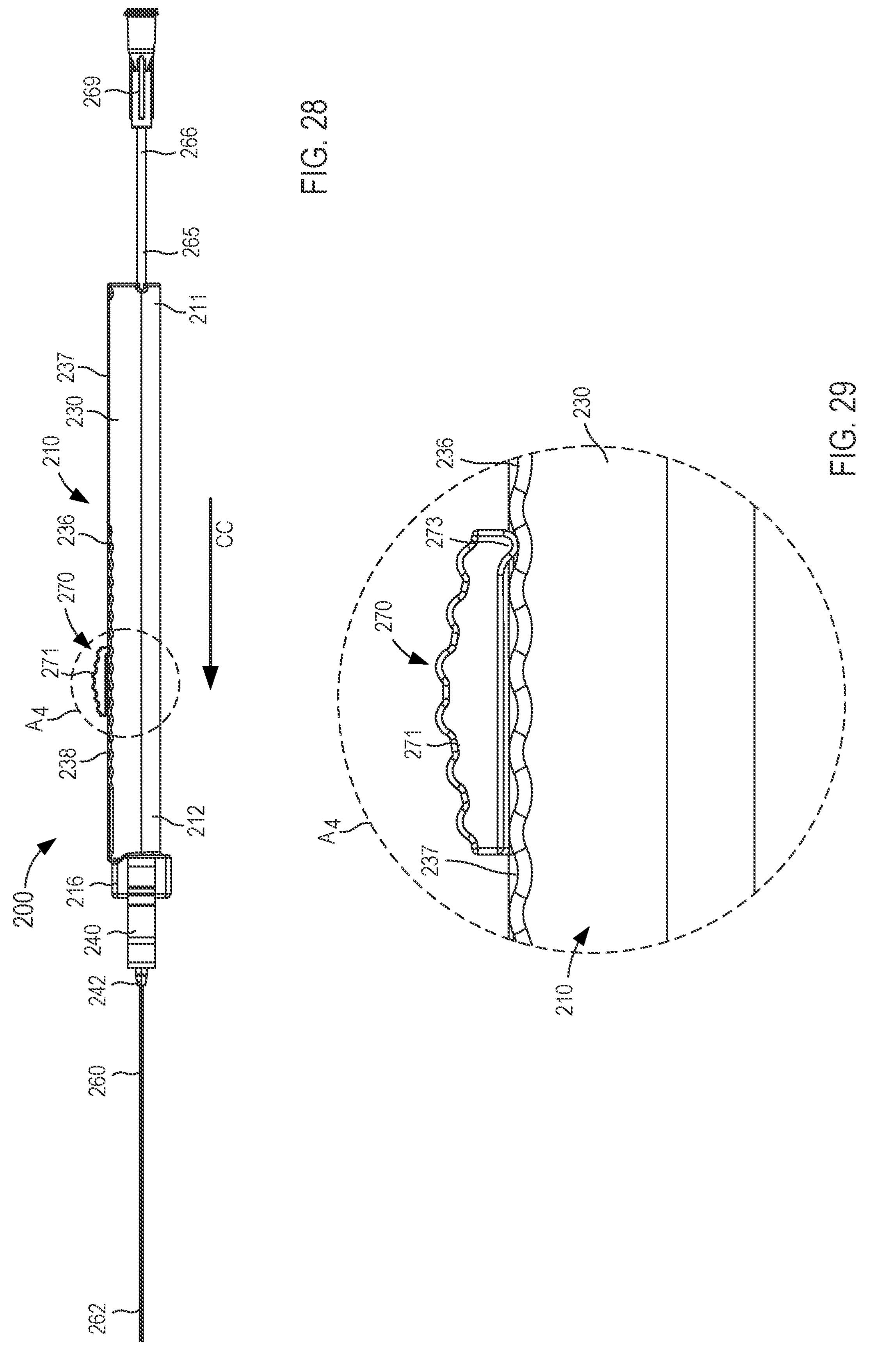
FIG. 28 is a side view of the inventive fluid transfer device of FIG. 1 as the inventive fluid transfer device is being transitioned from the first configuration to a second configuration.
FIG. 29 is an enlarged view of a portion of the inventive fluid transfer device identified by the region A4 in FIG. 28.
Figure 30:
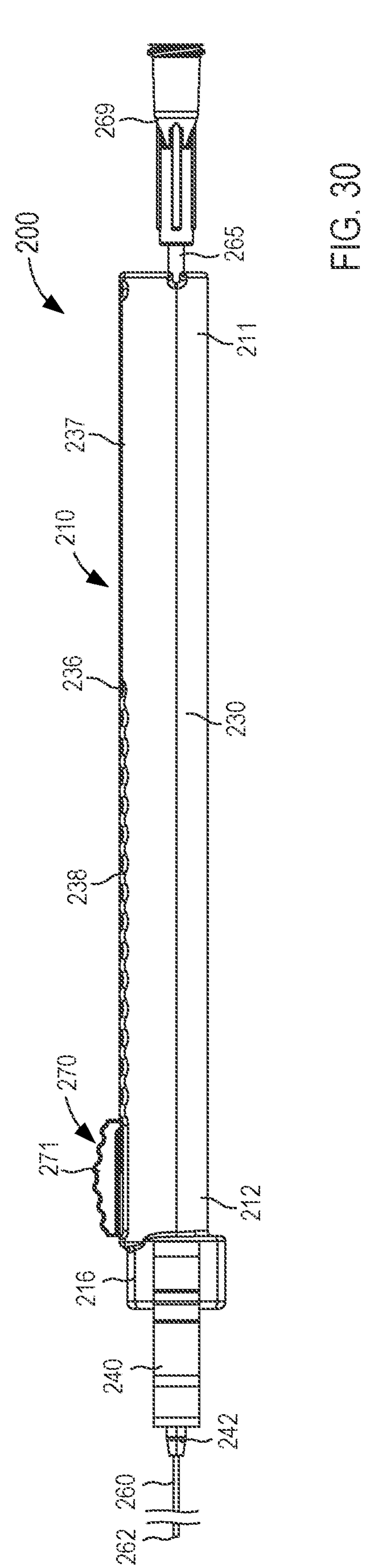
FIG. 30 is a side view of the inventive fluid transfer device of FIG. 1 in the second configuration.
Figure 31:
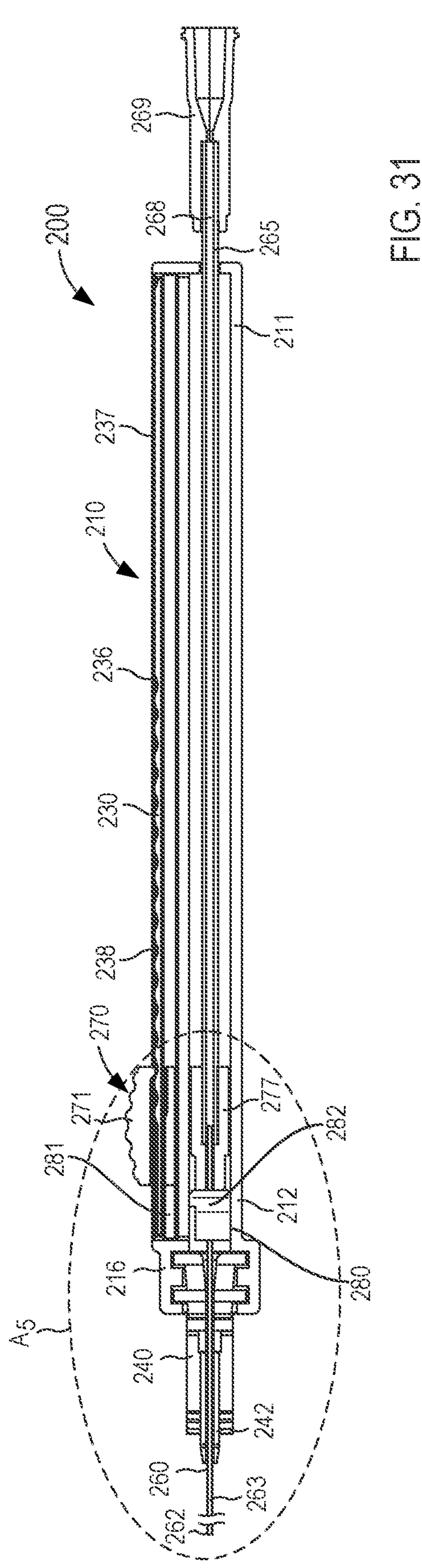
FIG. 31 is a cross-sectional view of the inventive fluid transfer device in the second configuration taken along the line 25-25 in FIG. 1.
Figure 32:
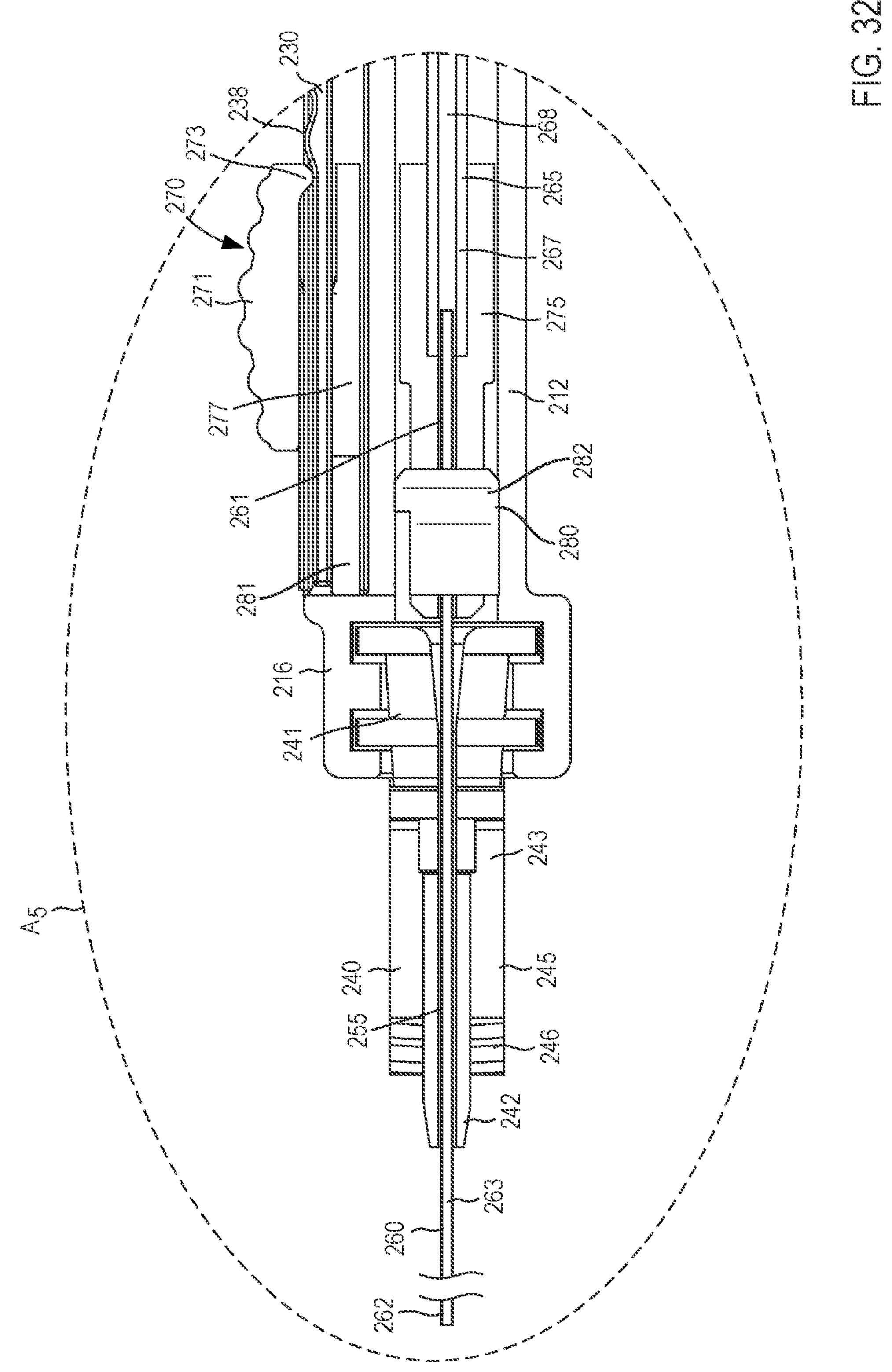
FIG. 32 is an enlarged cross-sectional view of a portion of the inventive fluid transfer device identified by the region A5 in FIG. 31.

Referring now to FIGS. 22-32, the fluid transfer device 200 can be in a first configuration prior to use and can be transitioned by a user, for example, a doctor, physician, nurse, technician, phlebotomist, and the like, from the first configuration (FIGS. 22A and 24-27) to a second configuration (FIGS. 22C and 30-32) to dispose at least the distal end portion 262 of the catheter 260 in a distal position relative to the introducer 210, for example, within an indwelling PIV (not shown) or distal to the indwelling PIV. The fluid transfer device 200 is in the first configuration when the catheter 260 is disposed in the first position within the introducer 210. Substantially the entire catheter 260 may be disposed within the introducer 210 when the catheter 260 is in the first position. The introducer 210 can include a seal or the like (as described above) that can substantially seal the distal end portion 212 of the introducer 210 to isolate the catheter 260 within the second portion 215 of the inner volume 213. Alternatively, as shown in FIGS. 25 and 26, the catheter 260 may be disposed within the introducer 210 and the lock 240 when the catheter 260 is in the first position. While the seal is described above as being included in the distal end portion 212 of the introducer 210, in other embodiments, the lock 240 can include a seal or the like that can form a substantially fluid tight seal with an inner surface of the lock 240 that defines the lumen 255. Thus, a seal disposed within the lock 240 can isolate the catheter 260 within the second portion 215 of the inner volume 213. However, the introducer 210 and/or the lock 240 need not include a seal. For example, a PIV and/or an adapter, for example, an extension set coupled to the PIV can include a seal that is transitioned from a closed configuration to an open configuration when the lock 240 is coupled thereto. Although not shown, the catheter 260 may be disposed within a flexible sheath or the like that can maintain the catheter 260 in a substantially sterile environment while the catheter 260 is in the first position, for example, in embodiments in which the introducer 210 and/or lock 240 do not include a seal.

When the fluid transfer device 200 is in the first configuration, the actuator 270 is disposed in a proximal position and the catheter support 280 is disposed in an intermediate position between the actuator 270 and the distal end portion 212 of the introducer 210, as shown in FIG. 23A and 25. In some embodiments, the tab 273 of the first portion 271 of the actuator 270 can be disposed within a recess or detent or otherwise in contact with a proximal most rib configured to temporarily and releasably maintain the actuator 270 in the proximal position until a force is exerted by the user to move the actuator 270 in the distal direction.

The proximal end portion 261 of the catheter 260 is coupled to the second portion 275 of the actuator 270, the catheter 260 extends through the second portion 215 of the inner volume 213 of the introducer 210 and through the passageway 285 of the hub portion 282, and the distal end portion 262 of the catheter 260 is received in the lumen of the coupler 216 and/or the lumen 255 of the lock 240.

The initial, pre-use position of the catheter support 280 may be set such that, in the first configuration, the position of the hub portion 272 along the unsupported portion of the catheter 260 extending from the second portion 275 of the actuator 270 to the distal end portion 212 of the introducer 210 is at the center point of the unsupported portion of the catheter or may be offset from the center point of the unsupported length of the catheter 260. For example, in the first configuration, the hub portion 282 of the catheter support 280 may be located in a position corresponding to a position of the actuator 270 when the advancement of the distal end portion 262 of the catheter 260 into the PIV meets resistance requiring additional force to be provided to the actuator 270 to further advance the catheter 260. For example, the position of the hub portion 282 of the catheter support 280 may correspond to the position of the actuator 270 corresponding to the advancement of the distal end portion 262 of the catheter 260 to a point at which the distal end portion 262 encounters a region where the catheter 260 must turn a corner to pass through an S-curve, for example, the area where the catheter 260 enters the skin, curves in an upward direction, and curves again to pass along the vein. As described above, a portion of the secondary catheter 265 is disposed in the opening 217 defined by the introducer such that the distal end portion 267 of the secondary catheter 265 is at least partially disposed in the second portion 215 of the inner volume 213 and coupled to the second portion 275 of the actuator 270 while the proximal end portion 266 of the secondary catheter 265 is disposed outside of the introducer 210.

With the fluid transfer device 200 in the first configuration, the user can manipulate the fluid transfer device 200 to couple the lock 240 to an indwelling PIV and/or to an adapter coupled to the PIV, for example, an extension set or the like.

With the fluid transfer device 200 coupled to the PIV and/or adapter, the user can engage the engagement member 272 of the first portion 271 of the actuator 270 to move the actuator 270 relative to the introducer 210, which in turn, moves the catheter 260 from the first position disposed within the introducer 210 toward a second position in which the distal end portion 262 of the catheter 260 extends into and/or through the PIV. In this manner, the catheter 260 is moved through the second portion 215 of the inner volume 213, the passageway 285 of the hub portion 282 of the catheter support 280, and the lumen 255 of the lock 240 and at least the distal end portion 262 of the catheter 260 is disposed outside of and distal to the lock 240, as indicated by the arrow CC in FIG. 28.

After partial movement of the actuator 270 in the distal direction and partial advancement of the catheter 260 towards the second position, the actuator 270 contacts the hub portion 282 of the catheter support 280. The distal end of the second portion 275 of the actuator 270 may abut the proximal end of the hub portion 282 or may be sized and shaped to be at least partially received within the proximal portion 289 of the passageway 285 of the hub portion 282.

As the actuator 270 is advanced further in the distal direction, the actuator 270 pushes the hub portion 282 of the catheter support 280 in the distal direction and the catheter support 280 is advanced in the second portion 215 of the inner volume 213 of the introducer 210 until the catheter support 280 abuts the distal wall of the introducer 210.

As described above, the arrangement of the actuator 270 and the introducer 210 is such that advancing the actuator 270 relative to the introducer 210 advances the tab 273 along the outer surface 235 and more specifically, the set of ribs 236 of the second member 230 of the introducer 210. As shown, for example, in FIG. 27, the tab 273 is in contact with the set of ribs 236, which can produce a vibration of the actuator 270 as the actuator 270 is moved relative to the introducer 210. In some instances, the vibration of the actuator 270 can produce, for example, a haptic, tactile, and/or audible output that can provide an indication associated with a position of the distal end portion 262 of the catheter 260 relative to the introducer 210, lock 240, and/or PIV. For example, the tab 273 of the actuator 270 and the set of ribs 236 can collectively produce a "click" sound as the tab 273 moves past each rib, the introducer 210 can include indicia or the like that can indicate to the user the relative position of the distal end portion 262 of the catheter 260, or the amount of times the actuator 270 has vibrated due to being moved relative to the number of ribs can be associated with and/or otherwise provide an indication of the relative position of the distal end portion 262 of the catheter 260.

In some instances, the user can stop moving the actuator 270 relative to the introducer 210 based on the haptic, tactile, and/or audible output indicating a desired placement of the distal end portion 262 of the catheter 260 relative to the PIV, such that the catheter 260 is placed in the second position prior to the actuator 270 being advanced to a distal most position. As described in further detail herein, the catheter 260 is disposed in the second position when the distal end portion 262 of the catheter 260 is placed in a desired position relative to a distal end portion of the PIV. For example, a distal surface of the catheter 260 can be substantially flush with a distal end of the PIV, the distal surface of the catheter 260 can extend a predetermined distance beyond the distal end of the PIV, or the distal surface of the catheter 260 can be disposed within the PIV proximal to the distal end of the PIV when the catheter 260 is in the second position.

As shown in FIGS. 22C and 30-32, in some instances, the catheter 260 may be in the second position when the actuator 270 is in a distal most position. In this manner, the distal surface of the catheter 260 is positioned within the vein at a predetermined distance beyond the distal surface of the PIV. In some instances, placing the distal surface of the catheter 260 the predetermined and/or desired distance from the distal surface of the PIV can place the distal surface of the catheter 260 in a position within a vein that is substantially free from debris, for example, fibrin/blood clots, otherwise surrounding the distal surface of the PIV.

In some instances, the indwelling PIV can substantially occlude at least a portion of the vein within which the PIV is disposed. As such, PIVs are often suited for delivering a fluid rather than aspirating blood. The venous system, however, is a capacitance system and thus, reroutes blood flow through a different vein by forming a bypass around the occlusion or substantial occlusion. Moreover, the alternate venous structure typically rejoins the vein in which the PIV is disposed at a given distance downstream of the PIV and thus, delivers at least a portion of the flow of blood that would otherwise be flowing through the vein in which the PIV is disposed. Similarly, veins typically have many branch vessels coupled thereto that similarly deliver a flow of blood to the vein within which the PIV is disposed.

As such, the predetermined and/or desired distance between the distal surface of the catheter 260 and the distal surface of the PIV can be sufficient to place the distal surface of the catheter 260 downstream of one or more branch vessels in fluid communication with the vein within which the PIV is disposed, such that the distal surface of the catheter 260 can extend beyond the distal surface of the PIV and at least one branch vessel is disposed between the distal surface of the catheter 260 and the distal surface of the PIV when the catheter 260 is in the second position. Therefore, with the lumen 263 of the catheter 260 extending through the proximal end portion 261 and the distal end portion 262 of the catheter 260, placing the distal surface of the catheter 260 the predetermined and/or desired distance from the distal surface of the PIV places the lumen 263 of the catheter 260 in fluid communication with a portion of the vein receiving a substantially unobstructed or unrestricted flow of blood, for example a portion of the vein unobstructed by the PIV and/or debris associated with the indwelling of the PIV.

The predetermined and/or desired distance can be about 0.0 millimeters when the distal surfaces are flush and up to about 100 millimeters (mm), for example, 10 mm to about 90 mm, about 20 mm to about 80 mm, about 30 mm to about 70 mm, about 30 mm to about 60 mm, or about 40 mm to about 50 mm. For example, the fluid transfer device 200 may be configured such that the actuator 270 moves about 95 mm along the introducer 210 to position the distal surface of the catheter 260 about 40 mm beyond the distal surface of the PIV to which the fluid transfer device 200 is coupled, the fluid transfer device 200 may be configured such that the actuator 270 moves about 47 mm along the introducer 210 to position the distal surface of the catheter 260 at about 20 mm beyond the distal surface of the PIV to which the fluid transfer device 200 is coupled, or the fluid transfer device 200 can have any suitable stroke length to position the distal surface of the catheter 260 at the predetermined and/or desired distance from the distal surface of the PIV.

Although the predetermined and/or desired distance is described above as being a positive distance, that is, the distal surface of the catheter 260 is distal to the distal surface of the PIV, the predetermined and/or desired distance can be associated with a negative distance in which the distal surface of the catheter 260 is in a proximal position relative to the distal surface of the PIV. For example, in some instances, the predetermined and/or desired distance can be about 0.0 mm when the distal surfaces are flush and up to about −50 mm, for example, about −10 mm to about −40 mm, or about −20 mm to about −30 mm. In some instances, the predetermined and/or desired distance can be less than −50 mm when the distal surface of the catheter 260 is more than 50 mm proximal to the distal surface of the PIV. The catheter 260 may be placed in the second position such that the distal end portion 262 of the catheter 260 remains within the PIV in a position distal to, for example, a kink or the like. For example, indwelling PIVs can have one or more portions that are kinked such as a portion of the PIV where the peripheral intravenous catheter couples to a hub. In such instances, the predetermined and/or desired distance can be such that the distal surface of the catheter 260 is distal to the portion of the PIV that forms the kink, for example the position where the peripheral intravenous catheter couples to the hub. By placing the distal surface of the catheter 260 distal to the kinked portion of the PIV but remaining within the PIV a fluid flow path that is sufficiently unrestricted to allow blood to be aspirated through the catheter 260 can be formed.

With the catheter 260 in the second position and the fluid transfer device 200 in the second configuration shown, for example, as shown in FIGS. 22C and 30-32, the user can establish fluid communication between a fluid reservoir, fluid source, syringe, and/or the like and the catheter 260. For example, as described above, the user can physically and fluidically couple the coupler 269 of the secondary catheter 265 to a fluid reservoir, fluid source, syringe, and/or the like. Although described as establishing fluid communication between the catheter 260 and the fluid reservoir or fluid source after placing the catheter 260 in the second position, the user can establish fluid communication between the catheter 260 and the fluid reservoir or fluid source prior to moving the actuator 270 relative to the introducer 210. With the catheter 260 in fluid communication with the fluid reservoir and/or fluid source, the fluid transfer device 200 can then transfer a fluid from the patient or transfer a fluid to the patient via the catheter 260 extending through and beyond the PIV. For example, the user can physically and fluidically couple the fluid transfer device 200 to a fluid reservoir, evacuated container, syringe, and/or the like and then can aspirate a volume of blood from the vein based at least in part on disposing the distal surface of the catheter 260 at the predetermined and/or desired distance beyond the distal surface of the PIV.

In other instances, the user can physically and fluidically couple the fluid transfer device 200 to a fluid source or the like and then can deliver a volume of fluid from the fluid source to a portion of the vein at a position downstream of the PIV that receives a substantially uninhibited and/or unrestricted flow of blood. Disposing the distal surface of the catheter 260 at the predetermined and/or desired distance beyond the distal surface of the PIV can reduce potential harm associated with infusion of caustic drugs. By positioning the distal surface of the catheter 260 within a portion of the vein receiving a flow of blood that would otherwise be inhibited and/or restricted by the indwelling PIV, the caustic drug can be entrained in the flow of blood and delivered to the target location. As such, a volume of the caustic drug is not retained within the debris or otherwise disposed in a position within the vein receiving little blood flow.

Once a desired amount of blood has been collected and/or once a desired volume of a drug has been delivered to the patient, the user can move the actuator 270 in the proximal direction, thereby placing the fluid transfer device 200 in a third (used) configuration. The catheter support 280 may remain stationary at the distal end portion 212 of the introducer 210 or may be coupled to the actuator 270 such that the movement of the actuator 270 in the proximal direction pulls the catheter support 280 in the proximal direction.

If the catheter support 280 is not coupled to the actuator 270 and the catheter support 280 includes an engagement member 284, the engagement member 284 may be engaged and/or manipulated by the user to manually move the catheter support 280 in the proximal direction.

When the actuator 270 is coupled to the catheter support 280, the opening 276 of the actuator 270 and the passageway 285 of the catheter support 280 are coaxial.

The actuator 270 may be coupled to the catheter support 280 when the actuator 270 and the catheter support 280 first make contact when both are in the intermediate position, or the actuator 270 may be coupled to the catheter support 280 when the catheter support 280 abuts the distal end wall of the introducer 210.

Any suitable coupling may be provided to couple the actuator 270 to the catheter support 280. For example, when the actuator 270 contacts the catheter support 280, a portion of the second portion 275 of the actuator 270 may be received in the proximal portion 289 of the passageway 285 of the hub portion 282 of the catheter support 280. For example, the portion of the second portion 275 of the actuator 270 may be coupled to the hub portion 282 of the catheter support 280 by an interference fit, snap fit, or friction fit between an inner surface of the hub portion 282 of the catheter support 280 and an outer surface of the second portion 275 of the actuator 270.

Figure 33A:
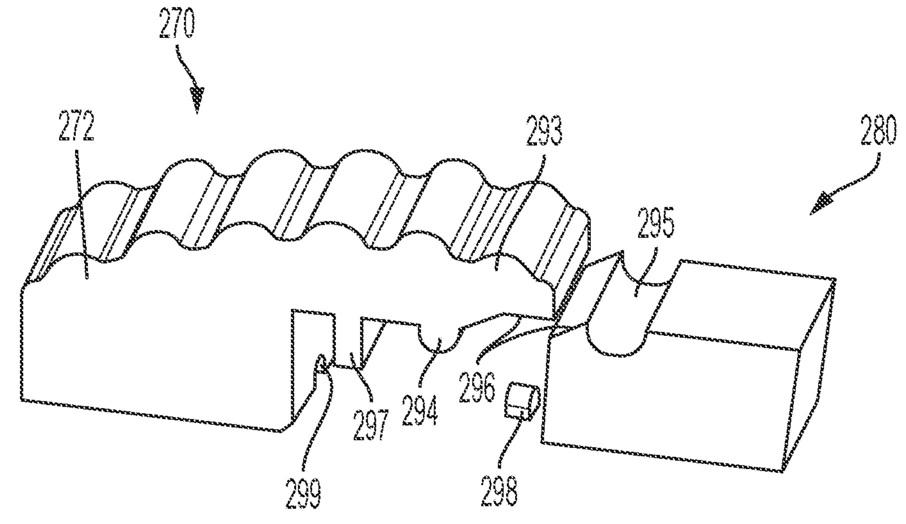
FIG. 33A is a perspective view of a configuration for coupling the actuator to the catheter support.

In another example, as shown in FIG. 33A, one of a protrusion and a recess may be provided on a surface of a flexible beam 293 at the distal end of the engagement member 272 of the actuator 270 and the other of a protrusion and a recess may be provided on a surface of the bracket portion 281 of the catheter support 280 exposed in the slot 218 of the introducer 210 or on the optional engagement member 284 of the catheter support 280. For example, as shown in FIG. 33, the protrusion 294 may be provided on the bottom surface of the flexible beam 293 and the recess 295 may be provided on the top of the catheter support 280. Alternatively, the recess may be provided on the side or another surface of the catheter support 280. When the catheter support 280 abuts the distal end wall of the introducer 210, and the user continues to move the actuator 270 in the distal direction, the flexible beam 293 is deflected upwardly a small amount such that the flexible beam 293 moves over the catheter support 280 and the protrusion 294 is received in the recess 295. Camming surfaces 296 may be provided on the distal end of the flexible beam 293 and/or the proximal end of the catheter support 280 to facilitate the flexing of the flexible beam 293.

A stop 297 may be provided on the flexible beam 293 distal to the protrusion 294. When the actuator 270 has been advanced such that the stop 297 abuts the catheter support 280, further advancement of the actuator 270 with respect to the catheter support 280 will be restricted to avoid disengagement of the protrusion 294 from the recess 295.

Figure 33B:
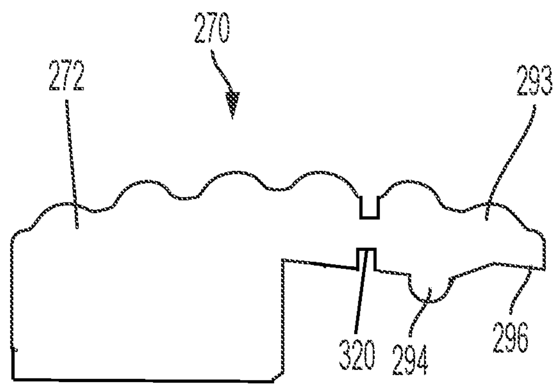
FIG. 33B is a cross-sectional view of the actuator of FIG. 33A including a hinge in the flexible beam.

As shown in FIG. 33B, the flexible beam 293 may optionally include a hinge 320 comprising a thinned region that allows tuning of the force required to couple and uncouple the actuator 270 and the catheter support 280.

Optionally, a retraction stop 298 to stop the proximal movement of the catheter support 280 may extend from the introducer 210, for example, the retraction stop 298 may extend upwardly from the flange 225 of the introducer 210 (FIG. 33). A groove 299 may be provided in the portion of the first portion 271 of the actuator 270 that slides along the flange 225 of the introducer 210 as the actuator 270 is moved to advance the catheter 260. No such groove is provided in the bracket portion 281 of the catheter support 280. When the coupled actuator 270 and catheter support 280 are moved in the proximal direction, the actuator 270 passes over the retraction stop 298 which is received in the groove 299, while the catheter support 280 abuts the retraction stop 298, stopping the proximal movement of the catheter support 280. The actuator 270 can then be moved further in the proximal direction while the catheter support 280 remains stationary. If the retraction stop 298 is provided in combination with the coupling described above as shown in FIG. 33, further force placed on the engagement member 272 of the actuator 270 will cause the flexible beam 293 to flex, disengaging the protrusion 294 from the recess 295 and the actuator 270 from the catheter support 280. The retraction stop 298 may be positioned to stop the catheter support 280 in the same position that the catheter support 280 was in when the catheter 260 was in the first position.

Alternatively, as shown in FIG. 21, the retraction stop may comprise a detent 327 extending with in a slot 328 in the introducer 210. The slot 328 may be provided in flange 225 provided on the inner surface of the introducer 210. The detent 327 engages the bracket portion 281 of the catheter support 280 to restrict movement of the catheter support 280. When the actuator 270 is moved in the proximal direction and abuts the catheter support 280, the proximal force placed on the catheter support 280 by the actuator 270 overcomes the force of the detent 327 on the catheter support 280 releasing the catheter support 280 from the detent 327, and the actuator 270 pushes the catheter support 280 in the proximal direction until the catheter support 280 abuts the distal end portion 212 of the introducer 210. If the actuator 270 is coupled to the catheter support 280, when the actuator 270 is moved in the proximal direction, pulling the catheter support 280 in the proximal direction, and the catheter support 280 encounters the detent 327, the proximal movement of the catheter support 280 is restricted.

Figure 33C:
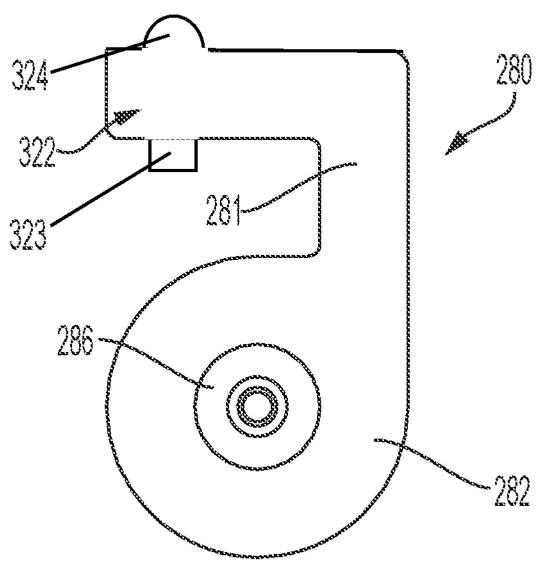
FIG. 33C is a cross-sectional view of an alternative configuration for the catheter support of FIG. 33A.
Figure 33D:
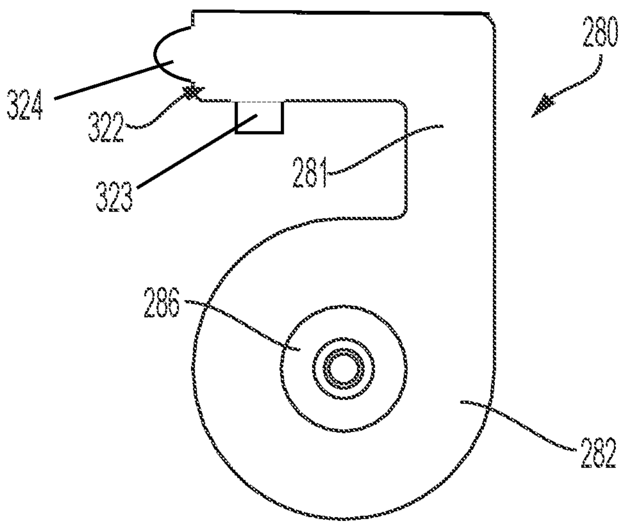
FIG. 33D is a cross-sectional view of another alternative configuration for the catheter support of FIG. 33A.

In another example, as shown in FIGS. 33C and 33D, instead of the recess 295, the catheter support may include releasable lock 322 that is engaged by the protrusion 294 on the flexible beam 293. The releasable lock 322 comprises a stop portion 323 and an engagement portion 324. The stop portion 323 extends from the catheter support 280 and is received in and moves along a groove in the introducer 210 when the catheter support 280 is moved with respect to the introducer 210. When the stop portion 323 abuts the proximal end of the groove, further proximal movement of the catheter support 280 is no longer possible. The engagement portion 324 of the releasable lock 322 may comprise a bulge that interacts with the protrusion 294 on the flexible beam 293 of the actuator 270. As shown in FIG. 33C, the stop portion 323 of the releasable lock 322 may extend from the bottom surface of the bracket portion 281 of the catheter support 280 and the engagement portion 324 of the releasable lock 322 may extend from the top surface of the bracket portion 281 of the catheter support 280. In this configuration, the stop portion 323 may ride in a groove on the flange 225 provided on the inner surface of the introducer 210. Alternatively, as shown in FIG. 33D, both the stop portion 323 of the releasable lock 322 may extend from the bottom surface of the bracket portion 281 of the catheter support 280 and the engagement portion 324 of the releasable lock 322 may extend laterally from the side of the bracket portion 281 of the catheter support 280.

When the actuator 270 is moved in the proximal direction and abuts the catheter support 280, the actuator 270 pushes the catheter support in the proximal direction until the catheter support 280 abuts the distal end portion 212 of the introducer 210. When the catheter support 280 abuts the distal end wall of the introducer 210, and the user continues to move the actuator 270 in the distal direction, the flexible beam 293 is deflected upwardly a small amount and the protrusion 294 is forced over the engagement portion 324 of the releasable lock 322. The surface of the protrusion 294 on the flexible beam 293 and/or the engagement portion 324 of the releasable lock 322 may be rounded and/or included camming surfaces to facilitate the movement of the protrusion 294 over the engagement portion 324. When the actuator 270 is then moved in the proximal direction, the engagement between the protrusion 294 and the engagement portion 324 of the releasable lock 322 allows the actuator 270 to pull the catheter support 280 in the proximal direction until the catheter support 280 abuts the proximal end of the groove stopping the advancement of the catheter support 280 in the proximal direction. When the user continues to move the actuator 270 in the proximal direction, the flexible beam 293 is deflected upwardly a small amount and the protrusion 294 is forced over the engagement portion 324 of the releasable lock 322, thereby uncoupling the actuator 270 from the catheter support.

Figure 34:
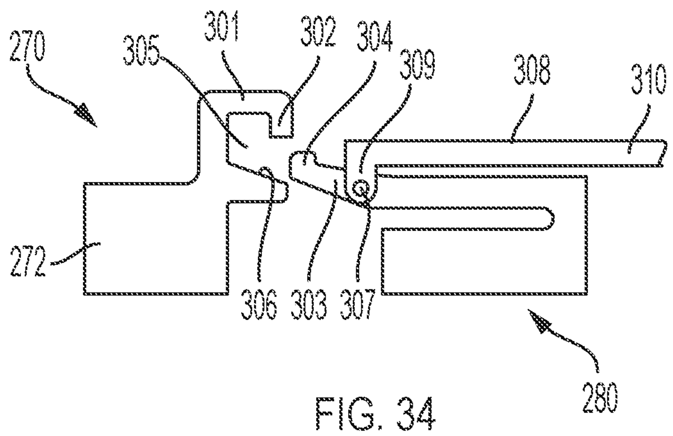
FIG. 34 is a side view of an alternative configuration for coupling the actuator to the catheter support.
Figure 35A:
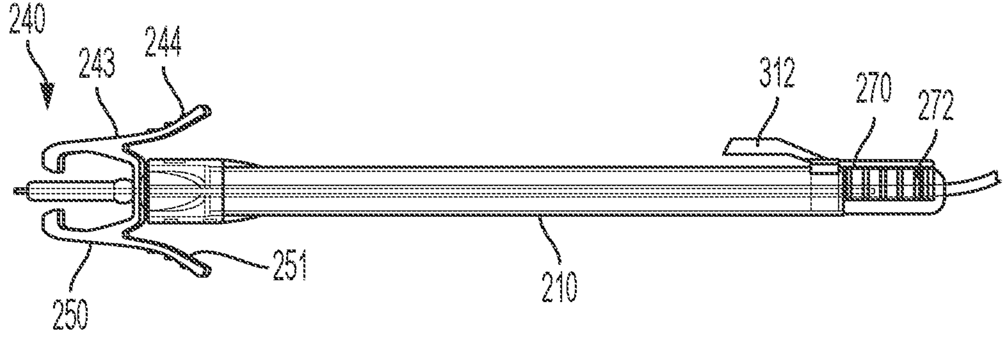
FIG. 35A is a top view of an inventive fluid transfer device in the first configuration, the fluid transfer device having a catheter support with a locking protrusion.
Figure 35B:
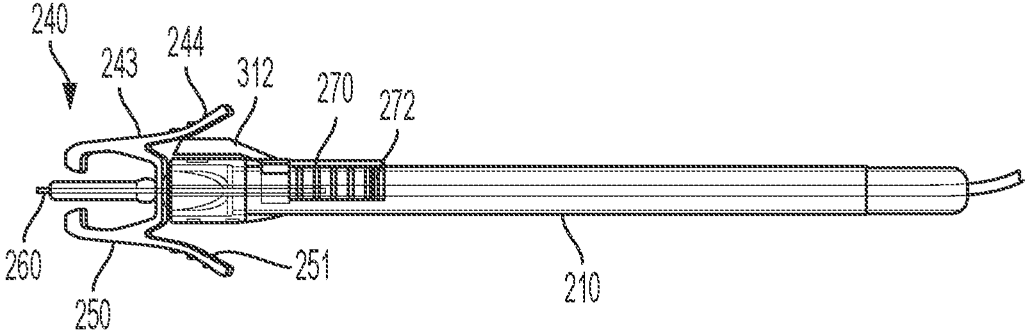
FIG. 35B is a top view of the inventive fluid transfer device of FIG. 35A in the second configuration.
Figure 36:
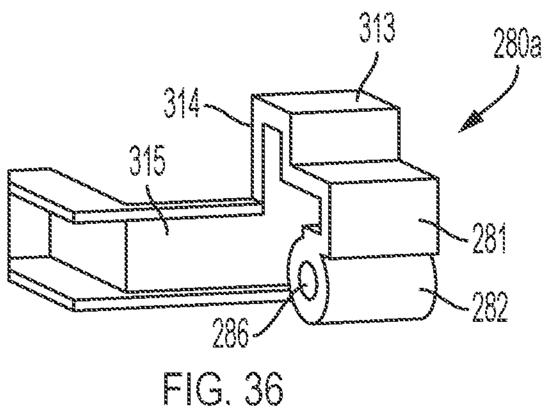
FIG. 36 is a perspective view of a catheter support with a locking protrusion.
Figure 37:
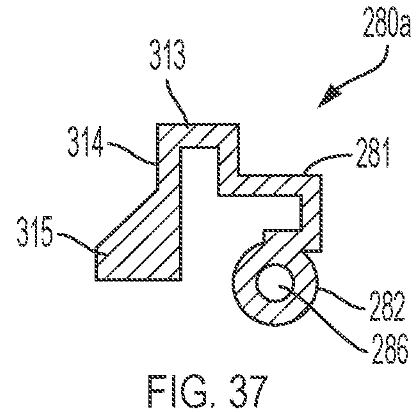
FIG. 37 is a cross-sectional view of the catheter support of FIG. 36.
Figure 38:
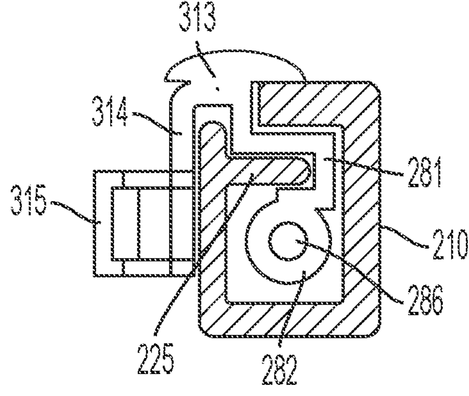
FIG. 38 is a cross-sectional view of the catheter support of FIG. 36 positioned in the introducer of an inventive fluid transfer device.

In another example, as shown in FIG. 34, an engagement protrusion 301 including a hook 302 may extend from a distal end of the engagement member 272 of the actuator 270, and a corresponding pivotable protrusion 303 having a hook 304 may extend from a proximal end of the catheter support 280. The engagement protrusion 301 on the actuator 270 defines a recess 305 for receiving the pivotable protrusion 303 of the catheter support 280. The recess 305 has a sloped bottom surface 306 closest to the engagement member 272 of the actuator 270. The pivotable protrusion 303 pivots around a pin 307 that rides in a cam slot 308 defined in the introducer 210. The cam slot 308 comprises two portions, a retention portion 309 and a movement portion 310. The retention portion 309 is provided at the proximal end of the movement portion 310 and forms a downward angle, for example, a right angle, with the movement portion 310. The retention portion 309 is located in a position corresponding to the desired position of the catheter support 280 when the catheter 260 is in the first position. The movement portion 310 extends from the retention portion 309 to the distal end portion 212 of the introducer 210.

When the actuator 270 is moved in a distal direction and abuts the catheter support 280, the pivotable protrusion 303 is received in the recess 305 defined by the engagement protrusion 301. The pivotable protrusion 303 is pivoted in a clockwise direction by the sloped bottom surface 306 of the recess 305. The hook 302 of the engagement protrusion 301 engages the hook 304 of the pivotable protrusion 303 and the sloped bottom surface 306 causes the pin 307 to transition from the retention portion 309 of the cam slot 308 into the movement portion 310 of the cam slot 308. Further distal movement of the actuator 270 moves the catheter support 280 in the distal direction with the pin 307 riding in the movement portion 310 of the cam slot 308.

When the coupled actuator 270 and catheter support 280 are moved in a proximal direction and the pin 307 reaches the proximal end of the movement portion 310 of the cam slot 308, the pin 307 will transition into the retention portion 309 of the cam slot 308 and the pivotable protrusion 309 will rotate in a counterclockwise direction disengaging the hook 304 of the pivotable protrusion 303 from the hook 302 of the engagement protrusion 301. The actuator 270 can then be moved further in the proximal direction while the catheter support 280 remains stationary.

In the third configuration, the catheter 260 can be disposed within the introducer 210, for example, distal to the seal or the like, and isolated therein. For example, the actuator 270 can be located in a proximal most position, in which the catheter 260 is in the first position. Moreover, once the actuator 270 and catheter 260 are in the desired position, the user can, manipulate the secondary catheter 265 within the opening 217 such that a surface of the introducer 210 that defines the smaller portion of the opening 217 contacts and clamps the secondary catheter 265. As such, the lumen 268 of the secondary catheter 265 can be substantially obstructed, occluded, blocked, pinched, etc., to limit and/or substantially prevent a flow of fluid therethrough. Clamping the secondary catheter 265 can reduce and/or substantially prevent fluid from leaking through the secondary catheter 265. The fluid transfer device 200 can then be decoupled from the fluid reservoir, fluid source, syringe, etc., and safely discarded.

As shown in FIGS. 35-38, the catheter support 280*a* may include at least one locking protrusion 312 extending outwardly from the catheter support 280*a*. The locking protrusion 312 is sized and shaped such that, when the fluid transfer device 300 is in the second configuration with the catheter support 280 at the distal end portion 212 of the introducer 210 and the catheter 260 introduced into the PIV, the locking protrusion 312 is received in the space between one of the arms 243, 250 of the lock 240 and the coupler 241 and blocks the first end portion 244, 251 of the arm 243, 250 of the lock 240 from being depressed and releasing the lock 240 from the PIV. The interference of the locking protrusion 312 with the release of the lock 240 requires the user to retract the catheter support 280 and the actuator 270, thereby retracting the catheter 260 from the PIV, prior to disconnecting the lock 240 from the PIV. This assures that the introducer 210 is not removed from the PIV while the catheter 260 is received within the PIV and possibly the vein of the patient.

The locking protrusion 312 may extend out of the slot 218 in the introducer 210 and include a first portion 313 extending outwardly in a lateral direction, a second portion 314 extending downwardly from the first portion 313, and a third portion 315 extending distally from the second portion 314, where the third portion 315 enters the space between one of the arms 243, 250 of the lock 240 and the coupler 241. The first portion 316 may be connected to the bracket portion 281 of the catheter support 280 via the slot 218, and, if an engagement member 284 is provided for the catheter support 280, may be the engagement member 284.

Alternatively, if the lock 240 is positioned vertically, the protrusion may extend out of the slot 218 provided in the first member 220 of the introducer 210 through which the wall 277 of the actuator 270 passes.

Figure 39A:
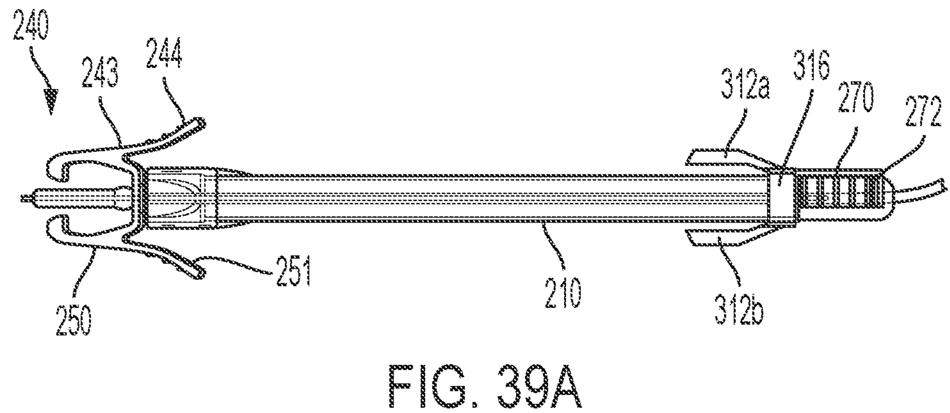
FIG. 39A is a top view of an inventive fluid transfer device in the first configuration, the fluid transfer device having a catheter support with two locking protrusion.
Figure 39B:
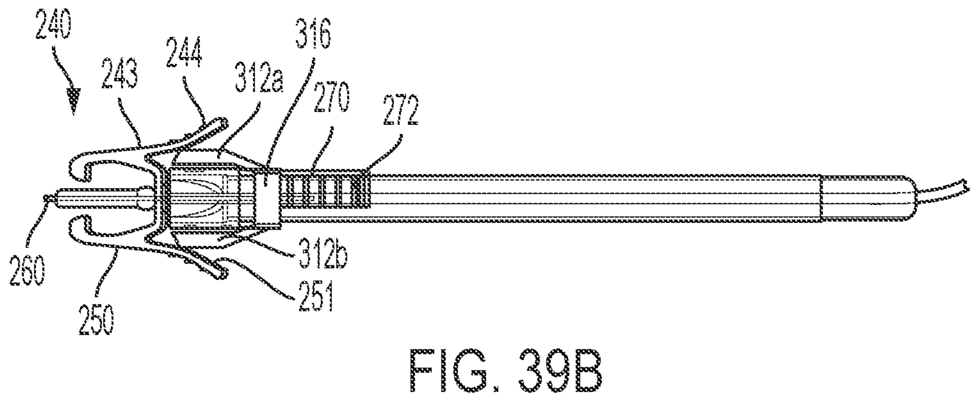
FIG. 39B is a top view of the inventive fluid transfer device of FIG. 39A in the second configuration.
Figure 40:
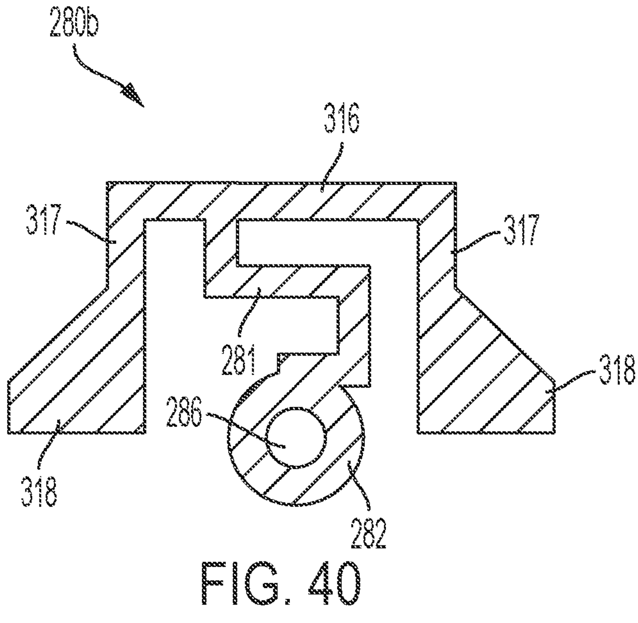
FIG. 40 is a cross-sectional view of the catheter support of FIGS. 39A and 39B.

As shown in FIGS. 39 and 40, the catheter support 280*b* may have more than one protrusion 312*a*, 312*b* may be provided, for example, one protrusion 312*a* corresponding to the first arm 243 of the lock 240 and one protrusion 312*b* corresponding to the second arm 250 of the lock 240. The protrusions 312*a*, 312*b* may include a common first portion 316 extending outwardly in a lateral direction above the top outer surface of the introducer 210, second portions 317 extending downwardly from the first portion 316 on opposite sides of the outer surface of the introducer 310, and third portions 318 extending distally from the second portions 317, where the third portions 318 enter the spaces between the arms 243, 250 of the lock 240 and the coupler 241. The first portion 316 is connected to the bracket portion 281 of the catheter support 280 via the slot 218, and, if an engagement member 284 is provided for the catheter support 280, may be the engagement member 284. The second protrusion 312*b* may be a mirror image of the first protrusion 312*a*.

Figure 41:
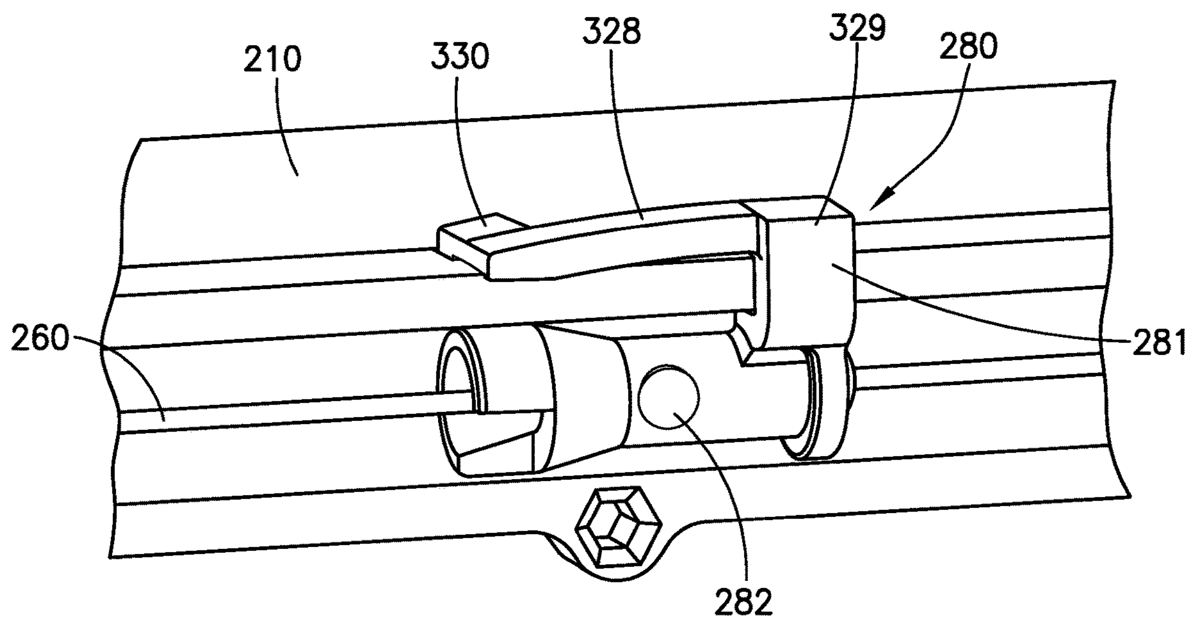
FIG. 41 is a partial cutaway view of a blood draw device according to a further aspect or embodiment of the present application, showing a catheter support.
Figure 42:
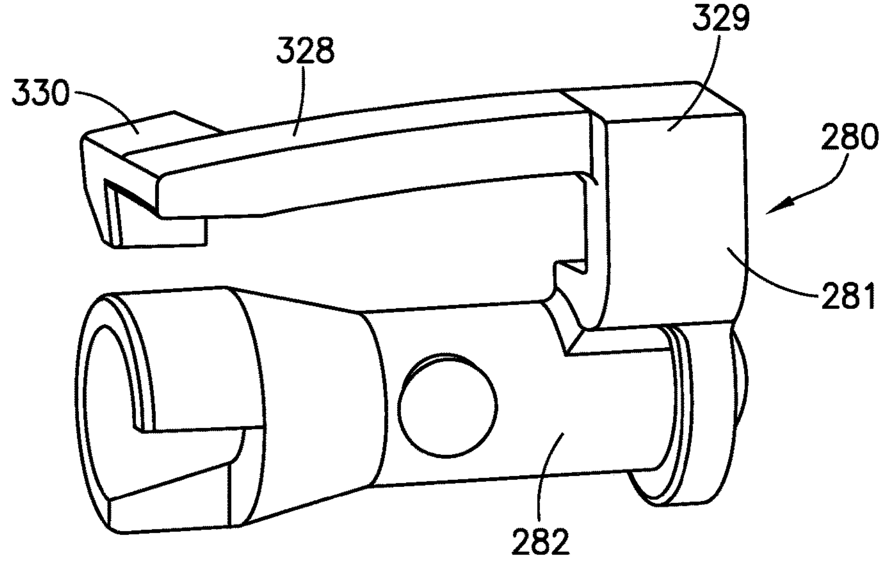
FIG. 42 is a perspective view of the catheter support of FIG. 41.

Referring to FIGS. 41 and 42, in a further aspect or embodiment, the bracket portion 281 of the catheter support 280 is biased against a portion of the introducer 210. The bracket portion includes a cantilever arm 328 having a first end 329 extending from the hub portion 282 of the catheter support 280 and a second end 330 opposite the first end 329, where, prior to assembly, the second end 330 of the cantilever arm 328 defines a first distance between the second end of the cantilever arm and the hub portion, and where, after assembly within the introducer 210, the cantilever arm 328 defines a second distance between the second end 330 of the cantilever arm 328 and the hub portion 282, with the second distance larger than the first distance. The gap between the hub portion 282 and the bracket portion 281 is small enough that the cantilever arm 328 pinches the internal rib portion of the introducer 210 that it wraps around. This provides friction between the introducer 210 and the catheter support 280 such that the catheter support 280 will not move under gravity but only when pushed on by assembly tooling or the actuator 270. This also increases the force required to overcome the detent 327. This gap is created by rotating the bracket portion 281 to cantilever the bracket portion 281 in the axial direction of the device 200. The cantilever arm 328 is molded in the curved down shape, but it could also be angled down.

Figure 43:
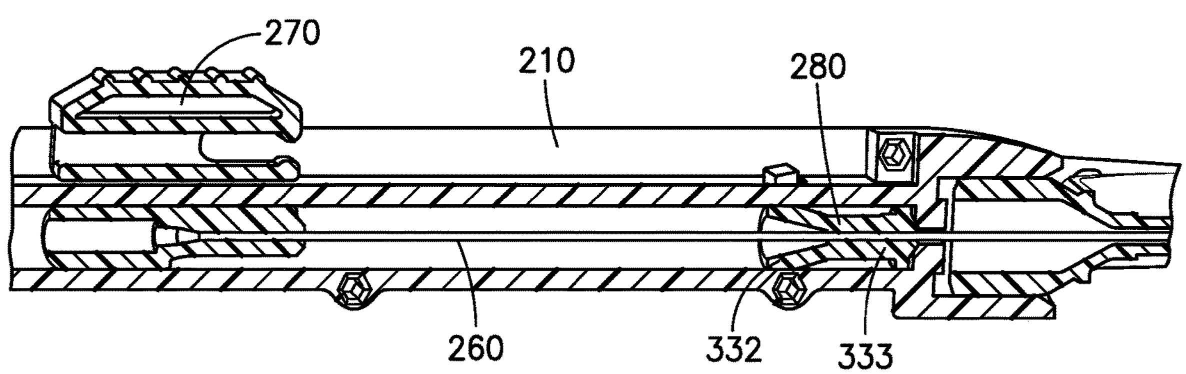
FIG. 43 is a cross-sectional view of a blood draw device according to a further aspect or embodiment of the present application.
Figure 44:
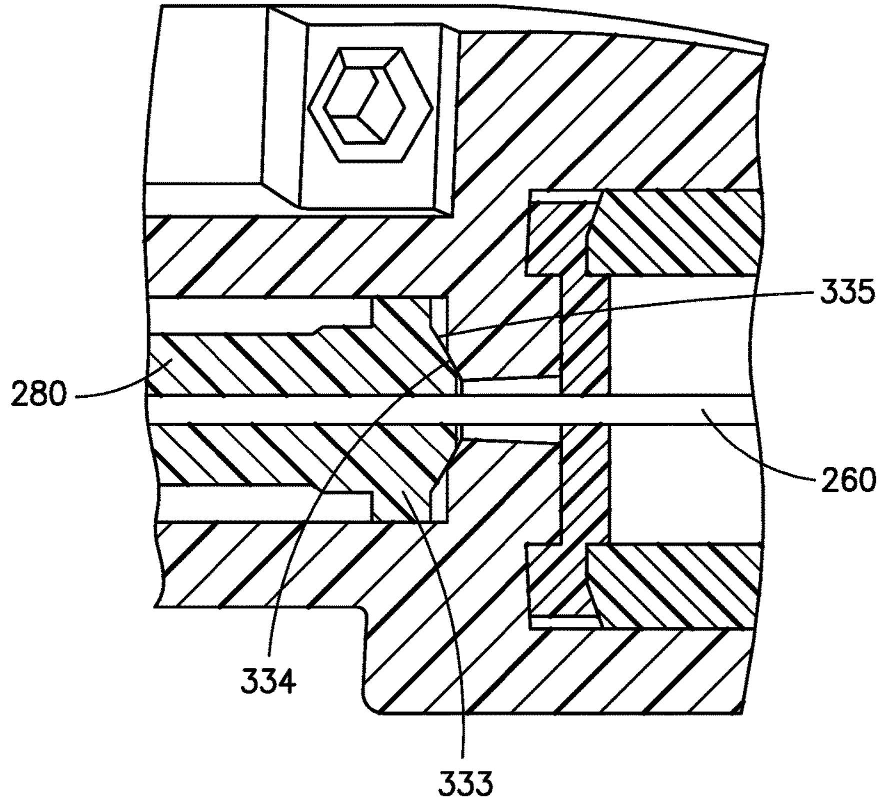
FIG. 44 is an enlarged cross-sectional view of the blood draw device of FIG. 43.
Figure 45:
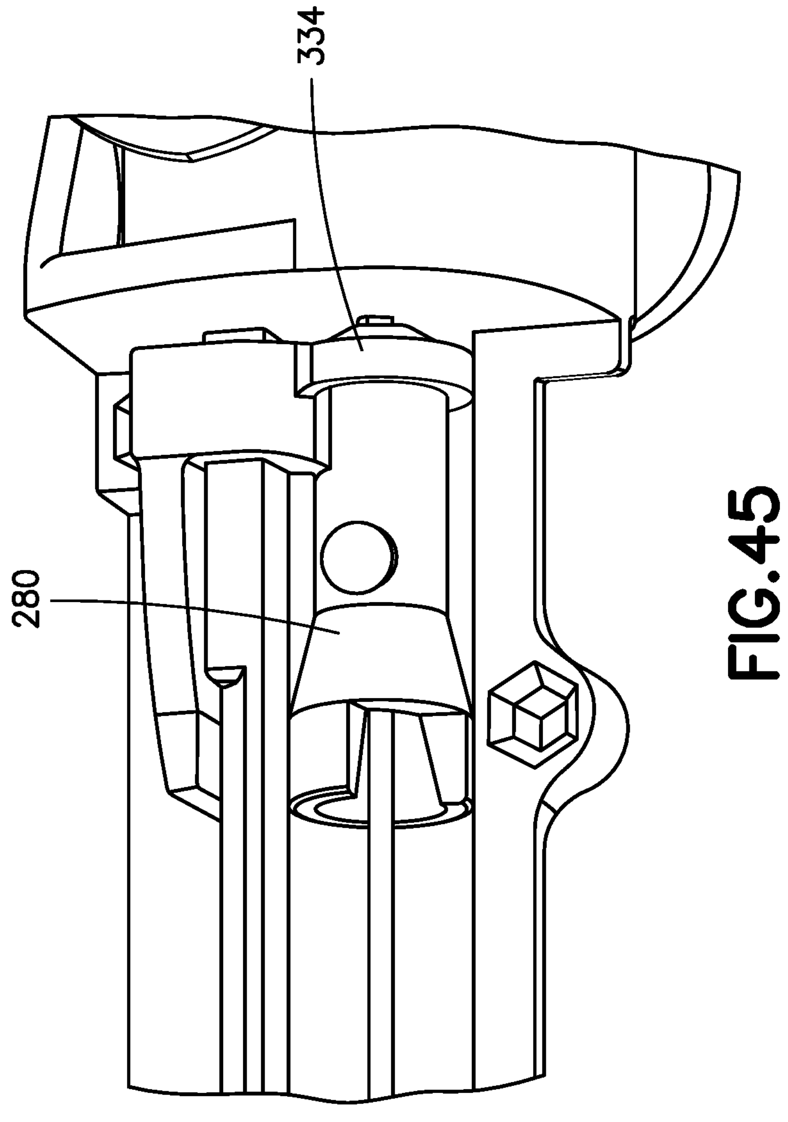
FIG. 45 is a partial cutaway view of the blood draw device of FIG. 43.

Referring to FIGS. 43-45, in a further aspect or embodiment, the catheter support 280 includes a first end 332 and a second end 333 positioned opposite the first end 332, with the second end 333 of the catheter support 280 including a nose cone 334 configured to engage a lead-in surface 335 of the introducer 210. The nose cone 334 matchings the lead-in surface 335 of the introducer 210 and is configured to self-align when the catheter support 280 is pushed all the way distally. The nose cone 334 may also engage in a press fit with the introducer 210 to lock it in place when it is fully advanced. The back end of the catheter support 280 has a large funnel leading into the through hole, as noted above.

Feeding the catheter 260 into the large funnel in the catheter support 280 is easier, which then funnels the catheter 260 into the small hole in the introducer 210. The large funnel also has a portion cut out to make it even easier to start the catheter into the large funnel. The catheter 260 can be loaded from the back of the support 280 or from the side. The support 280 is then retracted proximally after the catheter 260 is assembled. The support 280 can then be pushed back to the same position by the actuator 270, and the same nose cone 334 can again align the support 280 with the introducer 210 to center the catheter 260 in the hole of the introducer 210. A stop may also be included in the introducer 210 that can also prevent the support 280 from advancing all the way distally and prevent the nose cone 334 from contacting the introducer 210 to prevent interaction that may push the introducer 210 and affect the ability to seal.

Figure 46:
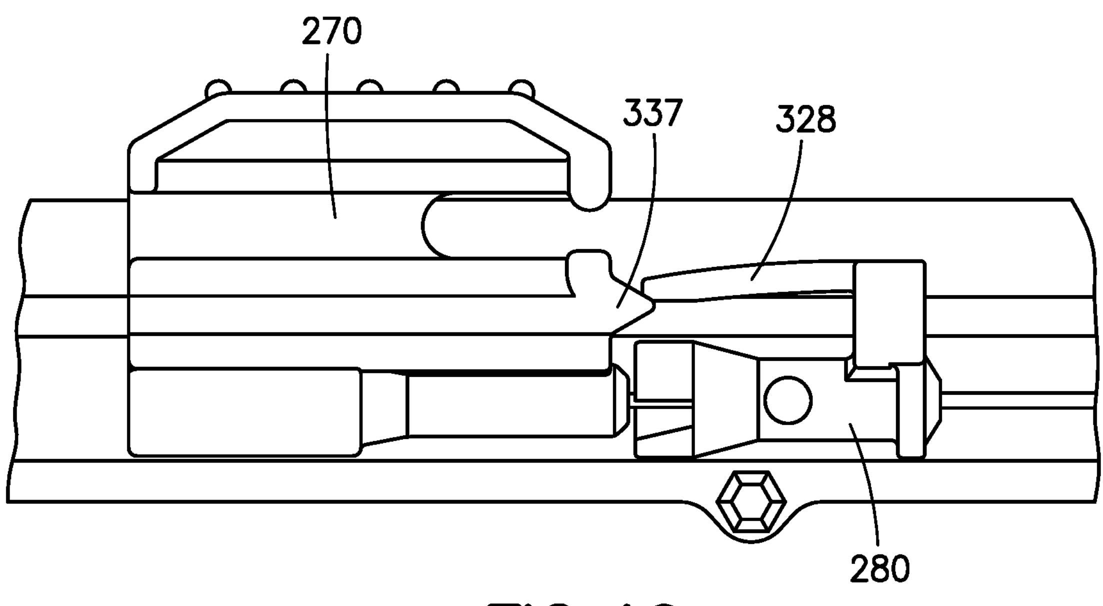
FIG. 46 is a partial cutaway view of a blood draw device according to a further aspect or embodiment of the present application.
Figure 47:
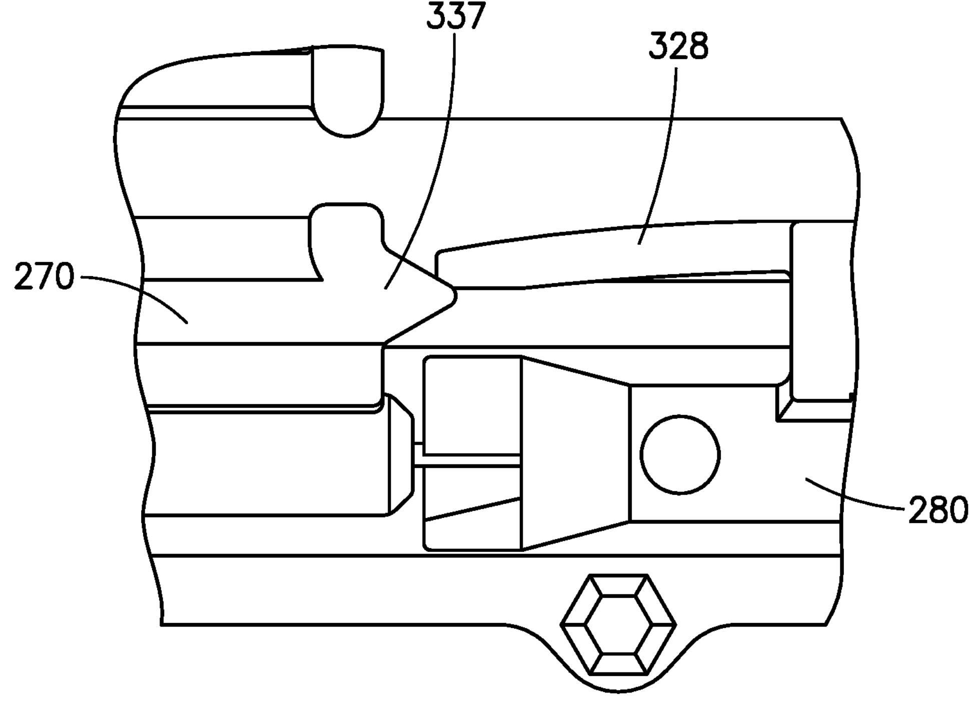
FIG. 47 is an enlarged view of the blood draw device of FIG. 46.
Figures 48, 49:
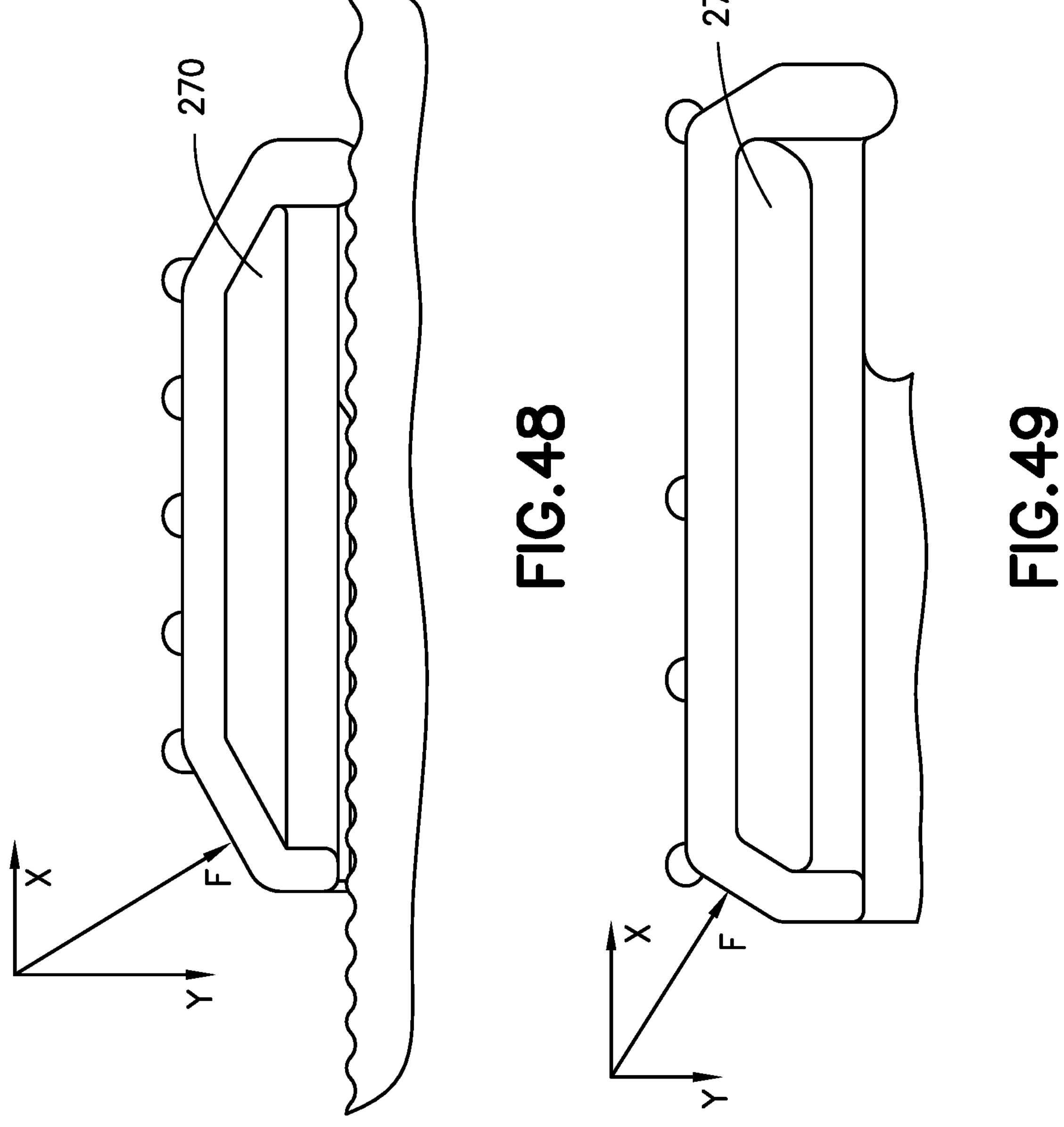
FIG. 48 is a front view of an actuator of a blood draw device according to a further aspect or embodiment of the present application.
FIG. 49 is a front view of an actuator of a blood draw device according to a further aspect or embodiment of the present application.
Figures 50, 51:
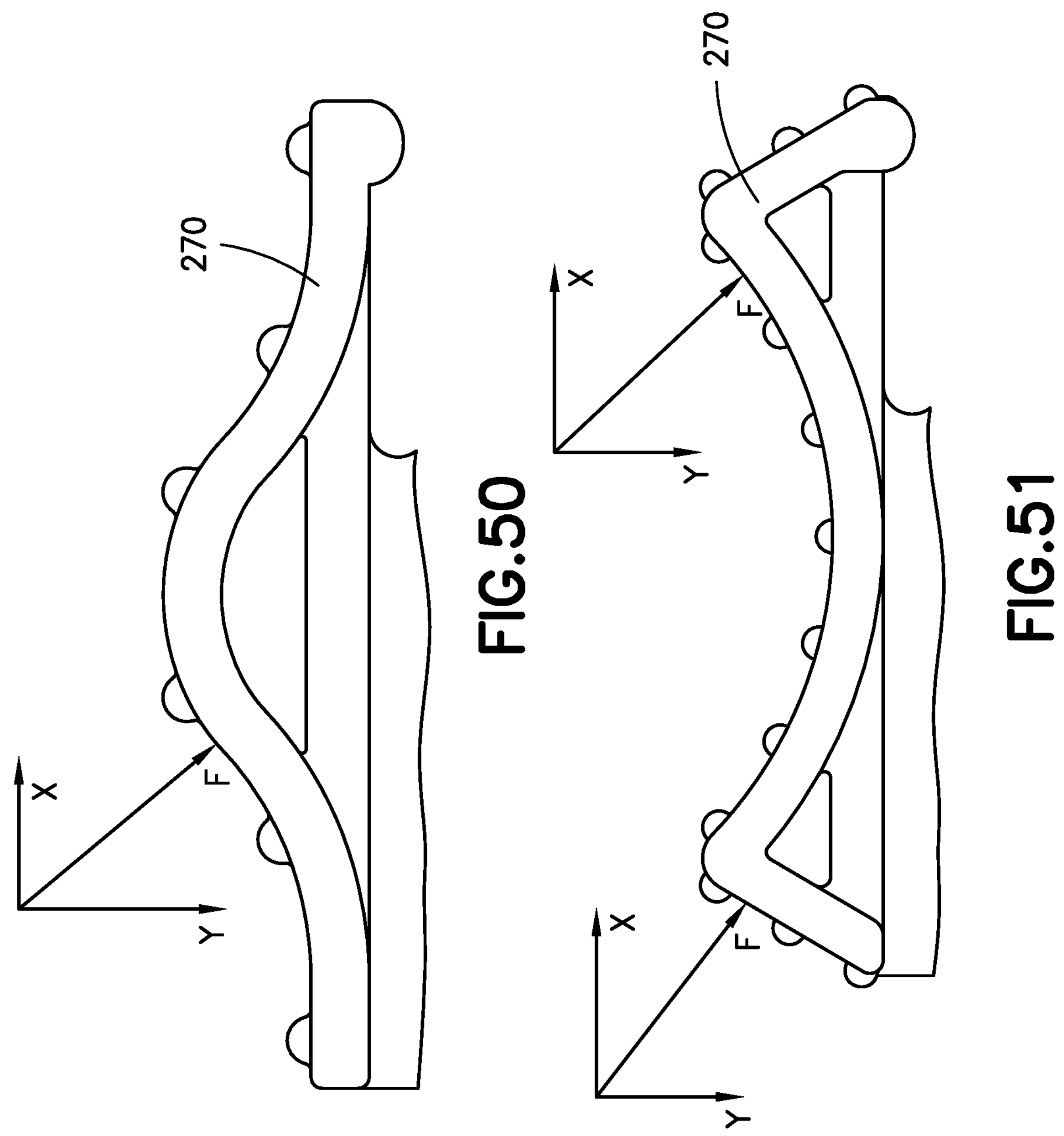
FIG. 50 is a front view of an actuator of a blood draw device according to a further aspect or embodiment of the present application.
FIG. 51 is a front view of an actuator of a blood draw device according to a further aspect or embodiment of the present application.

Referring to FIGS. 46 and 47, the actuator 270 includes a cam member 337 configured to engage and move the cantilever arm 328. The cam member 337 of the actuator 270 is configured to lift the cantilever arm 328 over the detent 327. The cam member 337 is angled and configured to engage the cantilever arm 328 to push it away from the detent 327 with a camming action. The force to push the arm 328 over the detent 327 can be reduced if the friction between the detent 327 and the arm 328 is less than the catch of the arm 328 and the detent 327. This may be accomplished with either lubrications, coatings, differences of materials, additives in the resin to increase lubricity, or by using a shallower angle than the detent angle. The detent angle can be made steeper, and the feature would lift it over the steep angle with acceptable force. The detent angle could even be square, which would require the feature to completely lift the arm catch to clear the detent. The advantage to a steeper detent angle is to hold the support more securely in place before use.

Referring to FIGS. 48-51, further aspects or embodiments of a finger interface of the actuator 270 are shown. A round, almost flat finger interface surface with ribs, such as the finger interface shown in FIG. 29, requires a significant amount of force (F) in order to gain the friction force (X) needed to slide it forward. Most of the force (F) from a healthcare worker is actually pushing the actuator down (Y), which does not advance the actuator 270. Changing the shape of the actuator 270, as shown in FIGS. 48-51, allows more of the fingers force (F) to push it forward (X), and repositioning the ribs to be more effective at providing friction, or even a small catch. The actuator 270 may have ribs (as shown), touch bumps, or a roughened surface to add friction.

Figure 52:
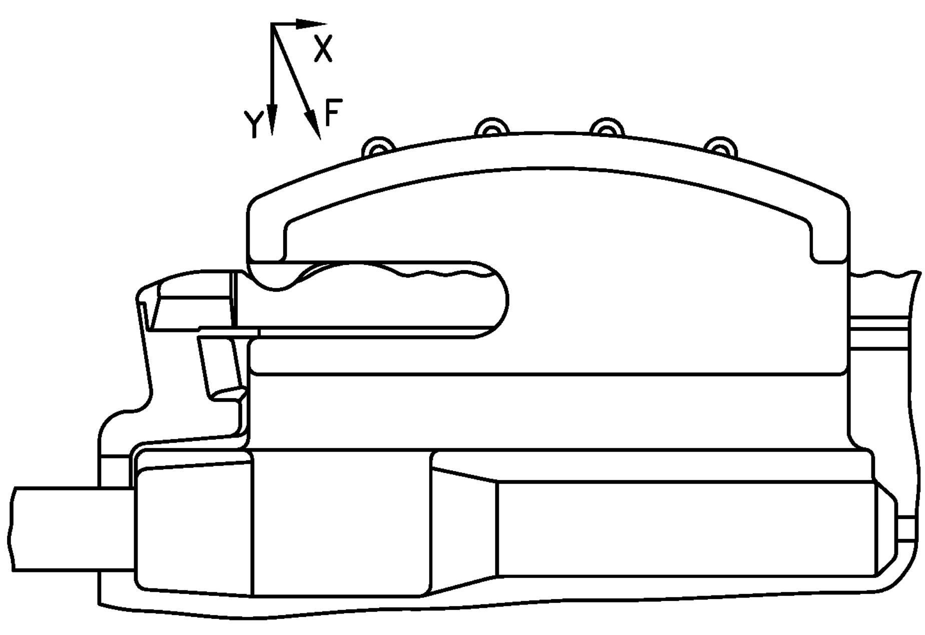
FIG. 52 is a partial front view of a prior art actuator and introducer of a blood draw device.
Figure 53:
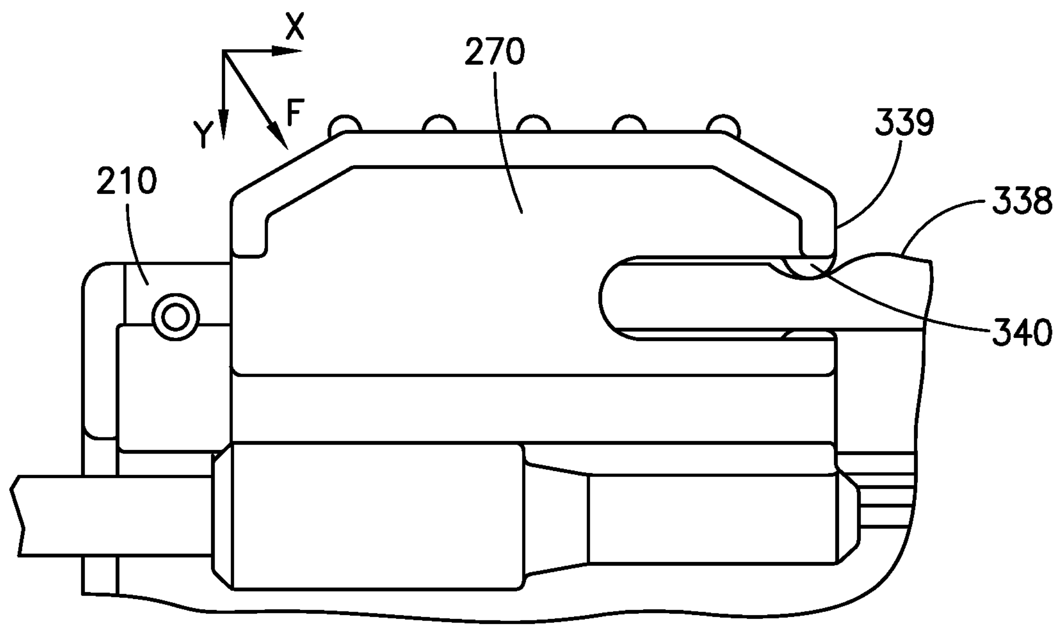
FIG. 53 is a partial front view of an actuator and introducer of a blood draw device according to a further aspect or embodiment of the present application.

Referring to FIGS. 52 and 53, in a further aspect or embodiment, the introducer 210 includes a detent 338 adjacent to the ribs 236, and a distal end 339 of the actuator 270 includes a tab 340 configured to engage the detent 338 and the ribs 236 as the actuator 270 is moved relative to the introducer 210. The tab 340 is similar to and functions similarly to the tab 273, as discussed above. The detent 338 prevents the actuator 270 from moving forward prior to the use of the device 200. As shown in FIG. 52, in the prior art device, the actuator pinch is directly below the side where the healthcare worker pushes to advance the actuator. As shown below, most of the force applied to advance the actuator is actually pushing the top portion of the pinch down into the detent, making it harder to overcome and advance. Moving the slot and the tab 340 to the other end of the actuator 340 is configured to still pinch the introducer 210 and retain the actuator 270 in the detent 338, but with the force to advance the actuator 270 no longer directly above the tab 340. The downward force from the healthcare worker will no longer drive the top of the pinch into the detent 338, making it harder to overcome thereby reducing the force required to advance the actuator 270.

Figure 54:
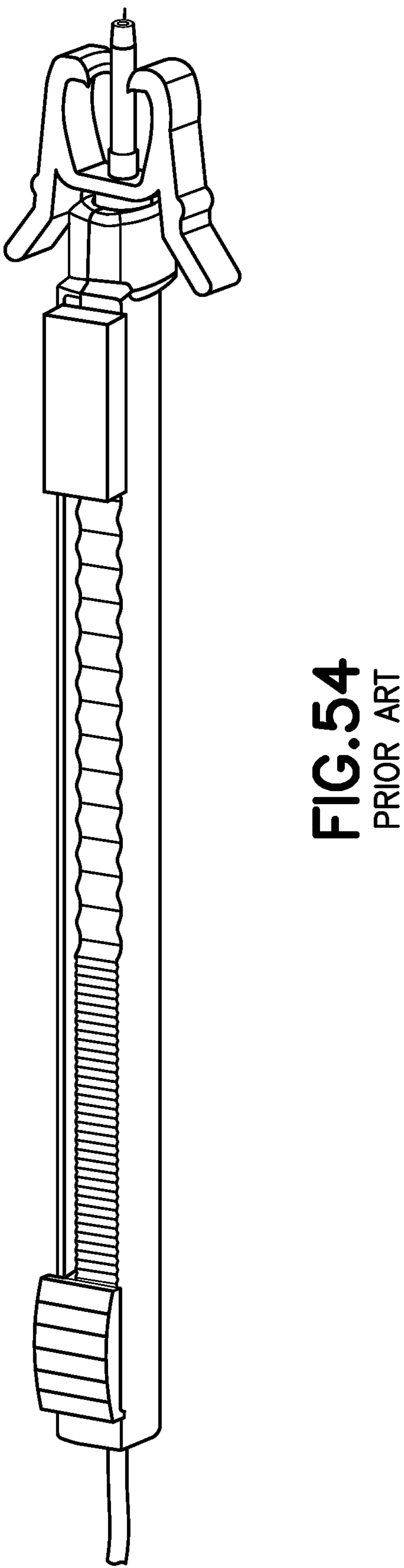
FIG. 54 is a perspective view of a prior art blood draw device.
Figures 55, 56:
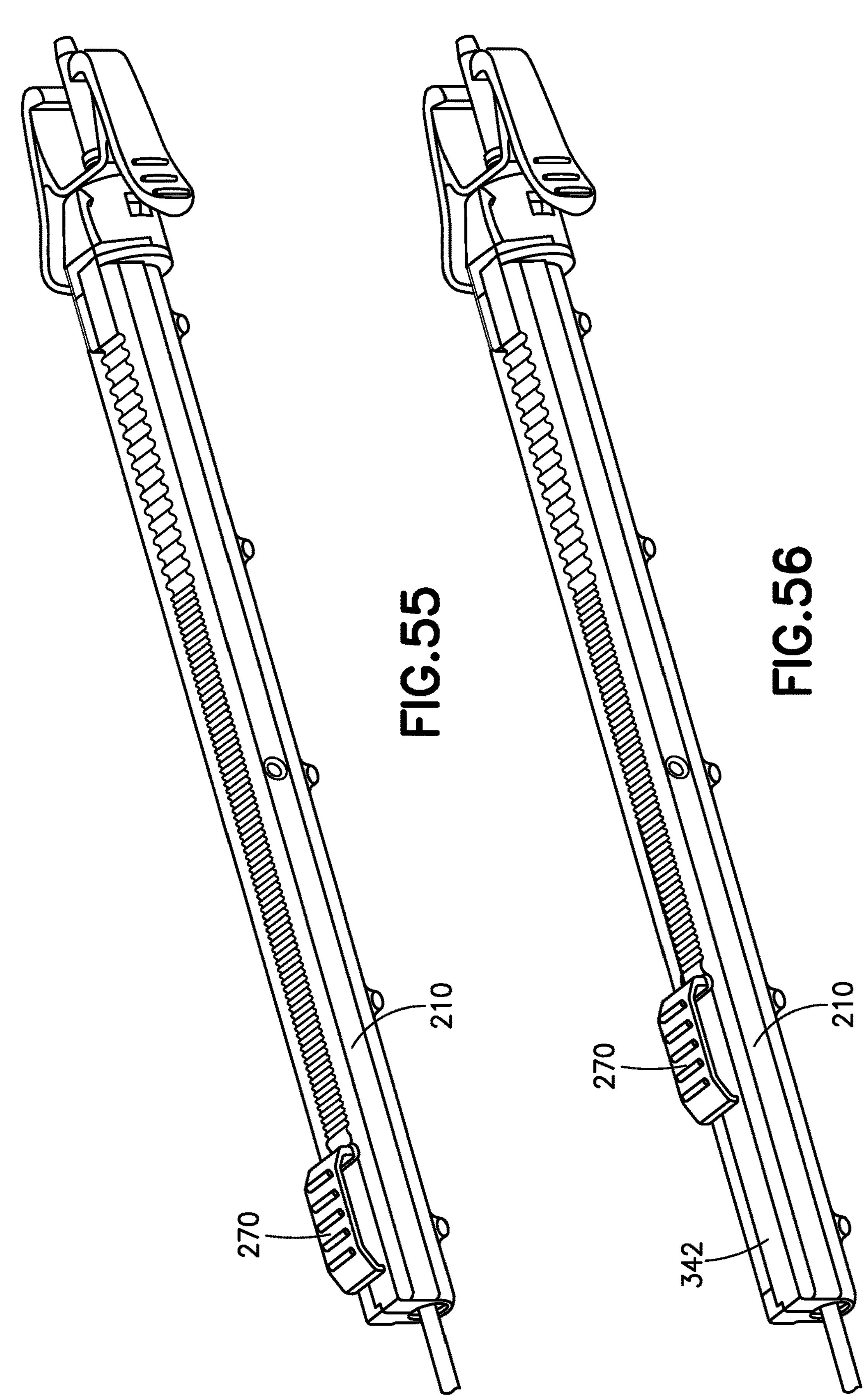
FIG. 55 is a perspective view of a blood draw device according to a further aspect or embodiment of the present application.
FIG. 56 is a perspective view of a blood draw device according to a further aspect or embodiment of the present application.

Referring to FIGS. 54-56, in a further aspect or embodiment, the detent 338 is positioned intermediate the proximal end portion 231 and the distal end portion 232 of the introducer 210, with the introducer 210 including an advancement reducer 342 extending from the proximal end portion 331 to the detent 338. For smaller gauges, such as 24 ga, it is desirable to reduce the activated length of the device 200 to accommodate shorter introducer catheters and to extend into the vein less. As shown in FIG. 54, a conventional device uses an additional part that limits the movement of the actuator on the distal end, which requires an additional part, and the small catheter tube still needs to be as long as a full extension device. Referring to FIGS. 55 and 56, the device 200 can incorporate the advancement reducer 342 as part of the introducer 210, which keeps the overall part count of the product the same. The advancement reducer 342 is also at the proximal end portion 231 so the overall length of the catheter 260 can be reduced, which will increase the flow rate of the device. Alternatively, the advancement reducer 342 could be incorporated into the distal end portion 232 of the introducer 210. The detent 338 and ratchet ribs 236, small and large, are also part of the introducer 210, such as the second member 230, so they can be adjusted and optimized for the shorter activation length.

Figures 57, 58:
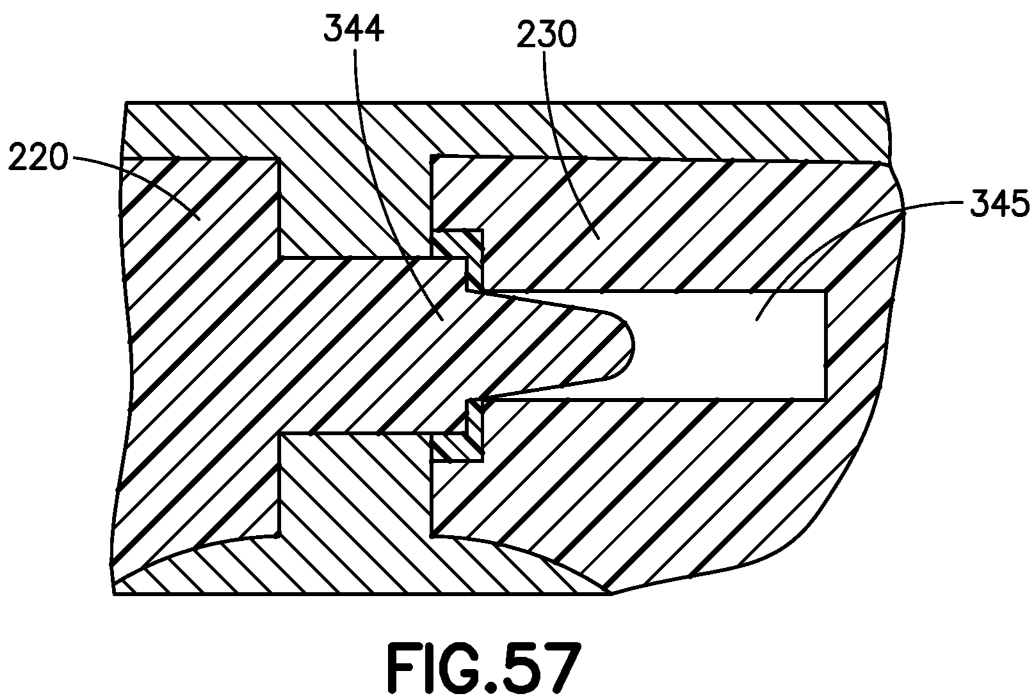
FIG. 57 is a cross-sectional view of a connection between a first member and a second member of an introducer of a blood draw device according to a further aspect or embodiment of the present application.
FIG. 58 is a cross-sectional view of a connection between a first member and a second member of an introducer of a blood draw device according to a further aspect or embodiment of the present application.

Referring to FIGS. 57 and 58, in a further aspect or embodiment, the first member 220 of the introducer 210 includes a plurality of pegs 344 and the second member 230 of the introducer 210 includes a plurality of openings 345 configured to receive the respective pegs 344. The pegs 344 are secured within the respective openings 345 via ultrasonic welding 346 to secure the first member 220 of the introducer 210 to the second member 230 of the introducer 210. In one aspect or embodiment, the pegs 344 are larger than the openings 345. Ultrasonic energy is used to vibrate the introducer 210 with the pegs 344 until the overlap between the peg 344 and the opening 345 melt and joint together. The ultrasonic energy is then stopped, and the melted plastic hardens again creating a strong and tight bond. Each peg 344 and opening 345 interface creates an independent bond so a failure of one does not compromise the rest. The peg 344 and the opening 345 also have features to help align them to each other and to capture any extra plastic that may flow away from the joint as shown in FIGS. 56 and 58. A variety of joint types could be used including a step, butt, tongue and groove, or shear joint.

In use, as described above, the proximal end portion of the secondary catheter is coupled to a fluid reservoir, fluid source, syringe, evacuated container holder (e.g., having a sheathed needle or configured to be coupled to a sheathed needle), pump, and/or the like, and the lock of the fluid transfer device is coupled to the PIV. The actuator is moved relative to the introducer to advance the catheter from the first position, in which the catheter is disposed within at least one of an inner volume of the introducer and the lock, toward the second position, in which at least a portion of the catheter is disposed beyond at least a portion of the PIV, and the distal surface of the catheter is located at the desired distance within the PIV or the vein of the patient. When the catheter has been inserted through the PIV the desired distance, a blood sample is drawn from the patient or a drug is injected into the patient. When the sample draw or injection is complete, the actuator is moved relative to the introducer to retract the catheter from the PIV until at least the distal surface of the catheter is received within the lock, and the lock is disengaged from the PIV.

The invention claimed is:

1. A blood draw device comprising:

a catheter having a proximal end portion and a distal end portion and defining a lumen extending through the proximal end portion and the distal end portion;

an introducer having a proximal end portion and a distal end portion, the introducer defining an inner volume configured to movably receive the catheter, the distal end portion of the introducer having a lock configured to couple the introducer to an indwelling peripheral intravenous line;

an actuator movably coupled to the introducer, the actuator having a first portion disposed outside of the introducer and a second portion disposed in the inner volume of the introducer and coupled to the proximal end portion of the catheter, the actuator configured to move relative to the introducer to move the catheter between a first position, in which the catheter is disposed within the introducer, and a second position, in which the distal end portion of the catheter is disposed beyond the distal end portion of the introducer such that at least a first portion of the catheter is disposed within the indwelling peripheral intravenous line when the introducer is coupled to the indwelling peripheral intravenous line; and a catheter support defining a passageway, movably coupled to the introducer, and positioned between the actuator and the distal end portion of the introducer, the catheter support comprising a bracket portion and a hub portion including the passageway and extending from the bracket portion, wherein the catheter extends from the second portion of the actuator through the passageway of the catheter support to the distal end portion of the introducer, and during movement of the actuator to move the catheter from the first position to the second position, the actuator contacts the catheter support and moves the catheter support with respect to the introducer, and wherein the bracket portion of the catheter support is biased against the introducer.

2. The blood draw device of claim 1, wherein the bracket portion comprises a cantilever arm having a first end extending from the hub portion of the catheter support and a second end opposite the first end, wherein, prior to assembly, the second end of the cantilever arm defines a first distance between the second end of the cantilever arm and the hub portion, and wherein, after assembly within the introducer, the cantilever arm defines a second distance between the second end of the cantilever arm and the hub portion, the second distance larger than the first distance.

3. The blood draw device of claim 2, wherein the actuator comprises a cam member configured to engage and move the cantilever arm.

4. The blood draw device of claim 3, further comprising a detent positioned in a slot in the introducer, wherein the detent engages the catheter support to restrict movement of the catheter support, and wherein the cam member of the actuator is configured to lift the cantilever arm over the detent.

5. A blood draw device comprising:

a catheter having a proximal end portion and a distal end portion and defining a lumen extending through the proximal end portion and the distal end portion;

an introducer having a proximal end portion and a distal end portion, the introducer defining an inner volume configured to movably receive the catheter, the distal end portion of the introducer having a lock configured to couple the introducer to an indwelling peripheral intravenous line;

an actuator movably coupled to the introducer, the actuator having a first portion disposed outside of the introducer and a second portion disposed in the inner volume of the introducer and coupled to the proximal end portion of the catheter, the actuator configured to move relative to the introducer to move the catheter between a first position, in which the catheter is disposed within the introducer, and a second position, in which the distal end portion of the catheter is disposed beyond the distal end portion of the introducer such that at least a first portion of the catheter is disposed within the indwelling peripheral intravenous line when the introducer is coupled to the indwelling peripheral intravenous line; and a catheter support defining a passageway, movably coupled to the introducer, and positioned between the actuator and the distal end portion of the introducer, the catheter support having a first end and a second end positioned opposite the first end, wherein the catheter extends from the second portion of the actuator through the passageway of the catheter support to the distal end portion of the introducer, and during movement of the actuator to move the catheter from the first position to the second position, the actuator contacts the catheter support and moves the catheter support with respect to the introducer, and wherein the second end of the catheter support comprises a nose cone configured to engage a lead-in surface of the introducer.

6. The blood draw device of claim 5, wherein the nose cone is engageable with the introducer to lock in place when the introducer is fully advanced.

7. The blood draw device of claim 6, wherein the nose cone engages with the introducer in a press-fit with the introducer.

8. The blood draw device of claim 5, wherein the lead-in surface of the introducer is configured to self-align when the catheter support is advanced to the second position.

9. A blood draw device comprising:

a catheter having a proximal end portion and a distal end portion and defining a lumen extending through the proximal end portion and the distal end portion;

an introducer having a proximal end portion and a distal end portion, the introducer defining an inner volume configured to movably receive the catheter, the distal end portion of the introducer having a lock configured to couple the introducer to an indwelling peripheral intravenous line;

an actuator movably coupled to the introducer, the actuator having a first portion disposed outside of the introducer and a second portion disposed in the inner volume of the introducer and coupled to the proximal end portion of the catheter, the actuator having a proximal end and a distal end positioned opposite the proximal end, the actuator configured to move relative to the introducer to move the catheter between a first position, in which the catheter is disposed within the introducer, and a second position, in which the distal end portion of the catheter is disposed beyond the distal end portion of the introducer such that at least a first portion of the catheter is disposed within the indwelling peripheral intravenous line when the introducer is coupled to the indwelling peripheral intravenous line; and a catheter support defining a passageway, movably coupled to the introducer, and positioned between the actuator and the distal end portion of the introducer, wherein the catheter extends from the second portion of the actuator through the passageway of the catheter support to the distal end portion of the introducer, and during movement of the actuator to move the catheter from the first position to the second position, the actuator contacts the catheter support and moves the catheter support with respect to the introducer, and wherein the introducer comprises a detent and a plurality of ribs and the distal end of the actuator comprises a tab configured to engage the detent and the plurality of ribs as the actuator is moved relative to the introducer.

10. The blood draw device of claim 9, wherein the detent is positioned intermediate the proximal end portion of the introducer and the distal end portion of the introducer, and wherein the introducer comprises an advancement reducer extending from the proximal end portion to the detent.

11. A blood draw device comprising:

a catheter having a proximal end portion and a distal end portion and defining a lumen extending through the proximal end portion and the distal end portion;

an introducer having a proximal end portion and a distal end portion, the introducer comprises a first member attached to a second member, the introducer defining an inner volume configured to movably receive the catheter, the distal end portion of the introducer having a lock configured to couple the introducer to an indwelling peripheral intravenous line;

an actuator movably coupled to the introducer, the actuator having a first portion disposed outside of the introducer and a second portion disposed in the inner volume of the introducer and coupled to the proximal end portion of the catheter, the actuator configured to move relative to the introducer to move the catheter between a first position, in which the catheter is disposed within the introducer, and a second position, in which the distal end portion of the catheter is disposed beyond the distal end portion of the introducer such that at least a first portion of the catheter is disposed within the indwelling peripheral intravenous line when the introducer is coupled to the indwelling peripheral intravenous line; and a catheter support defining a passageway, movably coupled to the introducer, and positioned between the actuator and the distal end portion of the introducer, wherein the catheter extends from the second portion of the actuator through the passageway of the catheter support to the distal end portion of the introducer, and during movement of the actuator to move the catheter from the first position to the second position, the actuator contacts the catheter support and moves the catheter support with respect to the introducer, and wherein the first member of the introducer comprises one of a peg and an opening and the second member of the introducer comprises the other of the peg and the opening, the peg secured within the opening via an ultrasonic weld to secure the first member of the introducer to the second member of the introducer.

12. The blood draw device of claim 11, further comprising a plurality of pegs positioned on one of the first member of the introducer and the second member of the introducer and a plurality of openings on the other of the first member of the introducer and the second member of the introducer for receiving the respective plurality of pegs.

* * * * *